(12) United States Patent
Lewis et al.

(10) Patent No.: US 11,473,052 B2
(45) Date of Patent: *Oct. 18, 2022

(54) *BACILLUS SUBTILIS* SUBSPECIES

(71) Applicant: Novozymes A/S, Bagsvaerd (DK)

(72) Inventors: Derrick Lewis, Durham, NC (US);
Marianne Thorup Cohn, Copenhagen (DK); Adam Nelson, Salem, VA (US); Preben Nielsen, Horsholm (DK); Ravi Kumar, Davis, CA (US)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/542,135

(22) PCT Filed: Jan. 22, 2016

(86) PCT No.: PCT/US2016/014505
§ 371 (c)(1),
(2) Date: Jul. 7, 2017

(87) PCT Pub. No.: WO2016/118850
PCT Pub. Date: Jul. 28, 2016

(65) Prior Publication Data
US 2018/0258502 A1    Sep. 13, 2018

Related U.S. Application Data

(60) Provisional application No. 62/106,841, filed on Jan. 23, 2015, provisional application No. 62/153,038, filed on Apr. 27, 2015, provisional application No. 62/260,800, filed on Nov. 30, 2015.

(51) Int. Cl.

| | | |
|---|---|---|
| *C12N 1/20* | (2006.01) | |
| *A23K 10/18* | (2016.01) | |
| *A61K 35/742* | (2015.01) | |
| *A61P 31/04* | (2006.01) | |
| *A61K 35/00* | (2006.01) | |
| *C12R 1/125* | (2006.01) | |

(52) U.S. Cl.
CPC .......... *C12N 1/20* (2013.01); *A23K 10/18* (2016.05); *A61K 35/742* (2013.01); *A61P 31/04* (2018.01); *C12N 1/205* (2021.05); *A61K 2035/115* (2013.01); *C12R 2001/125* (2021.05); *Y02A 50/30* (2018.01)

(58) Field of Classification Search
CPC ........................................................ C12N 1/20
See application file for complete search history.

(56) References Cited

U.S. PATENT DOCUMENTS

| | | | |
|---|---|---|---|
| 4,919,936 A | 4/1990 | Iwanami | |
| 5,733,355 A | 3/1998 | Hibino | |
| 8,540,981 B1 | 9/2013 | Wehnes | |
| 8,906,668 B2 | 12/2014 | Henn et al. | |
| 2004/0101525 A1 | 5/2004 | Lin | |
| 2009/0280090 A1 | 11/2009 | Rehberger | |
| 2009/0318292 A1 | 12/2009 | Kong | |
| 2011/0318289 A1 | 12/2011 | Frodyma | |
| 2013/0136695 A1 | 5/2013 | Hargis | |
| 2013/0330307 A1 | 12/2013 | Millan | |
| 2014/0037582 A1 | 2/2014 | Romero | |
| 2014/0234279 A1 | 8/2014 | Millan | |

FOREIGN PATENT DOCUMENTS

| | | |
|---|---|---|
| CN | 103882097 | 6/2014 |
| WO | 2007/064741 A2 | 6/2007 |
| WO | 2010/033714 A1 | 3/2010 |
| WO | 2012/009712 A2 | 1/2012 |
| WO | 2012/105805 A2 | 9/2012 |
| WO | 2013/029013 A1 | 2/2013 |
| WO | 2013/096369 A1 | 6/2013 |
| WO | 2013/153159 A1 | 10/2013 |
| WO | 2014/169046 A1 | 10/2014 |

OTHER PUBLICATIONS

Zeigler. E0TXL5_BACPZ. UniProtKB/TrEMBL. 2010.*
Paineau et al., FEMS Immunol. Med. Microbiol., vol. 53, pp. 107-113 (2008).
Anonymous, EFSA Journal, vol. 8, No. 3, article 1552, pp. 1-7 (2010).
Anonymous, EFSA Journal, vol. 10, No. 1, article 2536, pp. 1-19 (2012).
Anonymous, EFSA Supporting Publication, article EN-587, pp. 1-13 (2014).
Essghaier et al., Journal of Applied Microbiology, vol. 106, No. 3, pp. 833-846 (2009).
Gang et al., Biomed. Environ. Sci., vol. 28, No. 8, pp. 620-625 (2015).
Jayaraman et al., Poultry Science, vol. 92, No. 2, pp. 370-374 (2013).
Knap et al., Avian Diseases, vol. 54, No. 2, pp. 931-935 (2010).
Maruta et al., Anim. Sci. Technol. (Jpn.), vol. 67, No. 5, pp. 403-409 (1996).
Prieto et al., Marine Drugs, vol. 12, No. 5, pp. 2422-2445 (2014).
Sathishkumar et al., Kemin Animal Nutrition and Health, "Influence of CLOSTAT on Production Performance of Commercial Layers (BV 300)" (2013).
Tactacan et al., J. Appl. Poult. Res., vol. 22, No. 4, pp. 825-831 (2013).
Teo et al., J. Appl. Poult. Res., vol. 15, No. 2, pp. 229-235 (2006).

* cited by examiner

*Primary Examiner* — Yong D Pak
(74) *Attorney, Agent, or Firm* — Adam Rucker

(57) ABSTRACT

The present invention relates to novel subspecies of *Bacillus*. The novel subspecies can improve health and performance of production animals. In one embodiment the *Bacillus subtilis* subspecies has activity against *Clostridium perfringens* and/or *E. coli*. The invention further relates to compositions comprising one or more strains of the *Bacillus subtilis* subspecies and to use of the strain(s) of the *Bacillus subtilis* subspecies in an animal feed.

7 Claims, 4 Drawing Sheets

Figure 2:
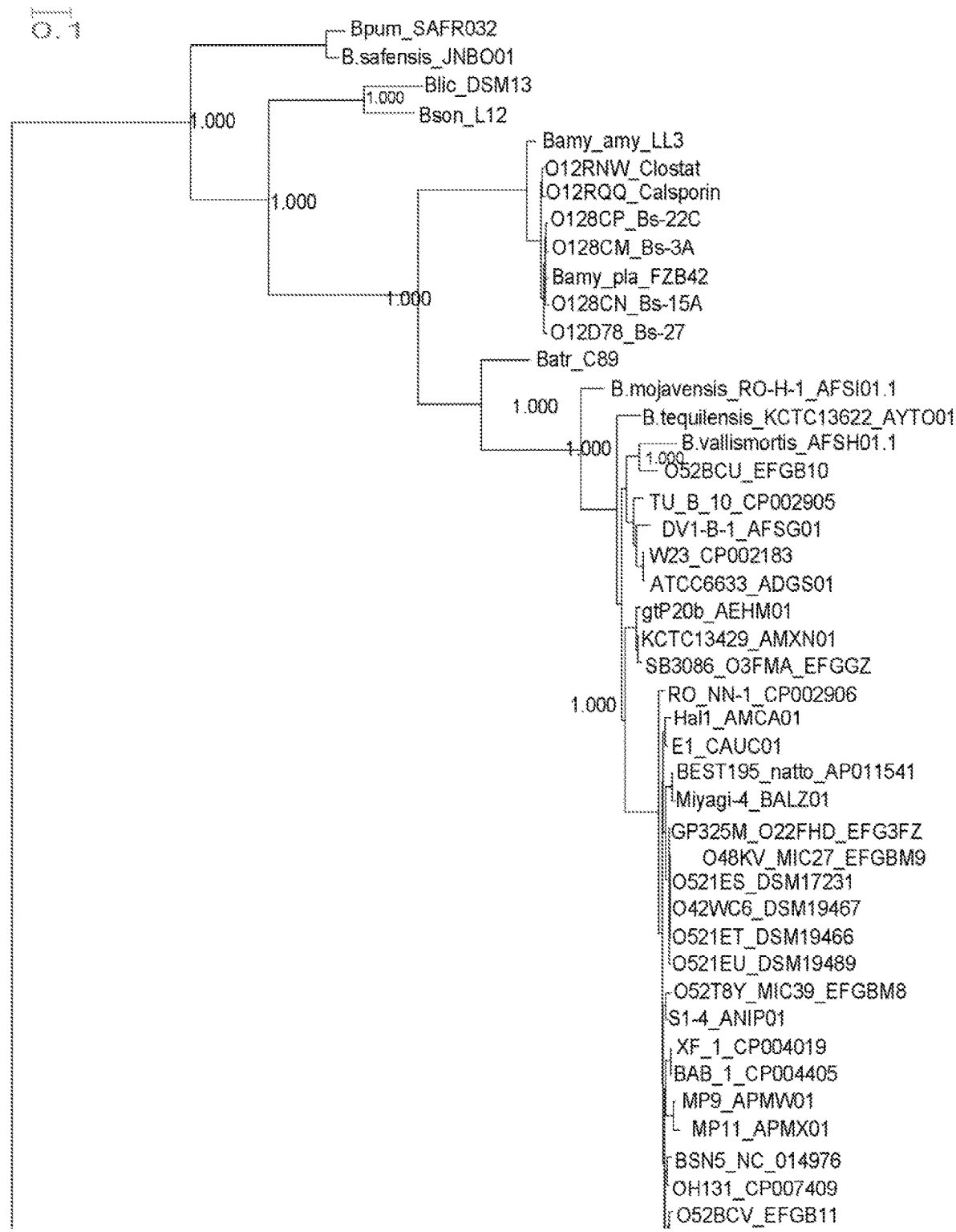
Figure 2:
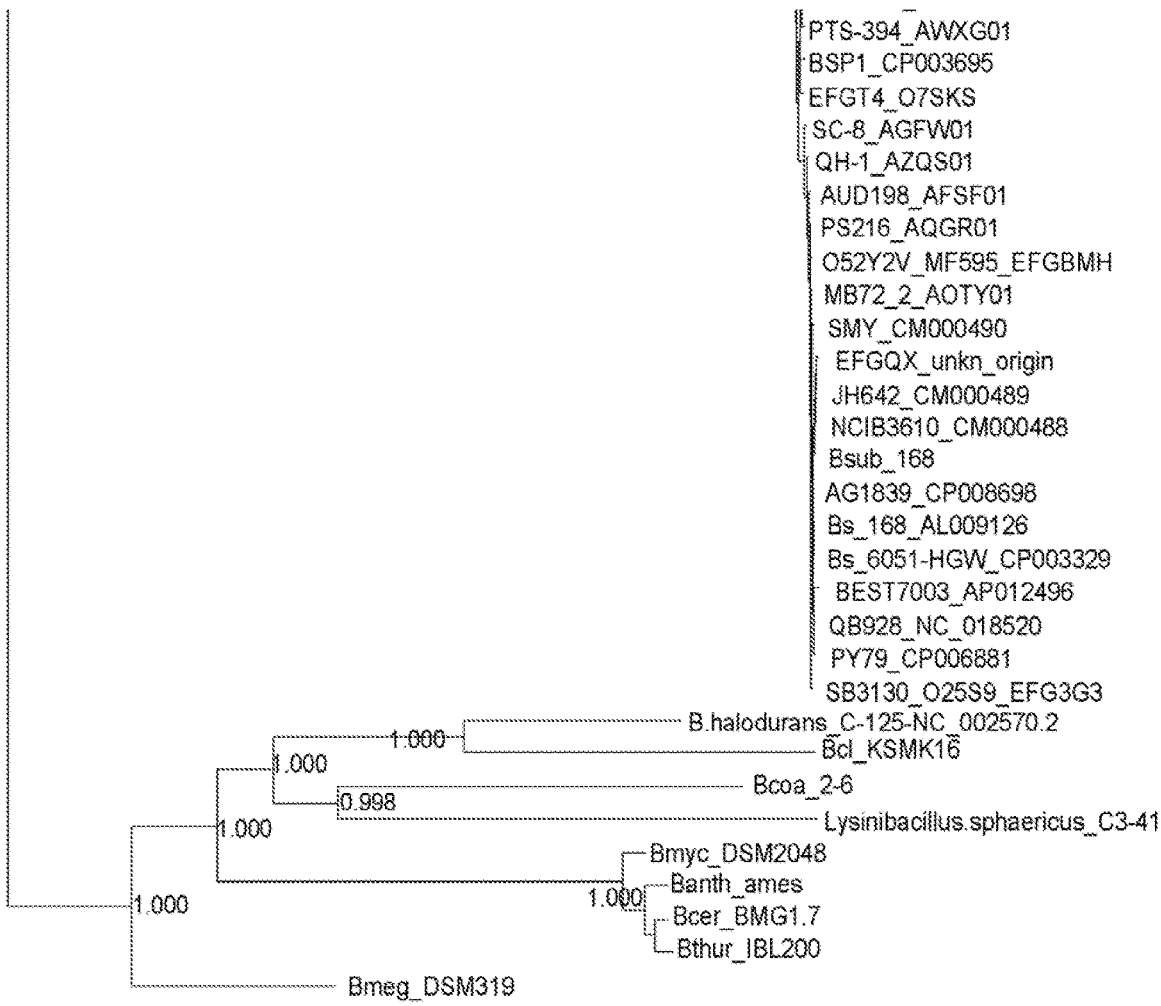

Specification includes a Sequence Listing.

Figure 1

| Bamy= *Bacillus amyloliquefaciens* | Batr= *B. atrophaeus* | Bsub= *B. subtilis* | Bthu= *B. thuringiensis* |
|---|---|---|---|
| Blic= *B. licheniformis* | Bson= *B. sonorensis* | Bpum= *B. pumilus* | |
| Bmeg= *B. megaterium* | Bcl= *B. clausii* | Bcoa= *B. coagulans* | |
| Bmyc= *B. mycoides* | Banth= *B. anthracis* | Bcer= *B. cereus* | |

| Bamy= Bacillus amyloliquefaciens | Batr= B. atrophaeus | Bsub= B. subtilis | Bthu= B. thuringiensis |
|---|---|---|---|
| Blic= B. licheniformis | Bson= B. sonorensis | Bpum= B. pumilus | |
| Bmeg= B. megaterium | Bcl= B. clausii | Bcoa= B. coagulans | |
| Bmyc= B. mycoides | Banth= B. anthracis | Bcer= B. cereus | |

SEQUENCE LISTING

<160> NUMBER OF SEQ ID NOS: 35

<210> SEQ ID NO 1
<211> LENGTH: 1698
<212> TYPE: DNA
<213> ORGANISM: Bacillus subtilis
<220> FEATURE:
<221> NAME/KEY: CDS
<222> LOCATION: (1)..(1698)

<400> SEQUENCE: 1

```
agt att gac gaa gcc ctc gcc ggt tat tgt acg gat atc aat atc caa      48
Ser Ile Asp Glu Ala Leu Ala Gly Tyr Cys Thr Asp Ile Asn Ile Gln
1               5                   10                  15 atc gaa aaa gac aac agc atc acg gtg gta gat aac ggc cgc ggt att      96
Ile Glu Lys Asp Asn Ser Ile Thr Val Val Asp Asn Gly Arg Gly Ile
            20                  25                  30 cca gtt ggt att cat gaa aaa atg ggc cgg cct gcg gta gag gtc att     144
Pro Val Gly Ile His Glu Lys Met Gly Arg Pro Ala Val Glu Val Ile
        35                  40                  45 atg acg gtg ctt cat gcc gga ggg aaa ttt gac gga agc ggc tat aaa     192
Met Thr Val Leu His Ala Gly Gly Lys Phe Asp Gly Ser Gly Tyr Lys
    50                  55                  60 gta tcc gga gga ttg cac ggt gta ggt gcg tca gtc gta aac gcg ctt     240
Val Ser Gly Gly Leu His Gly Val Gly Ala Ser Val Val Asn Ala Leu
65                  70                  75                  80 tca acc gag ctt gtt gtg acg gta cac cgt gac gga aaa atc cac cgt     288
Ser Thr Glu Leu Val Val Thr Val His Arg Asp Gly Lys Ile His Arg
                85                  90                  95 caa acc tat aaa cgc gga gtt ccg gtt tca gac ctt gaa atc att ggc     336
Gln Thr Tyr Lys Arg Gly Val Pro Val Ser Asp Leu Glu Ile Ile Gly
            100                 105                 110 gaa aca gat cat tca gga acg acg aca cat ttt gtc cca gat cct gag     384
Glu Thr Asp His Ser Gly Thr Thr Thr His Phe Val Pro Asp Pro Glu
        115                 120                 125 att ttc aca gaa aca act gtg tat gat tat gat ctg ctt gct aac cgt     432
Ile Phe Thr Glu Thr Thr Val Tyr Asp Tyr Asp Leu Leu Ala Asn Arg
    130                 135                 140 gtg cgc gaa tta gcc ttt ttg aca aaa ggt gta aac atc acg att gaa     480
Val Arg Glu Leu Ala Phe Leu Thr Lys Gly Val Asn Ile Thr Ile Glu
145                 150                 155                 160 gat aaa cgt gaa gga caa gag cgc aaa aat gag tac cat tac gaa ggc     528
Asp Lys Arg Glu Gly Gln Glu Arg Lys Asn Glu Tyr His Tyr Glu Gly
```

```
                    165                 170                 175
gga att aaa agt tat gta gag tat tta aac cgt tct aaa gaa gtt gtc     576
Gly Ile Lys Ser Tyr Val Glu Tyr Leu Asn Arg Ser Lys Glu Val Val
            180                 185                 190 cat gaa gag ccg att tac att gaa ggc gaa aag gac ggc att acg gtt     624
His Glu Glu Pro Ile Tyr Ile Glu Gly Glu Lys Asp Gly Ile Thr Val
            195                 200                 205 gaa gtg gct ttg caa tat aat gac agc tac aca agc aac att tac tcg     672
Glu Val Ala Leu Gln Tyr Asn Asp Ser Tyr Thr Ser Asn Ile Tyr Ser
        210                 215                 220 ttt aca aat aac att aac acg tat gaa ggc ggg acc cac gaa gca ggc     720
Phe Thr Asn Asn Ile Asn Thr Tyr Glu Gly Gly Thr His Glu Ala Gly
225                 230                 235                 240 ttc aaa acg ggc ctg act cgt gtg atc aat gat tac gcc aga aaa aaa     768
Phe Lys Thr Gly Leu Thr Arg Val Ile Asn Asp Tyr Ala Arg Lys Lys
                245                 250                 255 ggg ctc att aaa gaa aat gat ccg aac tta agc ggt gac gac gta aga     816
Gly Leu Ile Lys Glu Asn Asp Pro Asn Leu Ser Gly Asp Asp Val Arg
            260                 265                 270 gaa ggg ctg acc gcg att att tcc atc aaa cac cct gat ccg cag ttt     864
Glu Gly Leu Thr Ala Ile Ile Ser Ile Lys His Pro Asp Pro Gln Phe
        275                 280                 285 gaa ggc caa acg aaa aca aaa cta ggc aac tcg gaa gcg cgg acg atc     912
Glu Gly Gln Thr Lys Thr Lys Leu Gly Asn Ser Glu Ala Arg Thr Ile
    290                 295                 300 acc gat acg tta ttt tct gcg gca ttg gaa aca ttt atg ctg gaa aat     960
Thr Asp Thr Leu Phe Ser Ala Ala Leu Glu Thr Phe Met Leu Glu Asn
305                 310                 315                 320 cca gat gcg gcc aaa aaa att gtc gac aaa ggt ttg atg gcg gca aga    1008
Pro Asp Ala Ala Lys Lys Ile Val Asp Lys Gly Leu Met Ala Ala Arg
                325                 330                 335 gca aga atg gct gcg aaa aaa gcg cgt gaa tta aca cgc cgc aag agt    1056
Ala Arg Met Ala Ala Lys Lys Ala Arg Glu Leu Thr Arg Arg Lys Ser
            340                 345                 350 gct ttg gaa att tca aac ctt ccc ggt aag cta gcg gac tgc tca tca    1104
Ala Leu Glu Ile Ser Asn Leu Pro Gly Lys Leu Ala Asp Cys Ser Ser
        355                 360                 365 aaa gat ccg agc att tcc gag tta tat atc gta gag ggt gac tct gcc    1152
Lys Asp Pro Ser Ile Ser Glu Leu Tyr Ile Val Glu Gly Asp Ser Ala
    370                 375                 380 gga gga tca gct aaa caa ggc cgc gac aga cat ttc caa gcc att ttg    1200
Gly Gly Ser Ala Lys Gln Gly Arg Asp Arg His Phe Gln Ala Ile Leu
385                 390                 395                 400 ccg ctt aga ggt aaa atc tta aac gtt gaa aaa gcg aga ttg gac aaa    1248
Pro Leu Arg Gly Lys Ile Leu Asn Val Glu Lys Ala Arg Leu Asp Lys
                405                 410                 415 atc ctt tcc aac aac gaa gtt cgt tct atg atc aca gca ctc gga aca    1296
Ile Leu Ser Asn Asn Glu Val Arg Ser Met Ile Thr Ala Leu Gly Thr
            420                 425                 430 ggt ata ggg gaa gat ttc aac ttg ggg aaa gcc cgt tac cat aaa gtt    1344
Gly Ile Gly Glu Asp Phe Asn Leu Gly Lys Ala Arg Tyr His Lys Val
        435                 440                 445 gtc att atg act gat gcc gac gtt gac ggc gcg cac atc aga aca ctg    1392
Val Ile Met Thr Asp Ala Asp Val Asp Gly Ala His Ile Arg Thr Leu
    450                 455                 460 ctg tta acg ttc ttt tac aga tat atg cgc caa att att gaa aat ggc    1440
Leu Leu Thr Phe Phe Tyr Arg Tyr Met Arg Gln Ile Ile Glu Asn Gly
465                 470                 475                 480 tac gtg tat att gcg cag ccg ccg ctc tac aag gtt caa cag gga aaa    1488
```

-continued

```
Tyr Val Tyr Ile Ala Gln Pro Pro Leu Tyr Lys Val Gln Gln Gly Lys
                485                 490                 495 cgt gtt gaa tat gca tat aat gac aaa gaa ctt gat gat ctg ttg aaa       1536
Arg Val Glu Tyr Ala Tyr Asn Asp Lys Glu Leu Asp Asp Leu Leu Lys
            500                 505                 510 act ctt cct caa acg cct aag cct ggc ttg cag cgt tat aaa ggt ctt       1584
Thr Leu Pro Gln Thr Pro Lys Pro Gly Leu Gln Arg Tyr Lys Gly Leu
        515                 520                 525 gga gaa atg aat gcg acc cag cta tgg gag aca acc atg gat ccg agc       1632
Gly Glu Met Asn Ala Thr Gln Leu Trp Glu Thr Thr Met Asp Pro Ser
    530                 535                 540 tcc aga aca ctt ctt cag gta act ctt gaa gat gca atg gat gcc gat       1680
Ser Arg Thr Leu Leu Gln Val Thr Leu Glu Asp Ala Met Asp Ala Asp
545                 550                 555                 560 gag aca ttt gaa atg ctg                                                1698
Glu Thr Phe Glu Met Leu
                565

<210> SEQ ID NO 2
<211> LENGTH: 566
<212> TYPE: PRT
<213> ORGANISM: Bacillus subtilis

<400> SEQUENCE: 2

Ser Ile Asp Glu Ala Leu Ala Gly Tyr Cys Thr Asp Ile Asn Ile Gln
1               5                   10                  15

Ile Glu Lys Asp Asn Ser Ile Thr Val Val Asp Asn Gly Arg Gly Ile
            20                  25                  30

Pro Val Gly Ile His Glu Lys Met Gly Arg Pro Ala Val Glu Val Ile
        35                  40                  45

Met Thr Val Leu His Ala Gly Gly Lys Phe Asp Gly Ser Gly Tyr Lys
    50                  55                  60

Val Ser Gly Gly Leu His Gly Val Gly Ala Ser Val Val Asn Ala Leu
65                  70                  75                  80

Ser Thr Glu Leu Val Val Thr Val His Arg Asp Gly Lys Ile His Arg
                85                  90                  95

Gln Thr Tyr Lys Arg Gly Val Pro Val Ser Asp Leu Glu Ile Ile Gly
            100                 105                 110

Glu Thr Asp His Ser Gly Thr Thr Thr His Phe Val Pro Asp Pro Glu
        115                 120                 125

Ile Phe Thr Glu Thr Thr Val Tyr Asp Tyr Asp Leu Leu Ala Asn Arg
    130                 135                 140

Val Arg Glu Leu Ala Phe Leu Thr Lys Gly Val Asn Ile Thr Ile Glu
145                 150                 155                 160

Asp Lys Arg Glu Gly Gln Glu Arg Lys Asn Glu Tyr His Tyr Glu Gly
                165                 170                 175

Gly Ile Lys Ser Tyr Val Glu Tyr Leu Asn Arg Ser Lys Glu Val Val
            180                 185                 190

His Glu Glu Pro Ile Tyr Ile Glu Gly Glu Lys Asp Gly Ile Thr Val
        195                 200                 205

Glu Val Ala Leu Gln Tyr Asn Asp Ser Tyr Thr Ser Asn Ile Tyr Ser
    210                 215                 220

Phe Thr Asn Asn Ile Asn Thr Tyr Glu Gly Gly Thr His Glu Ala Gly
225                 230                 235                 240

Phe Lys Thr Gly Leu Thr Arg Val Ile Asn Asp Tyr Ala Arg Lys Lys
                245                 250                 255
```

```
Gly Leu Ile Lys Glu Asn Asp Pro Asn Leu Ser Gly Asp Val Arg
              260                 265                 270

Glu Gly Leu Thr Ala Ile Ile Ser Ile Lys His Pro Asp Pro Gln Phe
        275                 280                 285

Glu Gly Gln Thr Lys Thr Lys Leu Gly Asn Ser Glu Ala Arg Thr Ile
        290                 295                 300

Thr Asp Thr Leu Phe Ser Ala Ala Leu Glu Thr Phe Met Leu Glu Asn
305                 310                 315                 320

Pro Asp Ala Ala Lys Lys Ile Val Asp Lys Gly Leu Met Ala Ala Arg
                325                 330                 335

Ala Arg Met Ala Ala Lys Lys Ala Arg Glu Leu Thr Arg Arg Lys Ser
            340                 345                 350

Ala Leu Glu Ile Ser Asn Leu Pro Gly Lys Leu Ala Asp Cys Ser Ser
        355                 360                 365

Lys Asp Pro Ser Ile Ser Glu Leu Tyr Ile Val Glu Gly Asp Ser Ala
    370                 375                 380

Gly Gly Ser Ala Lys Gln Gly Arg Asp Arg His Phe Gln Ala Ile Leu
385                 390                 395                 400

Pro Leu Arg Gly Lys Ile Leu Asn Val Glu Lys Ala Arg Leu Asp Lys
                405                 410                 415

Ile Leu Ser Asn Asn Glu Val Arg Ser Met Ile Thr Ala Leu Gly Thr
            420                 425                 430

Gly Ile Gly Glu Asp Phe Asn Leu Gly Lys Ala Arg Tyr His Lys Val
        435                 440                 445

Val Ile Met Thr Asp Ala Asp Val Asp Gly Ala His Ile Arg Thr Leu
    450                 455                 460

Leu Leu Thr Phe Phe Tyr Arg Tyr Met Arg Gln Ile Ile Glu Asn Gly
465                 470                 475                 480

Tyr Val Tyr Ile Ala Gln Pro Pro Leu Tyr Lys Val Gln Gly Lys
                485                 490                 495

Arg Val Glu Tyr Ala Tyr Asn Asp Lys Glu Leu Asp Asp Leu Leu Lys
            500                 505                 510

Thr Leu Pro Gln Thr Pro Lys Pro Gly Leu Gln Arg Tyr Lys Gly Leu
        515                 520                 525

Gly Glu Met Asn Ala Thr Gln Leu Trp Glu Thr Met Asp Pro Ser
    530                 535                 540

Ser Arg Thr Leu Leu Gln Val Thr Leu Glu Asp Ala Met Asp Ala Asp
545                 550                 555                 560

Glu Thr Phe Glu Met Leu
                565

<210> SEQ ID NO 3
<211> LENGTH: 3582
<212> TYPE: DNA
<213> ORGANISM: Bacillus subtilis
<220> FEATURE:
<221> NAME/KEY: CDS
<222> LOCATION: (1)..(3582)

<400> SEQUENCE: 3 ttg aca ggt caa cta gtt cag tat gga cga cac cgc cag cgc aga agc        48
Leu Thr Gly Gln Leu Val Gln Tyr Gly Arg His Arg Gln Arg Arg Ser
1               5                   10                  15 tat gct cgc att agc gaa gtg tta gaa tta cca aat ctc att gaa att        96
Tyr Ala Arg Ile Ser Glu Val Leu Glu Leu Pro Asn Leu Ile Glu Ile
                20                  25                  30
```

-continued

| | | |
|---|---|---|
| caa acc tct tct tat cag tgg ttt ctt gat gag ggt ctt aga gag atg<br>Gln Thr Ser Ser Tyr Gln Trp Phe Leu Asp Glu Gly Leu Arg Glu Met<br>           35                   40                  45 | 144 |
| ttt caa gac ata tca cca att gag gat ttc act ggt aac ctc tct ctt<br>Phe Gln Asp Ile Ser Pro Ile Glu Asp Phe Thr Gly Asn Leu Ser Leu<br>50                     55                   60 | 192 |
| gag ttc att gat tat agt tta ggt gag cct aaa tat cct gta gag gaa<br>Glu Phe Ile Asp Tyr Ser Leu Gly Glu Pro Lys Tyr Pro Val Glu Glu<br>65                     70                   75                   80 | 240 |
| tca aaa gaa cgt gat gtg act tac tca gct ccg cta aga gtg aag gtt<br>Ser Lys Glu Arg Asp Val Thr Tyr Ser Ala Pro Leu Arg Val Lys Val<br>                    85                   90                   95 | 288 |
| cgt tta att aac aaa gaa act gga gag gta aaa gac caa gat gtc ttc<br>Arg Leu Ile Asn Lys Glu Thr Gly Glu Val Lys Asp Gln Asp Val Phe<br>                 100                105                110 | 336 |
| atg ggg gat ttc ccg att atg aca gat aca ggt act ttt atc att aat<br>Met Gly Asp Phe Pro Ile Met Thr Asp Thr Gly Thr Phe Ile Ile Asn<br>                 115                120                125 | 384 |
| ggt gcg gaa cgt gta atc gtt tcc cag ctt gtt cgg tct cca agt gta<br>Gly Ala Glu Arg Val Ile Val Ser Gln Leu Val Arg Ser Pro Ser Val<br>130                   135                140 | 432 |
| tat ttc agt ggt aaa gta gac aaa aac ggt aaa aaa ggt ttt acc gca<br>Tyr Phe Ser Gly Lys Val Asp Lys Asn Gly Lys Lys Gly Phe Thr Ala<br>145                   150                155                160 | 480 |
| act gtc att cca aac cgt ggc gca tgg tta gaa tac gaa act gat gcg<br>Thr Val Ile Pro Asn Arg Gly Ala Trp Leu Glu Tyr Glu Thr Asp Ala<br>                 165                170                175 | 528 |
| aaa gat gtt gtt tat gtc cgc att gat cgc aca cgt aag ttg ccg gtt<br>Lys Asp Val Val Tyr Val Arg Ile Asp Arg Thr Arg Lys Leu Pro Val<br>                    180                185                190 | 576 |
| acg gtt ctt ttg cgt gct ctc ggc ttc ggt tcc gat caa gag att ctt<br>Thr Val Leu Leu Arg Ala Leu Gly Phe Gly Ser Asp Gln Glu Ile Leu<br>                 195                200                205 | 624 |
| gat ctc gta gga gaa aat gaa tac ctg cga aat acg ctt gat aaa gat<br>Asp Leu Val Gly Glu Asn Glu Tyr Leu Arg Asn Thr Leu Asp Lys Asp<br>     210                   215                220 | 672 |
| aac aca gaa aat agc gac aaa gct ttg ctt gaa att tac gaa cgt ctc<br>Asn Thr Glu Asn Ser Asp Lys Ala Leu Leu Glu Ile Tyr Glu Arg Leu<br>225                   230                235                240 | 720 |
| cgt cct gga gag cca cct aca gtt gaa aat gcg aaa agc ttg ctt gat<br>Arg Pro Gly Glu Pro Pro Thr Val Glu Asn Ala Lys Ser Leu Leu Asp<br>                 245                250                255 | 768 |
| tcg cgt ttc ttt gat ccg aaa cgt tac gat ctt gcc aat gta gga cgc<br>Ser Arg Phe Phe Asp Pro Lys Arg Tyr Asp Leu Ala Asn Val Gly Arg<br>                 260                265                270 | 816 |
| tat aaa att aat aaa aaa ctt cat att aag aat cgc ctc ttt aat cag<br>Tyr Lys Ile Asn Lys Lys Leu His Ile Lys Asn Arg Leu Phe Asn Gln<br>     275                   280                285 | 864 |
| aga ctt gct gaa acg ctt gtt gac cct gaa aca gga gaa atc ctt gct<br>Arg Leu Ala Glu Thr Leu Val Asp Pro Glu Thr Gly Glu Ile Leu Ala<br>290                   295                300 | 912 |
| gaa aaa ggt cag att ctt gat aga aga aca ctt gat aaa gta ctg cca<br>Glu Lys Gly Gln Ile Leu Asp Arg Arg Thr Leu Asp Lys Val Leu Pro<br>305                   310                315                320 | 960 |
| tac tta gaa agc gga atc ggt ttc aga aag ctg tat cca aat ggc ggt<br>Tyr Leu Glu Ser Gly Ile Gly Phe Arg Lys Leu Tyr Pro Asn Gly Gly<br>                 325                330                335 | 1008 |
| gtt gtt gaa gat gaa gta act ctt caa tcg att aaa atc tat gct ccg<br>Val Val Glu Asp Glu Val Thr Leu Gln Ser Ile Lys Ile Tyr Ala Pro<br>                 340                345                350 | 1056 |

```
act gac caa gaa gga gaa cag gtt atc aat gta atc ggc aat gct tac    1104
Thr Asp Gln Glu Gly Glu Gln Val Ile Asn Val Ile Gly Asn Ala Tyr
            355                 360                 365 att gaa gaa gag att aaa aac att acg cct gct gat att att tcc tct    1152
Ile Glu Glu Glu Ile Lys Asn Ile Thr Pro Ala Asp Ile Ile Ser Ser
        370                 375                 380 atc agc tac ttc ttc aac ctg ctg cac gga gta ggc gat aca gat gat    1200
Ile Ser Tyr Phe Phe Asn Leu Leu His Gly Val Gly Asp Thr Asp Asp
385                 390                 395                 400 atc gat cat ctt gga aac cgc cgt tta cgt tct gta ggt gaa ctt ctc    1248
Ile Asp His Leu Gly Asn Arg Arg Leu Arg Ser Val Gly Glu Leu Leu
                405                 410                 415 cag aac caa ttc cgt atc ggg tta agc cgt atg gag cgt gtg gtt cgt    1296
Gln Asn Gln Phe Arg Ile Gly Leu Ser Arg Met Glu Arg Val Val Arg
            420                 425                 430 gag aga atg tca att caa gat acg aat aca att acg cct cag cag ttg    1344
Glu Arg Met Ser Ile Gln Asp Thr Asn Thr Ile Thr Pro Gln Gln Leu
        435                 440                 445 atc aat att cgt cct gtt att gcg tcc att aaa gag ttc ttt gga agc    1392
Ile Asn Ile Arg Pro Val Ile Ala Ser Ile Lys Glu Phe Phe Gly Ser
450                 455                 460 tct cag ctt tcc cag ttc atg gac cag acg aac ccg ctt gct gaa tta    1440
Ser Gln Leu Ser Gln Phe Met Asp Gln Thr Asn Pro Leu Ala Glu Leu
465                 470                 475                 480 acg cat aag cgt cgt ctg tca gca tta gga cca ggc gga ttg aca cgt    1488
Thr His Lys Arg Arg Leu Ser Ala Leu Gly Pro Gly Gly Leu Thr Arg
                485                 490                 495 gaa cgt gcc gga atg gaa gtg cgt gac gtt cac tac tcc cac tat ggc    1536
Glu Arg Ala Gly Met Glu Val Arg Asp Val His Tyr Ser His Tyr Gly
            500                 505                 510 cgt atg tgt ccg att gaa aca cct gag ggt cca aac atc ggt ttg atc    1584
Arg Met Cys Pro Ile Glu Thr Pro Glu Gly Pro Asn Ile Gly Leu Ile
        515                 520                 525 aac tcg ctt tca tct tat gca aaa gta aac cgt ttt ggt ttc atc gaa    1632
Asn Ser Leu Ser Ser Tyr Ala Lys Val Asn Arg Phe Gly Phe Ile Glu
530                 535                 540 acg cct tat cgc cgt gtt gac cct gaa aca ggg aag gta acg ggc aga    1680
Thr Pro Tyr Arg Arg Val Asp Pro Glu Thr Gly Lys Val Thr Gly Arg
545                 550                 555                 560 atc gat tac tta act gct gat gaa gag gat aac tat gtt gtc gct cag    1728
Ile Asp Tyr Leu Thr Ala Asp Glu Glu Asp Asn Tyr Val Val Ala Gln
                565                 570                 575 gcg aac gct cgt ctt gat gac gat ggc tca ttt att gat gac agc att    1776
Ala Asn Ala Arg Leu Asp Asp Asp Gly Ser Phe Ile Asp Asp Ser Ile
            580                 585                 590 atc gcc cgt ttc cgc ggg gag aac acc gtt gtt tcc aga aac cgt gtg    1824
Ile Ala Arg Phe Arg Gly Glu Asn Thr Val Val Ser Arg Asn Arg Val
        595                 600                 605 gat tac atg gat gta tca cct aag cag gtt gtt tct gct gcg aca gca    1872
Asp Tyr Met Asp Val Ser Pro Lys Gln Val Val Ser Ala Ala Thr Ala
610                 615                 620 tgt atc ccg ttc cta gaa aac gat gac tcc aac cgt gcc ctc atg gga    1920
Cys Ile Pro Phe Leu Glu Asn Asp Asp Ser Asn Arg Ala Leu Met Gly
625                 630                 635                 640 gca aac atg caa cgt cag gct gtg cct ttg atg cag ccg gaa gcg ccg    1968
Ala Asn Met Gln Arg Gln Ala Val Pro Leu Met Gln Pro Glu Ala Pro
                645                 650                 655 ttc gtt gga act ggt atg gaa tat gta tca ggt aaa gac tct ggt gcc    2016
Phe Val Gly Thr Gly Met Glu Tyr Val Ser Gly Lys Asp Ser Gly Ala
```

-continued

|  |  |  |  |  |  |  |  |  |  |  |  |  |  |  |  |
|---|---|---|---|---|---|---|---|---|---|---|---|---|---|---|---|
|  |  | 660 |  |  |  | 665 |  |  |  | 670 |  |  |  |  |  |
| gct | gtt | att | tgt | aaa | cac | cct | ggt | atc | gtt | gaa | cgc | gta | gaa | gcg | aag | 2064 |
| Ala | Val | Ile | Cys | Lys | His | Pro | Gly | Ile | Val | Glu | Arg | Val | Glu | Ala | Lys |
|  |  | 675 |  |  |  | 680 |  |  |  | 685 |  |  |  |  |  |
| aac | gtt | tgg | gtt | cgc | cgt | tat | gaa | gaa | gta | gat | ggt | caa | aaa | gta | aaa | 2112 |
| Asn | Val | Trp | Val | Arg | Arg | Tyr | Glu | Glu | Val | Asp | Gly | Gln | Lys | Val | Lys |
|  |  | 690 |  |  |  | 695 |  |  |  | 700 |  |  |  |  |  |
| ggg | aac | ctg | gat | aaa | tac | agc | atg | ctg | aaa | ttt | gtc | cgc | tcc | aac | caa | 2160 |
| Gly | Asn | Leu | Asp | Lys | Tyr | Ser | Met | Leu | Lys | Phe | Val | Arg | Ser | Asn | Gln |
| 705 |  |  |  | 710 |  |  |  | 715 |  |  |  | 720 |  |  |  |
| ggt | act | tgc | tac | aat | caa | cgt | ccg | atc | gta | agt | gtc | ggc | gat | gaa | gtg | 2208 |
| Gly | Thr | Cys | Tyr | Asn | Gln | Arg | Pro | Ile | Val | Ser | Val | Gly | Asp | Glu | Val |
|  |  |  |  | 725 |  |  |  | 730 |  |  |  | 735 |  |  |  |
| gta | aaa | gga | gaa | atc | ctt | gct | gac | ggt | cct | tct | atg | gag | ctt | ggt | gaa | 2256 |
| Val | Lys | Gly | Glu | Ile | Leu | Ala | Asp | Gly | Pro | Ser | Met | Glu | Leu | Gly | Glu |
|  |  | 740 |  |  |  | 745 |  |  |  | 750 |  |  |  |  |  |
| ctt | gca | ctt | ggc | cgt | aac | gta | atg | gtt | ggc | ttc | atg | act | tgg | gat | ggc | 2304 |
| Leu | Ala | Leu | Gly | Arg | Asn | Val | Met | Val | Gly | Phe | Met | Thr | Trp | Asp | Gly |
|  |  | 755 |  |  |  | 760 |  |  |  | 765 |  |  |  |  |  |
| tac | aac | tat | gag | gat | gcc | atc | atc | atg | agt | gaa | cgc | ctt | gtg | aag | gat | 2352 |
| Tyr | Asn | Tyr | Glu | Asp | Ala | Ile | Ile | Met | Ser | Glu | Arg | Leu | Val | Lys | Asp |
|  | 770 |  |  |  | 775 |  |  |  | 780 |  |  |  |  |  |  |
| gat | gtt | tat | aca | tct | atc | cac | att | gaa | gaa | tat | gaa | tca | gaa | gca | cgc | 2400 |
| Asp | Val | Tyr | Thr | Ser | Ile | His | Ile | Glu | Glu | Tyr | Glu | Ser | Glu | Ala | Arg |
| 785 |  |  |  | 790 |  |  |  | 795 |  |  |  | 800 |  |  |  |
| gat | acg | aaa | ctt | gga | cct | gaa | gaa | atc | act | cgc | gat | att | cca | aac | gtc | 2448 |
| Asp | Thr | Lys | Leu | Gly | Pro | Glu | Glu | Ile | Thr | Arg | Asp | Ile | Pro | Asn | Val |
|  |  |  |  | 805 |  |  |  | 810 |  |  |  | 815 |  |  |  |
| ggt | gaa | gat | gcg | ctt | cgc | aat | ctt | gat | gac | cgc | gga | atc | atc | cgt | att | 2496 |
| Gly | Glu | Asp | Ala | Leu | Arg | Asn | Leu | Asp | Asp | Arg | Gly | Ile | Ile | Arg | Ile |
|  |  | 820 |  |  |  | 825 |  |  |  | 830 |  |  |  |  |  |
| ggg | gca | gaa | gtg | aaa | gac | gga | gat | ctt | ctt | gtt | ggt | aaa | gta | acg | cct | 2544 |
| Gly | Ala | Glu | Val | Lys | Asp | Gly | Asp | Leu | Leu | Val | Gly | Lys | Val | Thr | Pro |
|  |  | 835 |  |  |  | 840 |  |  |  | 845 |  |  |  |  |  |
| aaa | ggt | gta | act | gaa | ctg | act | gct | gaa | gaa | cgc | ctg | ctt | cac | gcc | atc | 2592 |
| Lys | Gly | Val | Thr | Glu | Leu | Thr | Ala | Glu | Glu | Arg | Leu | Leu | His | Ala | Ile |
|  | 850 |  |  |  | 855 |  |  |  | 860 |  |  |  |  |  |  |
| ttt | ggt | gaa | aag | gcc | cgc | gag | gtt | cgt | gat | act | tct | ctt | cgt | gtg | cct | 2640 |
| Phe | Gly | Glu | Lys | Ala | Arg | Glu | Val | Arg | Asp | Thr | Ser | Leu | Arg | Val | Pro |
| 865 |  |  |  | 870 |  |  |  | 875 |  |  |  | 880 |  |  |  |
| cac | ggc | ggc | ggc | gga | att | atc | cac | gac | gtt | aaa | gtc | ttc | aat | cgt | gaa | 2688 |
| His | Gly | Gly | Gly | Gly | Ile | Ile | His | Asp | Val | Lys | Val | Phe | Asn | Arg | Glu |
|  |  |  |  | 885 |  |  |  | 890 |  |  |  | 895 |  |  |  |
| gac | gga | gat | gaa | ctt | cct | cca | ggc | gtt | aac | cag | ttg | gta | cgt | gtg | tat | 2736 |
| Asp | Gly | Asp | Glu | Leu | Pro | Pro | Gly | Val | Asn | Gln | Leu | Val | Arg | Val | Tyr |
|  |  | 900 |  |  |  | 905 |  |  |  | 910 |  |  |  |  |  |
| atc | gtt | cag | aaa | cgt | aag | att | tct | gaa | ggg | gat | aaa | atg | gcc | ggt | cgt | 2784 |
| Ile | Val | Gln | Lys | Arg | Lys | Ile | Ser | Glu | Gly | Asp | Lys | Met | Ala | Gly | Arg |
|  |  | 915 |  |  |  | 920 |  |  |  | 925 |  |  |  |  |  |
| cac | ggt | aac | aaa | ggt | gtt | atc | tct | aag | att | ctt | cct | gaa | gag | gat | atg | 2832 |
| His | Gly | Asn | Lys | Gly | Val | Ile | Ser | Lys | Ile | Leu | Pro | Glu | Glu | Asp | Met |
|  |  | 930 |  |  |  | 935 |  |  |  | 940 |  |  |  |  |  |
| cct | tac | ctt | cct | gac | ggc | aca | cca | att | gat | atc | atg | ctt | aac | ccg | ctg | 2880 |
| Pro | Tyr | Leu | Pro | Asp | Gly | Thr | Pro | Ile | Asp | Ile | Met | Leu | Asn | Pro | Leu |
| 945 |  |  |  | 950 |  |  |  | 955 |  |  |  | 960 |  |  |  |
| ggc | gta | cca | tca | cgt | atg | aac | atc | ggg | cag | gta | ttg | gag | ctc | cat | atg | 2928 |
| Gly | Val | Pro | Ser | Arg | Met | Asn | Ile | Gly | Gln | Val | Leu | Glu | Leu | His | Met |
|  |  | 965 |  |  |  | 970 |  |  |  | 975 |  |  |  |  |  |
| ggt | atg | gcc | gct | cgt | tat | ctc | ggc | atc | cac | att | gcg | tca | ccg | gta | ttt | 2976 |

```
                Gly Met Ala Ala Arg Tyr Leu Gly Ile His Ile Ala Ser Pro Val Phe
                            980                 985                 990 gac gga gcg cgt gaa gag gat gtt tgg gaa aca ctt gaa gaa gcc gga       3024
Asp Gly Ala Arg Glu Glu Asp Val Trp Glu Thr Leu Glu Glu Ala Gly
            995                1000                1005 atg tct cgt gac gcc aaa acg gtt ctt tac gac ggg cgt agc gga           3069
Met Ser Arg Asp Ala Lys Thr Val Leu Tyr Asp Gly Arg Ser Gly
    1010                1015                1020 gag ccg ttt gat aac cgt gta tct gtt ggt att atg tac atg att           3114
Glu Pro Phe Asp Asn Arg Val Ser Val Gly Ile Met Tyr Met Ile
        1025                1030                1035 aaa ctg gct cac atg gtt gac gat aaa ctt cat gcg cgc tct aca           3159
Lys Leu Ala His Met Val Asp Asp Lys Leu His Ala Arg Ser Thr
    1040                1045                1050 ggc cct tac tca ctt gtt acg cag cag cct ctt ggc ggt aaa gcg           3204
Gly Pro Tyr Ser Leu Val Thr Gln Gln Pro Leu Gly Gly Lys Ala
    1055                1060                1065 caa ttt ggc gga cag cgt ttt ggt gag atg gag gtt tgg gca ctt           3249
Gln Phe Gly Gly Gln Arg Phe Gly Glu Met Glu Val Trp Ala Leu
    1070                1075                1080 gaa gct tac ggt gcg gct tac act ctt caa gaa att ctg act gtt           3294
Glu Ala Tyr Gly Ala Ala Tyr Thr Leu Gln Glu Ile Leu Thr Val
    1085                1090                1095 aaa tct gat gac gtg gtt gga cgt gtg aaa aca tac gaa gcc atc           3339
Lys Ser Asp Asp Val Val Gly Arg Val Lys Thr Tyr Glu Ala Ile
    1100                1105                1110 gtt aaa ggc gac aac gtt cct gaa cca ggt gtt ccg gaa tca ttc           3384
Val Lys Gly Asp Asn Val Pro Glu Pro Gly Val Pro Glu Ser Phe
    1115                1120                1125 aaa gta tta atc aag gaa ctt caa agc tta ggt atg gat gtc aaa           3429
Lys Val Leu Ile Lys Glu Leu Gln Ser Leu Gly Met Asp Val Lys
    1130                1135                1140 atc ctt tct ggt gat gaa gaa gaa ata gaa atg aga gat tta gaa           3474
Ile Leu Ser Gly Asp Glu Glu Glu Ile Glu Met Arg Asp Leu Glu
    1145                1150                1155 gac gaa gaa gat gca aaa caa gct gac ggc ctg gcg tta tca ggt           3519
Asp Glu Glu Asp Ala Lys Gln Ala Asp Gly Leu Ala Leu Ser Gly
    1160                1165                1170 gat gaa gag ccg gag gaa aca gca tct gca gac gtt gaa cga gat           3564
Asp Glu Glu Pro Glu Glu Thr Ala Ser Ala Asp Val Glu Arg Asp
    1175                1180                1185 gta gta aca aaa gaa taa                                               3582
Val Val Thr Lys Glu
    1190

<210> SEQ ID NO 4
<211> LENGTH: 1193
<212> TYPE: PRT
<213> ORGANISM: Bacillus subtilis

<400> SEQUENCE: 4

Leu Thr Gly Gln Leu Val Gln Tyr Gly Arg His Arg Gln Arg Arg Ser
1               5                   10                  15

Tyr Ala Arg Ile Ser Glu Val Leu Glu Leu Pro Asn Leu Ile Glu Ile
            20                  25                  30

Gln Thr Ser Ser Tyr Gln Trp Phe Leu Asp Glu Gly Leu Arg Glu Met
        35                  40                  45

Phe Gln Asp Ile Ser Pro Ile Glu Asp Phe Thr Gly Asn Leu Ser Leu
    50                  55                  60
```

-continued

```
Glu Phe Ile Asp Tyr Ser Leu Gly Glu Pro Lys Tyr Pro Val Glu
 65                  70                  75                  80

Ser Lys Glu Arg Asp Val Thr Tyr Ser Ala Pro Leu Arg Val Lys Val
             85                  90                  95

Arg Leu Ile Asn Lys Glu Thr Gly Glu Val Lys Asp Gln Asp Val Phe
            100                 105                 110

Met Gly Asp Phe Pro Ile Met Thr Asp Thr Gly Thr Phe Ile Ile Asn
            115                 120                 125

Gly Ala Glu Arg Val Ile Val Ser Gln Leu Val Arg Ser Pro Ser Val
        130                 135                 140

Tyr Phe Ser Gly Lys Val Asp Lys Asn Gly Lys Lys Gly Phe Thr Ala
145                 150                 155                 160

Thr Val Ile Pro Asn Arg Gly Ala Trp Leu Glu Tyr Glu Thr Asp Ala
                165                 170                 175

Lys Asp Val Val Tyr Val Arg Ile Asp Arg Thr Arg Lys Leu Pro Val
            180                 185                 190

Thr Val Leu Leu Arg Ala Leu Gly Phe Gly Ser Asp Gln Glu Ile Leu
        195                 200                 205

Asp Leu Val Gly Glu Asn Glu Tyr Leu Arg Asn Thr Leu Asp Lys Asp
    210                 215                 220

Asn Thr Glu Asn Ser Asp Lys Ala Leu Leu Glu Ile Tyr Glu Arg Leu
225                 230                 235                 240

Arg Pro Gly Glu Pro Pro Thr Val Glu Asn Ala Lys Ser Leu Leu Asp
                245                 250                 255

Ser Arg Phe Phe Asp Pro Lys Arg Tyr Asp Leu Ala Asn Val Gly Arg
            260                 265                 270

Tyr Lys Ile Asn Lys Lys Leu His Ile Lys Asn Arg Leu Phe Asn Gln
        275                 280                 285

Arg Leu Ala Glu Thr Leu Val Asp Pro Glu Thr Gly Glu Ile Leu Ala
    290                 295                 300

Glu Lys Gly Gln Ile Leu Asp Arg Arg Thr Leu Asp Lys Val Leu Pro
305                 310                 315                 320

Tyr Leu Glu Ser Gly Ile Gly Phe Arg Lys Leu Tyr Pro Asn Gly Gly
                325                 330                 335

Val Val Glu Asp Glu Val Thr Leu Gln Ser Ile Lys Ile Tyr Ala Pro
            340                 345                 350

Thr Asp Gln Glu Gly Glu Gln Val Ile Asn Val Ile Gly Asn Ala Tyr
        355                 360                 365

Ile Glu Glu Glu Ile Lys Asn Ile Thr Pro Ala Asp Ile Ile Ser Ser
    370                 375                 380

Ile Ser Tyr Phe Phe Asn Leu Leu His Gly Val Gly Asp Thr Asp Asp
385                 390                 395                 400

Ile Asp His Leu Gly Asn Arg Arg Leu Arg Ser Val Gly Glu Leu Leu
                405                 410                 415

Gln Asn Gln Phe Arg Ile Gly Leu Ser Arg Met Glu Arg Val Val Arg
            420                 425                 430

Glu Arg Met Ser Ile Gln Asp Thr Asn Thr Ile Thr Pro Gln Gln Leu
        435                 440                 445

Ile Asn Ile Arg Pro Val Ile Ala Ser Ile Lys Glu Phe Phe Gly Ser
    450                 455                 460

Ser Gln Leu Ser Gln Phe Met Asp Gln Thr Asn Pro Leu Ala Glu Leu
465                 470                 475                 480

Thr His Lys Arg Arg Leu Ser Ala Leu Gly Pro Gly Gly Leu Thr Arg
```

```
              485                 490                 495
Glu Arg Ala Gly Met Glu Val Arg Asp Val His Tyr Ser His Tyr Gly
            500                 505                 510

Arg Met Cys Pro Ile Glu Thr Pro Glu Gly Pro Asn Ile Gly Leu Ile
            515                 520                 525

Asn Ser Leu Ser Ser Tyr Ala Lys Val Asn Arg Phe Gly Phe Ile Glu
            530                 535                 540

Thr Pro Tyr Arg Arg Val Asp Pro Glu Thr Gly Lys Val Thr Gly Arg
545                 550                 555                 560

Ile Asp Tyr Leu Thr Ala Asp Glu Asp Asn Tyr Val Val Ala Gln
                565                 570                 575

Ala Asn Ala Arg Leu Asp Asp Gly Ser Phe Ile Asp Asp Ser Ile
            580                 585                 590

Ile Ala Arg Phe Arg Gly Glu Asn Thr Val Val Ser Arg Asn Arg Val
            595                 600                 605

Asp Tyr Met Asp Val Ser Pro Lys Gln Val Val Ser Ala Ala Thr Ala
            610                 615                 620

Cys Ile Pro Phe Leu Glu Asn Asp Asp Ser Asn Arg Ala Leu Met Gly
625                 630                 635                 640

Ala Asn Met Gln Arg Gln Ala Val Pro Leu Met Gln Pro Glu Ala Pro
                645                 650                 655

Phe Val Gly Thr Gly Met Glu Tyr Val Ser Gly Lys Asp Ser Gly Ala
            660                 665                 670

Ala Val Ile Cys Lys His Pro Gly Ile Val Glu Arg Val Glu Ala Lys
            675                 680                 685

Asn Val Trp Val Arg Arg Tyr Glu Glu Val Asp Gly Gln Lys Val Lys
            690                 695                 700

Gly Asn Leu Asp Lys Tyr Ser Met Leu Lys Phe Val Arg Ser Asn Gln
705                 710                 715                 720

Gly Thr Cys Tyr Asn Gln Arg Pro Ile Val Ser Val Gly Asp Glu Val
                725                 730                 735

Val Lys Gly Glu Ile Leu Ala Asp Gly Pro Ser Met Glu Leu Gly Glu
            740                 745                 750

Leu Ala Leu Gly Arg Asn Val Met Val Gly Phe Met Thr Trp Asp Gly
            755                 760                 765

Tyr Asn Tyr Glu Asp Ala Ile Ile Met Ser Glu Arg Leu Val Lys Asp
            770                 775                 780

Asp Val Tyr Thr Ser Ile His Ile Glu Glu Tyr Glu Ser Glu Ala Arg
785                 790                 795                 800

Asp Thr Lys Leu Gly Pro Glu Glu Ile Thr Arg Asp Ile Pro Asn Val
                805                 810                 815

Gly Glu Asp Ala Leu Arg Asn Leu Asp Asp Arg Gly Ile Ile Arg Ile
            820                 825                 830

Gly Ala Glu Val Lys Asp Gly Asp Leu Leu Val Gly Lys Val Thr Pro
            835                 840                 845

Lys Gly Val Thr Glu Leu Thr Ala Glu Glu Arg Leu Leu His Ala Ile
            850                 855                 860

Phe Gly Glu Lys Ala Arg Glu Val Arg Asp Thr Ser Leu Arg Val Pro
865                 870                 875                 880

His Gly Gly Gly Gly Ile Ile His Asp Val Lys Val Phe Asn Arg Glu
                885                 890                 895

Asp Gly Asp Glu Leu Pro Pro Gly Val Asn Gln Leu Val Arg Val Tyr
            900                 905                 910
```

```
Ile Val Gln Lys Arg Lys Ile Ser Glu Gly Asp Lys Met Ala Gly Arg
        915                 920                 925

His Gly Asn Lys Gly Val Ile Ser Lys Ile Leu Pro Glu Glu Asp Met
        930                 935                 940

Pro Tyr Leu Pro Asp Gly Thr Pro Ile Asp Ile Met Leu Asn Pro Leu
945                 950                 955                 960

Gly Val Pro Ser Arg Met Asn Ile Gly Gln Val Leu Glu Leu His Met
                965                 970                 975

Gly Met Ala Ala Arg Tyr Leu Gly Ile His Ile Ala Ser Pro Val Phe
            980                 985                 990

Asp Gly Ala Arg Glu Glu Asp Val Trp Glu Thr Leu Glu Glu Ala Gly
        995                 1000                1005

Met Ser Arg Asp Ala Lys Thr Val Leu Tyr Asp Gly Arg Ser Gly
        1010                1015                1020

Glu Pro Phe Asp Asn Arg Val Ser Val Gly Ile Met Tyr Met Ile
        1025                1030                1035

Lys Leu Ala His Met Val Asp Asp Lys Leu His Ala Arg Ser Thr
        1040                1045                1050

Gly Pro Tyr Ser Leu Val Thr Gln Gln Pro Leu Gly Gly Lys Ala
        1055                1060                1065

Gln Phe Gly Gly Gln Arg Phe Gly Glu Met Glu Val Trp Ala Leu
        1070                1075                1080

Glu Ala Tyr Gly Ala Ala Tyr Thr Leu Gln Glu Ile Leu Thr Val
        1085                1090                1095

Lys Ser Asp Asp Val Val Gly Arg Val Lys Thr Tyr Glu Ala Ile
        1100                1105                1110

Val Lys Gly Asp Asn Val Pro Glu Pro Gly Val Pro Glu Ser Phe
        1115                1120                1125

Lys Val Leu Ile Lys Glu Leu Gln Ser Leu Gly Met Asp Val Lys
        1130                1135                1140

Ile Leu Ser Gly Asp Glu Glu Ile Glu Met Arg Asp Leu Glu
        1145                1150                1155

Asp Glu Glu Asp Ala Lys Gln Ala Asp Gly Leu Ala Leu Ser Gly
        1160                1165                1170

Asp Glu Glu Pro Glu Glu Thr Ala Ser Ala Asp Val Glu Arg Asp
        1175                1180                1185

Val Val Thr Lys Glu
        1190

<210> SEQ ID NO 5
<211> LENGTH: 1548
<212> TYPE: DNA
<213> ORGANISM: Bacillus subtilis
<220> FEATURE:
<221> NAME/KEY: CDS
<222> LOCATION: (1)..(1548)

<400> SEQUENCE: 5 tat gca atg agc gtt att gtg tcc cgt gct ctt cca gat gta cgt gac      48
Tyr Ala Met Ser Val Ile Val Ser Arg Ala Leu Pro Asp Val Arg Asp
1               5                   10                  15 ggt tta aaa ccg gtt cac aga cgg att ttg tat gca atg aat gat ttg      96
Gly Leu Lys Pro Val His Arg Arg Ile Leu Tyr Ala Met Asn Asp Leu
            20                  25                  30 ggc atg acg agt gac aag cca tat aaa aaa tcc gcg cgt atc gtc gga     144
Gly Met Thr Ser Asp Lys Pro Tyr Lys Lys Ser Ala Arg Ile Val Gly
        35                  40                  45
```

-continued

```
             35                  40                  45
gaa gtt atc ggg aaa tac cac ccg cac ggt gat tca gcg gta tat gaa     192
Glu Val Ile Gly Lys Tyr His Pro His Gly Asp Ser Ala Val Tyr Glu
     50                  55                  60 tcc atg gtc aga atg gcg cag gat ttt aac tac cgt tac atg ctc gtt     240
Ser Met Val Arg Met Ala Gln Asp Phe Asn Tyr Arg Tyr Met Leu Val
 65                  70                  75                  80 gac ggt cac ggg aac ttc ggt tct gtt gac gga gac tca gcg gct gcc     288
Asp Gly His Gly Asn Phe Gly Ser Val Asp Gly Asp Ser Ala Ala Ala
                 85                  90                  95 atg cgt tat aca gaa gca aga atg tct aag atc tcg atg gaa att ctt     336
Met Arg Tyr Thr Glu Ala Arg Met Ser Lys Ile Ser Met Glu Ile Leu
            100                 105                 110 cga gat atc aca aaa gac aca atc gat tat cag gac aac tat gat ggg     384
Arg Asp Ile Thr Lys Asp Thr Ile Asp Tyr Gln Asp Asn Tyr Asp Gly
        115                 120                 125 tca gaa aga gaa ccc gtc gtt atg cct tca agg ttc ccg aat ctg ctc     432
Ser Glu Arg Glu Pro Val Val Met Pro Ser Arg Phe Pro Asn Leu Leu
    130                 135                 140 gtg aac ggt gct gcc ggt att gcg gta ggt atg gca aca aac atc cct     480
Val Asn Gly Ala Ala Gly Ile Ala Val Gly Met Ala Thr Asn Ile Pro
145                 150                 155                 160 ccg cac cag ctt ggg gaa atc att gac ggt gta ctt gct gtc agt gag     528
Pro His Gln Leu Gly Glu Ile Ile Asp Gly Val Leu Ala Val Ser Glu
                165                 170                 175 aac ccg gac att aca atc cct gag ctg atg gaa gtc att cca ggg cct     576
Asn Pro Asp Ile Thr Ile Pro Glu Leu Met Glu Val Ile Pro Gly Pro
            180                 185                 190 gat ttc ccg act gcg ggt caa atc ttg gga cgc agc ggt atc cgg aaa     624
Asp Phe Pro Thr Ala Gly Gln Ile Leu Gly Arg Ser Gly Ile Arg Lys
        195                 200                 205 gca tac gaa tct ggc cga ggc tct att acg att cgg gca aaa gct gag     672
Ala Tyr Glu Ser Gly Arg Gly Ser Ile Thr Ile Arg Ala Lys Ala Glu
    210                 215                 220 atc gaa caa aca tct tca ggt aaa gaa aga att atc gtt aca gag tta     720
Ile Glu Gln Thr Ser Ser Gly Lys Glu Arg Ile Ile Val Thr Glu Leu
225                 230                 235                 240 cct tac caa gta aat aag gcg aaa tta atc gag aaa att gct gat ctc     768
Pro Tyr Gln Val Asn Lys Ala Lys Leu Ile Glu Lys Ile Ala Asp Leu
                245                 250                 255 gtt agg gac aaa aag ata gag ggc atc aca gat ctg cgt gat gag tca     816
Val Arg Asp Lys Lys Ile Glu Gly Ile Thr Asp Leu Arg Asp Glu Ser
            260                 265                 270 gat cgt aca ggt atg aga att gtc att gaa atc aga cgc gat gcc aat     864
Asp Arg Thr Gly Met Arg Ile Val Ile Glu Ile Arg Arg Asp Ala Asn
        275                 280                 285 gca aat gtt att cta aat aac cta tac aaa caa act gcg cta caa aca     912
Ala Asn Val Ile Leu Asn Asn Leu Tyr Lys Gln Thr Ala Leu Gln Thr
    290                 295                 300 tct ttt ggt atc aac ctg ctt gcg ctt gtt gac ggt cag ccg aaa gtt     960
Ser Phe Gly Ile Asn Leu Leu Ala Leu Val Asp Gly Gln Pro Lys Val
305                 310                 315                 320 tta aat cta aag caa tgc cta gag cat tac ctt gac cat caa aaa gtc    1008
Leu Asn Leu Lys Gln Cys Leu Glu His Tyr Leu Asp His Gln Lys Val
                325                 330                 335 gtc atc aga cgc cgt aca gca tat gaa ttg cgt aaa gcg gaa gcg aga    1056
Val Ile Arg Arg Arg Thr Ala Tyr Glu Leu Arg Lys Ala Glu Ala Arg
            340                 345                 350 gct cat atc ttg gaa ggt ttg aga att gct ctc gat cat ctc gat gca    1104
Ala His Ile Leu Glu Gly Leu Arg Ile Ala Leu Asp His Leu Asp Ala
```

```
                Ala His Ile Leu Glu Gly Leu Arg Ile Ala Leu Asp His Leu Asp Ala
                        355                 360                 365 gtt att tct ctt atc cgt aat tct caa acg gct gaa ata gcg aga aca        1152
Val Ile Ser Leu Ile Arg Asn Ser Gln Thr Ala Glu Ile Ala Arg Thr
370                 375                 380 ggt cta att gaa caa ttc tca ctg aca gag aag caa gca caa gcg atc        1200
Gly Leu Ile Glu Gln Phe Ser Leu Thr Glu Lys Gln Ala Gln Ala Ile
385                 390                 395                 400 ctc gat atg agg ctg cag cgt tta aca gga cta gaa cgt gaa aag atc        1248
Leu Asp Met Arg Leu Gln Arg Leu Thr Gly Leu Glu Arg Glu Lys Ile
                405                 410                 415 gaa gaa gaa tac caa tct ctt gtt aaa tta att gca gag cta aaa gac        1296
Glu Glu Glu Tyr Gln Ser Leu Val Lys Leu Ile Ala Glu Leu Lys Asp
            420                 425                 430 att ttg gca aat gaa tat aaa gtg ctt gag atc atc cgt gaa gaa ctc        1344
Ile Leu Ala Asn Glu Tyr Lys Val Leu Glu Ile Ile Arg Glu Glu Leu
        435                 440                 445 act gaa atc aaa gag cgt ttc aac gat gaa aga cgc acg gag atc gtc        1392
Thr Glu Ile Lys Glu Arg Phe Asn Asp Glu Arg Arg Thr Glu Ile Val
    450                 455                 460 act tct gga cta gaa aca att gaa gat gaa gat ctt att gag aga gaa        1440
Thr Ser Gly Leu Glu Thr Ile Glu Asp Glu Asp Leu Ile Glu Arg Glu
465                 470                 475                 480 aat atc gtc gtc act ctg aca cac aac ggg tac atc aaa cgt ctt cct        1488
Asn Ile Val Val Thr Leu Thr His Asn Gly Tyr Ile Lys Arg Leu Pro
                485                 490                 495 gca tca act tac cgc agt caa aaa cga ggc gga aaa ggt gta cag gga        1536
Ala Ser Thr Tyr Arg Ser Gln Lys Arg Gly Gly Lys Gly Val Gln Gly
            500                 505                 510 atg gga aca aac                                                        1548
Met Gly Thr Asn
        515

<210> SEQ ID NO 6
<211> LENGTH: 516
<212> TYPE: PRT
<213> ORGANISM: Bacillus subtilis

<400> SEQUENCE: 6

Tyr Ala Met Ser Val Ile Val Ser Arg Ala Leu Pro Asp Val Arg Asp
1               5                   10                  15

Gly Leu Lys Pro Val His Arg Arg Ile Leu Tyr Ala Met Asn Asp Leu
            20                  25                  30

Gly Met Thr Ser Asp Lys Pro Tyr Lys Lys Ser Ala Arg Ile Val Gly
        35                  40                  45

Glu Val Ile Gly Lys Tyr His Pro His Gly Asp Ser Ala Val Tyr Glu
    50                  55                  60

Ser Met Val Arg Met Ala Gln Asp Phe Asn Tyr Arg Tyr Met Leu Val
65                  70                  75                  80

Asp Gly His Gly Asn Phe Gly Ser Val Asp Gly Asp Ser Ala Ala Ala
                85                  90                  95

Met Arg Tyr Thr Glu Ala Arg Met Ser Lys Ile Ser Met Glu Ile Leu
            100                 105                 110

Arg Asp Ile Thr Lys Asp Thr Ile Asp Tyr Gln Asp Asn Tyr Asp Gly
        115                 120                 125

Ser Glu Arg Glu Pro Val Val Met Pro Ser Arg Phe Pro Asn Leu Leu
    130                 135                 140

Val Asn Gly Ala Ala Gly Ile Ala Val Gly Met Ala Thr Asn Ile Pro
```

145                 150                 155                 160

Pro His Gln Leu Gly Glu Ile Ile Asp Gly Val Leu Ala Val Ser Glu
                        165                 170                 175

Asn Pro Asp Ile Thr Ile Pro Glu Leu Met Glu Val Ile Pro Gly Pro
                        180                 185                 190

Asp Phe Pro Thr Ala Gly Gln Ile Leu Gly Arg Ser Gly Ile Arg Lys
                        195                 200                 205

Ala Tyr Glu Ser Gly Arg Gly Ser Ile Thr Ile Arg Ala Lys Ala Glu
                        210                 215                 220

Ile Glu Gln Thr Ser Ser Gly Lys Glu Arg Ile Ile Val Thr Glu Leu
        225                 230                 235                 240

Pro Tyr Gln Val Asn Lys Ala Lys Leu Ile Glu Lys Ile Ala Asp Leu
                        245                 250                 255

Val Arg Asp Lys Lys Ile Glu Gly Ile Thr Asp Leu Arg Asp Glu Ser
                        260                 265                 270

Asp Arg Thr Gly Met Arg Ile Val Ile Glu Ile Arg Arg Asp Ala Asn
                        275                 280                 285

Ala Asn Val Ile Leu Asn Asn Leu Tyr Lys Gln Thr Ala Leu Gln Thr
                        290                 295                 300

Ser Phe Gly Ile Asn Leu Leu Ala Leu Val Asp Gly Gln Pro Lys Val
        305                 310                 315                 320

Leu Asn Leu Lys Gln Cys Leu Glu His Tyr Leu Asp His Gln Lys Val
                        325                 330                 335

Val Ile Arg Arg Arg Thr Ala Tyr Glu Leu Arg Lys Ala Glu Ala Arg
                        340                 345                 350

Ala His Ile Leu Glu Gly Leu Arg Ile Ala Leu Asp His Leu Asp Ala
                        355                 360                 365

Val Ile Ser Leu Ile Arg Asn Ser Gln Thr Ala Glu Ile Ala Arg Thr
                        370                 375                 380

Gly Leu Ile Glu Gln Phe Ser Leu Thr Glu Lys Gln Ala Gln Ala Ile
        385                 390                 395                 400

Leu Asp Met Arg Leu Gln Arg Leu Thr Gly Leu Glu Arg Glu Lys Ile
                        405                 410                 415

Glu Glu Glu Tyr Gln Ser Leu Val Lys Leu Ile Ala Glu Leu Lys Asp
                        420                 425                 430

Ile Leu Ala Asn Glu Tyr Lys Val Leu Glu Ile Ile Arg Glu Glu Leu
                        435                 440                 445

Thr Glu Ile Lys Glu Arg Phe Asn Asp Glu Arg Arg Thr Glu Ile Val
                        450                 455                 460

Thr Ser Gly Leu Glu Thr Ile Glu Asp Glu Asp Leu Ile Glu Arg Glu
        465                 470                 475                 480

Asn Ile Val Val Thr Leu Thr His Asn Gly Tyr Ile Lys Arg Leu Pro
                        485                 490                 495

Ala Ser Thr Tyr Arg Ser Gln Lys Arg Gly Gly Lys Gly Val Gln Gly
                        500                 505                 510

Met Gly Thr Asn
                515

<210> SEQ ID NO 7
<211> LENGTH: 1527
<212> TYPE: DNA
<213> ORGANISM: Bacillus subtilis
<220> FEATURE:
<221> NAME/KEY: CDS
<222> LOCATION: (1)..(1527)

<400> SEQUENCE: 7

| | | | |
|---|---|---|---|
| tat gca atg agc gtt atc gtg tcc cgt gct ctt cca gat gtc cgt gac | | | 48 |
| Tyr Ala Met Ser Val Ile Val Ser Arg Ala Leu Pro Asp Val Arg Asp | | | |
| 1 5 10 15 | | | |
| ggt tta aaa ccg gtt cac aga cgg att ttg tat gca atg aac gat ctg | | | 96 |
| Gly Leu Lys Pro Val His Arg Arg Ile Leu Tyr Ala Met Asn Asp Leu | | | |
| 20 25 30 | | | |
| ggc atg aca agt gac aag gct tat aaa aaa tcc gcg cgt atc gtc gga | | | 144 |
| Gly Met Thr Ser Asp Lys Ala Tyr Lys Lys Ser Ala Arg Ile Val Gly | | | |
| 35 40 45 | | | |
| gaa gtt atc ggg aaa tac cac ccg cat ggt gat tca gcg gta tat gaa | | | 192 |
| Glu Val Ile Gly Lys Tyr His Pro His Gly Asp Ser Ala Val Tyr Glu | | | |
| 50 55 60 | | | |
| tcc atg gtc aga atg gcg cag gat ttc aac tat cgt tat atg ctc gtt | | | 240 |
| Ser Met Val Arg Met Ala Gln Asp Phe Asn Tyr Arg Tyr Met Leu Val | | | |
| 65 70 75 80 | | | |
| gac ggt cac gga aac ttc ggt tct gtt gac ggg gac tca gcg gct gcc | | | 288 |
| Asp Gly His Gly Asn Phe Gly Ser Val Asp Gly Asp Ser Ala Ala Ala | | | |
| 85 90 95 | | | |
| atg cgt tat acg gaa gca aga atg tct aaa atc tcg atg gaa att ctt | | | 336 |
| Met Arg Tyr Thr Glu Ala Arg Met Ser Lys Ile Ser Met Glu Ile Leu | | | |
| 100 105 110 | | | |
| cga gac atc aca aaa gac aca atc gat tat cag gac aac tat gac gga | | | 384 |
| Arg Asp Ile Thr Lys Asp Thr Ile Asp Tyr Gln Asp Asn Tyr Asp Gly | | | |
| 115 120 125 | | | |
| tca gaa aga gaa cct gtc gtt atg cct tca aga ttc ccg aat ctg ctt | | | 432 |
| Ser Glu Arg Glu Pro Val Val Met Pro Ser Arg Phe Pro Asn Leu Leu | | | |
| 130 135 140 | | | |
| gta aac ggc gct gcc gga att gcg gta ggt atg gca aca aac att cct | | | 480 |
| Val Asn Gly Ala Ala Gly Ile Ala Val Gly Met Ala Thr Asn Ile Pro | | | |
| 145 150 155 160 | | | |
| ccg cac cag ttg gga gaa atc att gac ggt gtg ctt gct gtc agt gaa | | | 528 |
| Pro His Gln Leu Gly Glu Ile Ile Asp Gly Val Leu Ala Val Ser Glu | | | |
| 165 170 175 | | | |
| aat cct gaa atc gca gta cag gag ctc atg gag att att cct ggt cct | | | 576 |
| Asn Pro Glu Ile Ala Val Gln Glu Leu Met Glu Ile Ile Pro Gly Pro | | | |
| 180 185 190 | | | |
| gac ttc ccg act gcg ggg caa att ttg ggc cga agc ggt att cgt aaa | | | 624 |
| Asp Phe Pro Thr Ala Gly Gln Ile Leu Gly Arg Ser Gly Ile Arg Lys | | | |
| 195 200 205 | | | |
| gca tac gaa tca gga cga ggc tcg att acg atc cgg gca aaa gcg gag | | | 672 |
| Ala Tyr Glu Ser Gly Arg Gly Ser Ile Thr Ile Arg Ala Lys Ala Glu | | | |
| 210 215 220 | | | |
| atc gaa caa aca tcg tca gga aaa gaa aga att gtc gta aca gaa ctt | | | 720 |
| Ile Glu Gln Thr Ser Ser Gly Lys Glu Arg Ile Val Val Thr Glu Leu | | | |
| 225 230 235 240 | | | |
| cca tac caa gta aat aaa gca aaa cta atc gaa aaa atc gct gat ctt | | | 768 |
| Pro Tyr Gln Val Asn Lys Ala Lys Leu Ile Glu Lys Ile Ala Asp Leu | | | |
| 245 250 255 | | | |
| gtc aga gat aag aag ata gaa ggt att acc gat ctg cgt gat gaa tct | | | 816 |
| Val Arg Asp Lys Lys Ile Glu Gly Ile Thr Asp Leu Arg Asp Glu Ser | | | |
| 260 265 270 | | | |
| gac cgc aca ggt atg aga atc gtc att gaa atc aga aga gat gcc aac | | | 864 |
| Asp Arg Thr Gly Met Arg Ile Val Ile Glu Ile Arg Arg Asp Ala Asn | | | |
| 275 280 285 | | | |
| gcg cat gtc att cta aat aat cta tat aag caa aca gct ttg caa act | | | 912 |
| Ala His Val Ile Leu Asn Asn Leu Tyr Lys Gln Thr Ala Leu Gln Thr | | | |
| 290 295 300 | | | |

| | | |
|---|---|---|
| tct ttt ggt atc aat ctg ctt gcg ctt gtt gac gga cag cca aaa gtt<br>Ser Phe Gly Ile Asn Leu Leu Ala Leu Val Asp Gly Gln Pro Lys Val<br>305                      310                      315                  320 | | 960 |
| tta aat tta aag caa tgc ttg gag tat tac cta gat cac caa aaa gtc<br>Leu Asn Leu Lys Gln Cys Leu Glu Tyr Tyr Leu Asp His Gln Lys Val<br>                      325                      330                      335 | | 1008 |
| gta atc aga cgc cgt act gct tat gaa ttg cgt aaa gcg gag gcg aga<br>Val Ile Arg Arg Arg Thr Ala Tyr Glu Leu Arg Lys Ala Glu Ala Arg<br>              340                      345                      350 | | 1056 |
| gca cat atc ttg gaa gga ttg aga att gct ctt gat cat ctt gat gca<br>Ala His Ile Leu Glu Gly Leu Arg Ile Ala Leu Asp His Leu Asp Ala<br>355                      360                      365 | | 1104 |
| gtt att tcc ctt atc cgt aat tct caa acg gct gaa att gcg aga aca<br>Val Ile Ser Leu Ile Arg Asn Ser Gln Thr Ala Glu Ile Ala Arg Thr<br>            370                      375                      380 | | 1152 |
| gga tta att gaa caa ttc tcg ctg act gaa aaa caa gcc caa gct att<br>Gly Leu Ile Glu Gln Phe Ser Leu Thr Glu Lys Gln Ala Gln Ala Ile<br>385                      390                      395                  400 | | 1200 |
| ctt gat atg aga ctg cag cgt tta aca gga ttg gaa cgt gaa aag att<br>Leu Asp Met Arg Leu Gln Arg Leu Thr Gly Leu Glu Arg Glu Lys Ile<br>                      405                      410                      415 | | 1248 |
| gaa gag gag tac cga tcc ctt gtt aaa tta att gca gag ctt aaa gaa<br>Glu Glu Glu Tyr Arg Ser Leu Val Lys Leu Ile Ala Glu Leu Lys Glu<br>            420                      425                      430 | | 1296 |
| atc ttg gcc aat gaa gaa aaa gtg ctt gag atc att cgt gaa gaa ctc<br>Ile Leu Ala Asn Glu Glu Lys Val Leu Glu Ile Ile Arg Glu Glu Leu<br>435                      440                      445 | | 1344 |
| ata gaa att aaa gag cgt ttt aac gat gaa aga cgc act gag atc gtc<br>Ile Glu Ile Lys Glu Arg Phe Asn Asp Glu Arg Arg Thr Glu Ile Val<br>            450                      455                      460 | | 1392 |
| act gcc ggt ctt gaa aca att gaa gat gaa gat ctc atc gaa aga gaa<br>Thr Ala Gly Leu Glu Thr Ile Glu Asp Glu Asp Leu Ile Glu Arg Glu<br>465                      470                      475                  480 | | 1440 |
| aac atc gtt gtc acc ctg aca cac aac gga tat atc aaa cgt ctg cct<br>Asn Ile Val Val Thr Leu Thr His Asn Gly Tyr Ile Lys Arg Leu Pro<br>            485                      490                      495 | | 1488 |
| gcc tca acc tac cgc agt caa aag cgt ggc gga aaa ggc<br>Ala Ser Thr Tyr Arg Ser Gln Lys Arg Gly Gly Lys Gly<br>500                      505 | | 1527 |

<210> SEQ ID NO 8
<211> LENGTH: 509
<212> TYPE: PRT
<213> ORGANISM: Bacillus subtilis

<400> SEQUENCE: 8

Tyr Ala Met Ser Val Ile Val Ser Arg Ala Leu Pro Asp Val Arg Asp
1                  5                      10                      15

Gly Leu Lys Pro Val His Arg Arg Ile Leu Tyr Ala Met Asn Asp Leu
                  20                      25                      30

Gly Met Thr Ser Asp Lys Ala Tyr Lys Lys Ser Ala Arg Ile Val Gly
            35                      40                      45

Glu Val Ile Gly Lys Tyr His Pro His Gly Asp Ser Ala Val Tyr Glu
  50                      55                      60

Ser Met Val Arg Met Ala Gln Asp Phe Asn Tyr Arg Tyr Met Leu Val
65                    70                      75                  80

Asp Gly His Gly Asn Phe Gly Ser Val Asp Gly Asp Ser Ala Ala Ala
                  85                      90                      95

Met Arg Tyr Thr Glu Ala Arg Met Ser Lys Ile Ser Met Glu Ile Leu

```
            100                 105                 110
Arg Asp Ile Thr Lys Asp Thr Ile Asp Tyr Gln Asp Asn Tyr Asp Gly
        115                 120                 125

Ser Glu Arg Glu Pro Val Val Met Pro Ser Arg Phe Pro Asn Leu Leu
130                 135                 140

Val Asn Gly Ala Ala Gly Ile Ala Val Gly Met Ala Thr Asn Ile Pro
145                 150                 155                 160

Pro His Gln Leu Gly Glu Ile Ile Asp Gly Val Leu Ala Val Ser Glu
                165                 170                 175

Asn Pro Glu Ile Ala Val Gln Glu Leu Met Glu Ile Ile Pro Gly Pro
            180                 185                 190

Asp Phe Pro Thr Ala Gly Gln Ile Leu Gly Arg Ser Gly Ile Arg Lys
        195                 200                 205

Ala Tyr Glu Ser Gly Arg Gly Ser Ile Thr Ile Arg Ala Lys Ala Glu
    210                 215                 220

Ile Glu Gln Thr Ser Ser Gly Lys Glu Arg Ile Val Val Thr Glu Leu
225                 230                 235                 240

Pro Tyr Gln Val Asn Lys Ala Lys Leu Ile Glu Lys Ile Ala Asp Leu
                245                 250                 255

Val Arg Asp Lys Lys Ile Glu Gly Ile Thr Asp Leu Arg Asp Glu Ser
            260                 265                 270

Asp Arg Thr Gly Met Arg Ile Val Ile Glu Ile Arg Arg Asp Ala Asn
        275                 280                 285

Ala His Val Ile Leu Asn Asn Leu Tyr Lys Gln Thr Ala Leu Gln Thr
    290                 295                 300

Ser Phe Gly Ile Asn Leu Leu Ala Leu Val Asp Gly Gln Pro Lys Val
305                 310                 315                 320

Leu Asn Leu Lys Gln Cys Leu Glu Tyr Tyr Leu Asp His Gln Lys Val
                325                 330                 335

Val Ile Arg Arg Arg Thr Ala Tyr Glu Leu Arg Lys Ala Glu Ala Arg
            340                 345                 350

Ala His Ile Leu Glu Gly Leu Arg Ile Ala Leu Asp His Leu Asp Ala
        355                 360                 365

Val Ile Ser Leu Ile Arg Asn Ser Gln Thr Ala Glu Ile Ala Arg Thr
    370                 375                 380

Gly Leu Ile Glu Gln Phe Ser Leu Thr Glu Lys Gln Ala Gln Ala Ile
385                 390                 395                 400

Leu Asp Met Arg Leu Gln Arg Leu Thr Gly Leu Glu Arg Glu Lys Ile
                405                 410                 415

Glu Glu Glu Tyr Arg Ser Leu Val Lys Leu Ile Ala Glu Leu Lys Glu
            420                 425                 430

Ile Leu Ala Asn Glu Glu Lys Val Leu Glu Ile Ile Arg Glu Glu Leu
        435                 440                 445

Ile Glu Ile Lys Glu Arg Phe Asn Asp Glu Arg Arg Thr Glu Ile Val
    450                 455                 460

Thr Ala Gly Leu Glu Thr Ile Glu Asp Glu Asp Leu Ile Glu Arg Glu
465                 470                 475                 480

Asn Ile Val Val Thr Leu Thr His Asn Gly Tyr Ile Lys Arg Leu Pro
                485                 490                 495

Ala Ser Thr Tyr Arg Ser Gln Lys Arg Gly Gly Lys Gly
            500                 505

<210> SEQ ID NO 9
```

```
<211> LENGTH: 1507
<212> TYPE: DNA
<213> ORGANISM: Bacillus subtilis

<400> SEQUENCE: 9
gacgaacgct ggcggcgtgc ctaatacatg caagtcgagc ggacagatgg gagcttgctc    60
cctgatgtta gcggcggacg ggtgagtaac acgtgggtaa cctgcctgta agactgggat   120
aactccggga aaccggggct aataccggat gcttgtttga accgcatggt tcaaacataa   180
aaggtggctt cggctaccac ttacagatgg acccgcggcg cattagctag ttggtgaggt   240
aacggctcac caaggcaacg atgcgtagcc gacctgagag ggtgatcggc cacactggga   300
ctgagacacg gcccagactc ctacgggagg cagcagtagg gaatcttccg caatggacga   360
aagtctgacg gagcaacgcc gcgtgagtga tgaaggtttt cggatcgtaa agctctgttg   420
ttagggaaga acaagtaccg ttcgaatagg gcggtacctt gacggtacct aaccagaaag   480
ccacggctaa ctacgtgcca gcagccgcgg taatacgtag gtggcaagcg ttgtccggaa   540
ttattgggcg taaagggctc gcaggcggtt tcttaagtct gatgtgaaag cccccggctc   600
aaccggggag ggtcattgga aactgggaa cttgagtgca gaagaggaga gtggaattcc   660
acgtgtagcg gtgaaatgcg tagagatgtg gaggaacacc agtggcgaag gcgactctct   720
ggtctgtaac tgacgctgag gagcgaaagc gtggggagcg aacaggatta gataccctgg   780
tagtccacgc cgtaaacgat gagtgctaag tgttaggggg ttttccgccc ttagtgctgc   840
agctaacgca ttaagcactc cgcctgggga gtacggtcgc aagactgaaa ctcaaaggaa   900
ttgacggggg cccgcacaag cggtggagca tgtggtttaa ttcgaagcaa cgcgaagaac   960
cttaccaggt cttgacatcc tctgacaatc ctagagatag gacgtcccct cggggggcag  1020
agtgacaggt ggtgcatggt tgtcgtcagc tcgtgtcgtg agatgttggg ttaagtcccg  1080
caacgagcgc aaccccttgat cttagttgcc agcattcagt tgggcactct aaggtgactg  1140
ccggtgacaa accggaggaa ggtggggatg acgtcaaatc atcatgcccc ttatgacctg  1200
ggctacacac gtgctacaat ggacagaaca aagggcagcg aaaccgcgag gttaagccaa  1260
tcccacaaat ctgttctcag ttcggatcgc agtctgcaac tcgactgcgt gaagctggaa  1320
tcgctagtaa tcgcggatca gcatgccgcg gtgaatacgt tcccgggcct tgtacacacc  1380
gcccgtcaca ccacgagagt ttgtaacacc cgaagtcggt gaggtaacct tttaggagcc  1440
agccgccgaa ggtgggacag atgattgggg tgaagtcgta acaaggtagc cgtatcggaa  1500
ggtgcgg                                                             1507

<210> SEQ ID NO 10
<211> LENGTH: 19
<212> TYPE: DNA
<213> ORGANISM: Artificial sequence
<220> FEATURE:
<223> OTHER INFORMATION: DNA primer

<400> SEQUENCE: 10
gagtttgatc ctggctcag                                                  19

<210> SEQ ID NO 11
<211> LENGTH: 20
<212> TYPE: DNA
<213> ORGANISM: Artificial sequence
<220> FEATURE:
<223> OTHER INFORMATION: DNA primer

<400> SEQUENCE: 11
```
agaaaggagg tgatccagcc                                                    20

<210> SEQ ID NO 12
<211> LENGTH: 21
<212> TYPE: DNA
<213> ORGANISM: Artificial sequence
<220> FEATURE:
<223> OTHER INFORMATION: PCR primer

<400> SEQUENCE: 12
atctaatcct gtttgctccc c                                                  21

<210> SEQ ID NO 13
<211> LENGTH: 15
<212> TYPE: DNA
<213> ORGANISM: Artificial sequence
<220> FEATURE:
<223> OTHER INFORMATION: PCR primer

<400> SEQUENCE: 13
tacgggaggc agcag                                                         15

<210> SEQ ID NO 14
<211> LENGTH: 17
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (9)..(9)
<223> OTHER INFORMATION: n is a or g

<400> SEQUENCE: 14
cggtgtgtnc aaggccc                                                       17

<210> SEQ ID NO 15
<211> LENGTH: 16
<212> TYPE: DNA
<213> ORGANISM: Artificial sequence
<220> FEATURE:
<223> OTHER INFORMATION: PCR primer

<400> SEQUENCE: 15
caacgagcgc aaccct                                                        16

<210> SEQ ID NO 16
<211> LENGTH: 20
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (3)..(3)
<223> OTHER INFORMATION: n is a or c
<220> FEATURE:
<221> NAME/KEY: misc_feature
<222> LOCATION: (15)..(15)
<223> OTHER INFORMATION: n is g or c

<400> SEQUENCE: 16
gtntgggaaa ttgtngacaa                                                    20

<210> SEQ ID NO 17
<211> LENGTH: 20
<212> TYPE: DNA

```
<213> ORGANISM: Artificial sequence
<220> FEATURE:
<223> OTHER INFORMATION: PCR primer
<220> FEATURE:
<221> NAME/KEY: misc_feature
<222> LOCATION: (8)..(8)
<223> OTHER INFORMATION: c or t
<220> FEATURE:
<221> NAME/KEY: misc_feature
<222> LOCATION: (14)..(14)
<223> OTHER INFORMATION: n is a or g
<220> FEATURE:
<221> NAME/KEY: misc_feature
<222> LOCATION: (17)..(17)
<223> OTHER INFORMATION: n is a or g

<400> SEQUENCE: 17
gcggttcnac tttntcnccc                                          20

<210> SEQ ID NO 18
<211> LENGTH: 20
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (3)..(3)
<223> OTHER INFORMATION: n is c or t
<220> FEATURE:
<221> NAME/KEY: misc_feature
<222> LOCATION: (6)..(6)
<223> OTHER INFORMATION: n is c or t
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (18)..(18)
<223> OTHER INFORMATION: n is c or t

<400> SEQUENCE: 18
ggnatnccng tcggcatnca                                          20

<210> SEQ ID NO 19
<211> LENGTH: 20
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (6)..(6)
<223> OTHER INFORMATION: n is g or c
<220> FEATURE:
<221> NAME/KEY: misc_feature
<222> LOCATION: (9)..(9)
<223> OTHER INFORMATION: n is c or t
<220> FEATURE:
<221> NAME/KEY: misc_feature
<222> LOCATION: (12)..(12)
<223> OTHER INFORMATION: n is c or t
<220> FEATURE:
<221> NAME/KEY: misc_feature
<222> LOCATION: (18)..(18)
<223> OTHER INFORMATION: n is a or c

<400> SEQUENCE: 19
tccatngtng tntcccanag                                          20
```

<210> SEQ ID NO 20
<211> LENGTH: 20
<212> TYPE: DNA
<213> ORGANISM: Artificial sequence
<220> FEATURE:
<223> OTHER INFORMATION: PCR primer

<400> SEQUENCE: 20
tacgcatgat ttgagggtg                                        20

<210> SEQ ID NO 21
<211> LENGTH: 21
<212> TYPE: DNA
<213> ORGANISM: Artificial sequence
<220> FEATURE:
<223> OTHER INFORMATION: PCR primer

<400> SEQUENCE: 21
aaccgatgtc acttgccttt a                                     21

<210> SEQ ID NO 22
<211> LENGTH: 20
<212> TYPE: DNA
<213> ORGANISM: Artificial sequence
<220> FEATURE:
<223> OTHER INFORMATION: PCR primer

<400> SEQUENCE: 22
ttaattaaca aagaaactgg                                       20

<210> SEQ ID NO 23
<211> LENGTH: 20
<212> TYPE: DNA
<213> ORGANISM: Artificial sequence
<220> FEATURE:
<223> OTHER INFORMATION: Primer

<400> SEQUENCE: 23
atgtaatcgg caatgcttac                                       20

<210> SEQ ID NO 24
<211> LENGTH: 20
<212> TYPE: DNA
<213> ORGANISM: Artificial sequence
<220> FEATURE:
<223> OTHER INFORMATION: Primer

<400> SEQUENCE: 24
aggctgtgcc tttgatgcag                                       20

<210> SEQ ID NO 25
<211> LENGTH: 20
<212> TYPE: DNA
<213> ORGANISM: Artificial sequence
<220> FEATURE:
<223> OTHER INFORMATION: Primer

<400> SEQUENCE: 25
gaaacgtaag atttctgaag                                       20

<210> SEQ ID NO 26
<211> LENGTH: 20
<212> TYPE: DNA
<213> ORGANISM: Artificial sequence
<220> FEATURE:

```
<223> OTHER INFORMATION: Primer

<400> SEQUENCE: 26
gagagcacgc aaaagaaccg                                               20

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
gtttcaatcg gacacatacg                                               20

<210> SEQ ID NO 28
<211> LENGTH: 20
<212> TYPE: DNA
<213> ORGANISM: Artificial sequence
<220> FEATURE:
<223> OTHER INFORMATION: Primer

<400> SEQUENCE: 28
ccgtcagcaa ggatttctcc                                               20

<210> SEQ ID NO 29
<211> LENGTH: 20
<212> TYPE: DNA
<213> ORGANISM: Artificial sequence
<220> FEATURE:
<223> OTHER INFORMATION: Primer

<400> SEQUENCE: 29
tccataccta agctttgaag                                               20

<210> SEQ ID NO 30
<211> LENGTH: 19
<212> TYPE: DNA
<213> ORGANISM: Artificial Sequence
<220> FEATURE:
<223> OTHER INFORMATION: Primer BS-F
<220> FEATURE:
<221> NAME/KEY: misc_feature
<222> LOCATION: (9)..(9)
<223> OTHER INFORMATION: n is a, c, g or t
<220> FEATURE:
<221> NAME/KEY: misc_feature
<222> LOCATION: (12)..(12)
<223> OTHER INFORMATION: n is a, c, g or t
<220> FEATURE:
<221> NAME/KEY: misc_feature
<222> LOCATION: (15)..(15)
<223> OTHER INFORMATION: n is c or t

<400> SEQUENCE: 30
gaaggcggna cncangaag                                                19

<210> SEQ ID NO 31
<211> LENGTH: 19
<212> TYPE: DNA
<213> ORGANISM: Artificial Sequence
<220> FEATURE:
<223> OTHER INFORMATION: Primer BS-R
<220> FEATURE:
<221> NAME/KEY: misc_feature
<222> LOCATION: (5)..(5)
<223> OTHER INFORMATION: n is a or g
<220> FEATURE:
<221> NAME/KEY: misc_feature
```

```
<222> LOCATION: (8)..(8)
<223> OTHER INFORMATION: n is a, c, g or t
<220> FEATURE:
<221> NAME/KEY: misc_feature
<222> LOCATION: (11)..(11)
<223> OTHER INFORMATION: n is a, c, g or t

<400> SEQUENCE: 31
cttcntgngt nccgccttc                                                    19

<210> SEQ ID NO 32
<211> LENGTH: 1577
<212> TYPE: DNA
<213> ORGANISM: Bacillus subtilis
<220> FEATURE:
<221> NAME/KEY: CDS
<222> LOCATION: (1)..(1575)

<400> SEQUENCE: 32
```

| | | | | | | | | | | | | | | | | |
|---|---|---|---|---|---|---|---|---|---|---|---|---|---|---|---|---|
| agt | att | gac | gaa | gcc | ctc | gcc | ggt | tat | tgt | acg | gat | atc | aat | atc | caa | 48 |
| Ser | Ile | Asp | Glu | Ala | Leu | Ala | Gly | Tyr | Cys | Thr | Asp | Ile | Asn | Ile | Gln | |
| 1 | | | | 5 | | | | | 10 | | | | | 15 | | |
| atc | gaa | aaa | gac | aac | agc | atc | acg | gtg | gta | gat | aac | ggc | cgc | ggt | att | 96 |
| Ile | Glu | Lys | Asp | Asn | Ser | Ile | Thr | Val | Val | Asp | Asn | Gly | Arg | Gly | Ile | |
| | | | 20 | | | | | 25 | | | | | 30 | | | |
| cca | gtt | ggt | att | cat | gaa | aaa | atg | ggc | cgg | cct | gcg | gta | gag | gtc | att | 144 |
| Pro | Val | Gly | Ile | His | Glu | Lys | Met | Gly | Arg | Pro | Ala | Val | Glu | Val | Ile | |
| | | 35 | | | | | 40 | | | | | 45 | | | | |
| atg | acg | gtg | ctt | cat | gcc | gga | ggg | aaa | ttt | gac | gga | agc | ggc | tat | aaa | 192 |
| Met | Thr | Val | Leu | His | Ala | Gly | Gly | Lys | Phe | Asp | Gly | Ser | Gly | Tyr | Lys | |
| | 50 | | | | | 55 | | | | | 60 | | | | | |
| gta | tcc | gga | gga | ttg | cac | ggt | gta | ggt | gcg | tca | gtc | gta | aac | gcg | ctt | 240 |
| Val | Ser | Gly | Gly | Leu | His | Gly | Val | Gly | Ala | Ser | Val | Val | Asn | Ala | Leu | |
| 65 | | | | | 70 | | | | | 75 | | | | | 80 | |
| tca | acc | gag | ctt | gtt | gtg | acg | gta | cac | cgt | gac | gga | aaa | atc | cac | cgt | 288 |
| Ser | Thr | Glu | Leu | Val | Val | Thr | Val | His | Arg | Asp | Gly | Lys | Ile | His | Arg | |
| | | | | 85 | | | | | 90 | | | | | 95 | | |
| caa | acc | tat | aaa | cgc | gga | gtt | ccg | gtt | tca | gac | ctt | gaa | atc | att | ggc | 336 |
| Gln | Thr | Tyr | Lys | Arg | Gly | Val | Pro | Val | Ser | Asp | Leu | Glu | Ile | Ile | Gly | |
| | | | 100 | | | | | 105 | | | | | 110 | | | |
| gaa | aca | gat | cat | tca | gga | acg | acg | aca | cat | ttt | gtc | cca | gat | cct | gag | 384 |
| Glu | Thr | Asp | His | Ser | Gly | Thr | Thr | Thr | His | Phe | Val | Pro | Asp | Pro | Glu | |
| | | 115 | | | | | 120 | | | | | 125 | | | | |
| att | ttc | aca | gaa | aca | act | gtg | tat | gat | tat | gat | ctg | ctt | gct | aac | cgt | 432 |
| Ile | Phe | Thr | Glu | Thr | Thr | Val | Tyr | Asp | Tyr | Asp | Leu | Leu | Ala | Asn | Arg | |
| | 130 | | | | | 135 | | | | | 140 | | | | | |
| gtg | cgc | gaa | tta | gcc | ttt | ttg | aca | aaa | ggc | gta | aac | atc | acg | att | gaa | 480 |
| Val | Arg | Glu | Leu | Ala | Phe | Leu | Thr | Lys | Gly | Val | Asn | Ile | Thr | Ile | Glu | |
| 145 | | | | | 150 | | | | | 155 | | | | | 160 | |
| gat | aaa | cgt | gaa | gga | caa | gag | cgc | aaa | aat | gag | tac | cat | tac | gaa | ggc | 528 |
| Asp | Lys | Arg | Glu | Gly | Gln | Glu | Arg | Lys | Asn | Glu | Tyr | His | Tyr | Glu | Gly | |
| | | | | 165 | | | | | 170 | | | | | 175 | | |
| gga | att | aaa | agt | tat | gta | gag | tat | tta | aac | cgt | tct | aaa | gaa | gtt | gtc | 576 |
| Gly | Ile | Lys | Ser | Tyr | Val | Glu | Tyr | Leu | Asn | Arg | Ser | Lys | Glu | Val | Val | |
| | | | 180 | | | | | 185 | | | | | 190 | | | |
| cat | gaa | gag | ccg | att | tac | att | gaa | ggc | gaa | aag | gac | ggc | att | acg | gtt | 624 |
| His | Glu | Glu | Pro | Ile | Tyr | Ile | Glu | Gly | Glu | Lys | Asp | Gly | Ile | Thr | Val | |
| | | 195 | | | | | 200 | | | | | 205 | | | | |
| gaa | gtg | gct | ttg | caa | tat | aat | gac | agc | tac | aca | agc | aac | att | tac | tcg | 672 |
| Glu | Val | Ala | Leu | Gln | Tyr | Asn | Asp | Ser | Tyr | Thr | Ser | Asn | Ile | Tyr | Ser | |
| | 210 | | | | | 215 | | | | | 220 | | | | | |
| ttt | aca | aat | aac | att | aac | acg | tat | gaa | ggc | ggg | acc | cac | gaa | gca | ggc | 720 |

```
Phe Thr Asn Asn Ile Asn Thr Tyr Glu Gly Gly Thr His Glu Ala Gly
225                 230                 235                 240 ttc aaa acg ggc ctg act cgt gtg atc aat gat tac gcc aga aaa aaa        768
Phe Lys Thr Gly Leu Thr Arg Val Ile Asn Asp Tyr Ala Arg Lys Lys
                    245                 250                 255 ggg ctc att aaa gaa aat gat ccg aac tta agc ggt gac gac gta aga        816
Gly Leu Ile Lys Glu Asn Asp Pro Asn Leu Ser Gly Asp Asp Val Arg
                260                 265                 270 gaa ggg ctg acc gcg att att tcc atc aaa cac cct gat ccg cag ttt        864
Glu Gly Leu Thr Ala Ile Ile Ser Ile Lys His Pro Asp Pro Gln Phe
            275                 280                 285 gaa ggc caa acg aaa aca aaa cta ggc aac tcg gaa gcg cgg acg atc        912
Glu Gly Gln Thr Lys Thr Lys Leu Gly Asn Ser Glu Ala Arg Thr Ile
        290                 295                 300 acc gat acg tta ttt tct gcg gca ttg gaa aca ttt atg ctg gaa aat        960
Thr Asp Thr Leu Phe Ser Ala Ala Leu Glu Thr Phe Met Leu Glu Asn
305                 310                 315                 320 cca gat gcg gcc aaa aaa att gtc gac aaa ggt ttg atg gcg gca aga       1008
Pro Asp Ala Ala Lys Lys Ile Val Asp Lys Gly Leu Met Ala Ala Arg
                325                 330                 335 gca aga atg gct gcg aaa aaa gcg cgt gaa tta aca cgc cgc aag agt       1056
Ala Arg Met Ala Ala Lys Lys Ala Arg Glu Leu Thr Arg Arg Lys Ser
                340                 345                 350 gct ttg gaa att tca aac ctt ccc ggt aag cta gcg gac tgc tca tca       1104
Ala Leu Glu Ile Ser Asn Leu Pro Gly Lys Leu Ala Asp Cys Ser Ser
            355                 360                 365 aaa gat ccg agc att tcc gag tta tat atc gta gag ggt gac tct gcc       1152
Lys Asp Pro Ser Ile Ser Glu Leu Tyr Ile Val Glu Gly Asp Ser Ala
        370                 375                 380 gga gga tca gct aaa caa ggc cgc gac aga cat ttc caa gcc att ttg       1200
Gly Gly Ser Ala Lys Gln Gly Arg Asp Arg His Phe Gln Ala Ile Leu
385                 390                 395                 400 ccg ctt aga ggt aaa atc tta aac gtt gaa aaa gcg aga ttg gac aaa       1248
Pro Leu Arg Gly Lys Ile Leu Asn Val Glu Lys Ala Arg Leu Asp Lys
                405                 410                 415 atc ctt tcc aac aac gaa gtt cgt tct atg atc aca gca ctc gga aca       1296
Ile Leu Ser Asn Asn Glu Val Arg Ser Met Ile Thr Ala Leu Gly Thr
                420                 425                 430 ggt ata ggg gaa gat ttc aac ttg ggg aaa gcc cgt tac cat aaa gtt       1344
Gly Ile Gly Glu Asp Phe Asn Leu Gly Lys Ala Arg Tyr His Lys Val
            435                 440                 445 gtc att atg act gat gcc gac gtt gac ggc gcg cac atc aga aca ctg       1392
Val Ile Met Thr Asp Ala Asp Val Asp Gly Ala His Ile Arg Thr Leu
        450                 455                 460 ctg tta acg ttc ttt tac aga tat atg cgc caa att att gaa aat ggc       1440
Leu Leu Thr Phe Phe Tyr Arg Tyr Met Arg Gln Ile Ile Glu Asn Gly
465                 470                 475                 480 tac gtg tat att gcg cag ccg ccg ctc tac aag gtt caa cag gga aaa       1488
Tyr Val Tyr Ile Ala Gln Pro Pro Leu Tyr Lys Val Gln Gln Gly Lys
                485                 490                 495 cgt gtt gaa tat gca tat aat gac aaa gaa ctt gat gat ctg ttg aaa       1536
Arg Val Glu Tyr Ala Tyr Asn Asp Lys Glu Leu Asp Asp Leu Leu Lys
                500                 505                 510 act ctt cct caa acg cct aag cct ggc ttg cag cgt tat aa               1577
Thr Leu Pro Gln Thr Pro Lys Pro Gly Leu Gln Arg Tyr
            515                 520                 525

<210> SEQ ID NO 33
<211> LENGTH: 525
<212> TYPE: PRT
```

<213> ORGANISM: Bacillus subtilis

<400> SEQUENCE: 33

Ser Ile Asp Glu Ala Leu Ala Gly Tyr Cys Thr Asp Ile Asn Ile Gln
1               5                   10                  15

Ile Glu Lys Asp Asn Ser Ile Thr Val Val Asp Asn Gly Arg Gly Ile
            20                  25                  30

Pro Val Gly Ile His Glu Lys Met Gly Arg Pro Ala Val Glu Val Ile
        35                  40                  45

Met Thr Val Leu His Ala Gly Gly Lys Phe Asp Gly Ser Gly Tyr Lys
    50                  55                  60

Val Ser Gly Gly Leu His Gly Val Gly Ala Ser Val Val Asn Ala Leu
65                  70                  75                  80

Ser Thr Glu Leu Val Val Thr Val His Arg Asp Gly Lys Ile His Arg
                85                  90                  95

Gln Thr Tyr Lys Arg Gly Val Pro Val Ser Asp Leu Glu Ile Ile Gly
            100                 105                 110

Glu Thr Asp His Ser Gly Thr Thr Thr His Phe Val Pro Asp Pro Glu
        115                 120                 125

Ile Phe Thr Glu Thr Thr Val Tyr Asp Tyr Asp Leu Leu Ala Asn Arg
    130                 135                 140

Val Arg Glu Leu Ala Phe Leu Thr Lys Gly Val Asn Ile Thr Ile Glu
145                 150                 155                 160

Asp Lys Arg Glu Gly Gln Glu Arg Lys Asn Glu Tyr His Tyr Glu Gly
                165                 170                 175

Gly Ile Lys Ser Tyr Val Glu Tyr Leu Asn Arg Ser Lys Glu Val Val
            180                 185                 190

His Glu Glu Pro Ile Tyr Ile Glu Gly Glu Lys Asp Gly Ile Thr Val
        195                 200                 205

Glu Val Ala Leu Gln Tyr Asn Asp Ser Tyr Thr Ser Asn Ile Tyr Ser
    210                 215                 220

Phe Thr Asn Asn Ile Asn Thr Tyr Glu Gly Gly Thr His Glu Ala Gly
225                 230                 235                 240

Phe Lys Thr Gly Leu Thr Arg Val Ile Asn Asp Tyr Ala Arg Lys Lys
                245                 250                 255

Gly Leu Ile Lys Glu Asn Asp Pro Asn Leu Ser Gly Asp Asp Val Arg
            260                 265                 270

Glu Gly Leu Thr Ala Ile Ile Ser Ile Lys His Pro Asp Pro Gln Phe
        275                 280                 285

Glu Gly Gln Thr Lys Thr Lys Leu Gly Asn Ser Glu Ala Arg Thr Ile
    290                 295                 300

Thr Asp Thr Leu Phe Ser Ala Ala Leu Glu Thr Phe Met Leu Glu Asn
305                 310                 315                 320

Pro Asp Ala Ala Lys Lys Ile Val Asp Lys Gly Leu Met Ala Ala Arg
                325                 330                 335

Ala Arg Met Ala Ala Lys Lys Ala Arg Glu Leu Thr Arg Arg Lys Ser
            340                 345                 350

Ala Leu Glu Ile Ser Asn Leu Pro Gly Lys Leu Ala Asp Cys Ser Ser
        355                 360                 365

Lys Asp Pro Ser Ile Ser Glu Leu Tyr Ile Val Glu Gly Asp Ser Ala
    370                 375                 380

Gly Gly Ser Ala Lys Gln Gly Arg Asp Arg His Phe Gln Ala Ile Leu
385                 390                 395                 400

```
Pro Leu Arg Gly Lys Ile Leu Asn Val Glu Lys Ala Arg Leu Asp Lys
                405                 410                 415

Ile Leu Ser Asn Asn Glu Val Arg Ser Met Ile Thr Ala Leu Gly Thr
            420                 425                 430

Gly Ile Gly Glu Asp Phe Asn Leu Gly Lys Ala Arg Tyr His Lys Val
        435                 440                 445

Val Ile Met Thr Asp Ala Asp Val Asp Gly Ala His Ile Arg Thr Leu
    450                 455                 460

Leu Leu Thr Phe Phe Tyr Arg Tyr Met Arg Gln Ile Ile Glu Asn Gly
465                 470                 475                 480

Tyr Val Tyr Ile Ala Gln Pro Pro Leu Tyr Lys Val Gln Gln Gly Lys
                485                 490                 495

Arg Val Glu Tyr Ala Tyr Asn Asp Lys Glu Leu Asp Asp Leu Leu Lys
            500                 505                 510

Thr Leu Pro Gln Thr Pro Lys Pro Gly Leu Gln Arg Tyr
        515                 520                 525

<210> SEQ ID NO 34
<211> LENGTH: 3368
<212> TYPE: DNA
<213> ORGANISM: Bacillus subtilis
<220> FEATURE:
<221> NAME/KEY: CDS
<222> LOCATION: (1)..(3366)

<400> SEQUENCE: 34 ttg aca ggt caa cta gtt cag tat gga cga cac cgc cag cgc aga agc      48
Leu Thr Gly Gln Leu Val Gln Tyr Gly Arg His Arg Gln Arg Arg Ser
1               5                   10                  15 tat gct cgc att agc gaa gtg tta gaa tta cca aat ctc att gaa att      96
Tyr Ala Arg Ile Ser Glu Val Leu Glu Leu Pro Asn Leu Ile Glu Ile
            20                  25                  30 caa acc tct tct tat cag tgg ttt ctt gat gag ggt ctt aga gag atg     144
Gln Thr Ser Ser Tyr Gln Trp Phe Leu Asp Glu Gly Leu Arg Glu Met
        35                  40                  45 ttt caa gac ata tca cca att gag gat ttc act ggt aac ctc tct ctt     192
Phe Gln Asp Ile Ser Pro Ile Glu Asp Phe Thr Gly Asn Leu Ser Leu
    50                  55                  60 gag ttc att gat tat agt tta ggt gag cct aaa tat cct gta gag gaa     240
Glu Phe Ile Asp Tyr Ser Leu Gly Glu Pro Lys Tyr Pro Val Glu Glu
65                  70                  75                  80 tca aaa gaa cgt gat gtg act tac tca gct ccg cta aga gtg aag gtt     288
Ser Lys Glu Arg Asp Val Thr Tyr Ser Ala Pro Leu Arg Val Lys Val
                85                  90                  95 cgt tta att aac aaa gaa act gga gag gta aaa gac caa gat gtc ttc     336
Arg Leu Ile Asn Lys Glu Thr Gly Glu Val Lys Asp Gln Asp Val Phe
            100                 105                 110 atg ggg gat ttc ccg att atg aca gat aca ggt act ttt atc att aat     384
Met Gly Asp Phe Pro Ile Met Thr Asp Thr Gly Thr Phe Ile Ile Asn
        115                 120                 125 ggt gcg gaa cgt gta atc gtt tcc cag ctt gtt cgg tct cca agt gta     432
Gly Ala Glu Arg Val Ile Val Ser Gln Leu Val Arg Ser Pro Ser Val
    130                 135                 140 tat ttc agt ggt aaa gta gac aaa aac ggt aaa aaa ggt ttt acc gca     480
Tyr Phe Ser Gly Lys Val Asp Lys Asn Gly Lys Lys Gly Phe Thr Ala
145                 150                 155                 160 act gtc att cca aac cgt ggc gca tgg tta gaa tac gaa act gat gcg     528
Thr Val Ile Pro Asn Arg Gly Ala Trp Leu Glu Tyr Glu Thr Asp Ala
                165                 170                 175
```

```
aaa gat gtt gtt tat gtc cgc att gat cgc aca cgt aag ttg ccg gtt        576
Lys Asp Val Val Tyr Val Arg Ile Asp Arg Thr Arg Lys Leu Pro Val
            180                 185                 190 acg gtt ctt ttg cgt gct ctc ggc ttc ggt tcc gat caa gag att ctt        624
Thr Val Leu Leu Arg Ala Leu Gly Phe Gly Ser Asp Gln Glu Ile Leu
        195                 200                 205 gat ctc gta gga gaa aat gaa tac ctg cga aat acg ctt gat aaa gat        672
Asp Leu Val Gly Glu Asn Glu Tyr Leu Arg Asn Thr Leu Asp Lys Asp
210                 215                 220 aac aca gaa aat agc gac aaa gct ttg ctt gaa att tac gaa cgt ctc        720
Asn Thr Glu Asn Ser Asp Lys Ala Leu Leu Glu Ile Tyr Glu Arg Leu
225                 230                 235                 240 cgt cct gga gag cca cct aca gtt gaa aat gcg aaa agc ttg ctt gat        768
Arg Pro Gly Glu Pro Pro Thr Val Glu Asn Ala Lys Ser Leu Leu Asp
            245                 250                 255 tcg cgt ttc ttt gat ccg aaa cgt tac gat ctt gcc aat gta gga cgc        816
Ser Arg Phe Phe Asp Pro Lys Arg Tyr Asp Leu Ala Asn Val Gly Arg
        260                 265                 270 tat aaa att aat aaa aaa ctt cat att aag aat cgc ctc ttt aat cag        864
Tyr Lys Ile Asn Lys Lys Leu His Ile Lys Asn Arg Leu Phe Asn Gln
275                 280                 285 aga ctt gct gaa acg ctt gtt gac cct gaa aca gga gaa atc ctt gct        912
Arg Leu Ala Glu Thr Leu Val Asp Pro Glu Thr Gly Glu Ile Leu Ala
290                 295                 300 gaa aaa ggt cag att ctt gat aga aga aca ctt gat aaa gta ctg cca        960
Glu Lys Gly Gln Ile Leu Asp Arg Arg Thr Leu Asp Lys Val Leu Pro
305                 310                 315                 320 tac tta gaa agc gga atc ggt ttc aga aag ctg tat cca aat ggc ggt       1008
Tyr Leu Glu Ser Gly Ile Gly Phe Arg Lys Leu Tyr Pro Asn Gly Gly
            325                 330                 335 gtt gtt gaa gat gaa gta act ctt caa tcg att aaa atc tat gct ccg       1056
Val Val Glu Asp Glu Val Thr Leu Gln Ser Ile Lys Ile Tyr Ala Pro
        340                 345                 350 act gac caa gaa gga gaa cag gtt atc aat gta atc ggc aat gct tac       1104
Thr Asp Gln Glu Gly Glu Gln Val Ile Asn Val Ile Gly Asn Ala Tyr
355                 360                 365 att gaa gaa gag att aaa aac att acg cct gct gat att att tcc tct       1152
Ile Glu Glu Glu Ile Lys Asn Ile Thr Pro Ala Asp Ile Ile Ser Ser
370                 375                 380 atc agc tac ttc ttc aac ctg ctg cac gga gta ggc gat aca gat gat       1200
Ile Ser Tyr Phe Phe Asn Leu Leu His Gly Val Gly Asp Thr Asp Asp
385                 390                 395                 400 atc gat cat ctt gga aac cgc cgt tta cgt tct gta ggt gaa ctt ctc       1248
Ile Asp His Leu Gly Asn Arg Arg Leu Arg Ser Val Gly Glu Leu Leu
            405                 410                 415 cag aac caa ttc cgt atc ggg tta agc cgt atg gag cgt gtg gtt cgt       1296
Gln Asn Gln Phe Arg Ile Gly Leu Ser Arg Met Glu Arg Val Val Arg
        420                 425                 430 gag aga atg tca att caa gat acg aat aca att acg cct cag cag ttg       1344
Glu Arg Met Ser Ile Gln Asp Thr Asn Thr Ile Thr Pro Gln Gln Leu
435                 440                 445 atc aat att cgt cct gtt att gcg tcc att aaa gag ttc ttt gga agc       1392
Ile Asn Ile Arg Pro Val Ile Ala Ser Ile Lys Glu Phe Phe Gly Ser
450                 455                 460 tct cag ctt tcc cag ttc atg gac cag acg aac ccg ctt gct gaa tta       1440
Ser Gln Leu Ser Gln Phe Met Asp Gln Thr Asn Pro Leu Ala Glu Leu
465                 470                 475                 480 acg cat aag cgt cgt ctg tca gca tta gga cca ggc gga ttg aca cgt       1488
Thr His Lys Arg Arg Leu Ser Ala Leu Gly Pro Gly Gly Leu Thr Arg
            485                 490                 495
```

```
gaa cgt gcc gga atg gaa gtg cgt gac gtt cac tac tcc cac tat ggc   1536
Glu Arg Ala Gly Met Glu Val Arg Asp Val His Tyr Ser His Tyr Gly
            500                 505                 510 cgt atg tgt ccg att gaa aca cct gag ggt cca aac atc ggt ttg atc   1584
Arg Met Cys Pro Ile Glu Thr Pro Glu Gly Pro Asn Ile Gly Leu Ile
        515                 520                 525 aac tcg ctt tca tct tat gca aaa gta aac cgt ttt ggt ttc atc gaa   1632
Asn Ser Leu Ser Ser Tyr Ala Lys Val Asn Arg Phe Gly Phe Ile Glu
530                 535                 540 acg cct tat cgc cgt gtt gac cct gaa aca ggg aag gta acg ggc aga   1680
Thr Pro Tyr Arg Arg Val Asp Pro Glu Thr Gly Lys Val Thr Gly Arg
545                 550                 555                 560 atc gat tac tta act gct gat gaa gag gat aac tat gtt gtc gct cag   1728
Ile Asp Tyr Leu Thr Ala Asp Glu Glu Asp Asn Tyr Val Val Ala Gln
                565                 570                 575 gcg aac gct cgt ctt gat gac gat ggc tca ttt att gat gac agc att   1776
Ala Asn Ala Arg Leu Asp Asp Asp Gly Ser Phe Ile Asp Asp Ser Ile
            580                 585                 590 atc gcc cgt ttc cgc ggg gag aac acc gtt gtt tcc aga aac cgt gtg   1824
Ile Ala Arg Phe Arg Gly Glu Asn Thr Val Val Ser Arg Asn Arg Val
        595                 600                 605 gat tac atg gat gta tca cct aag cag gtt gtt tct gct gcg aca gca   1872
Asp Tyr Met Asp Val Ser Pro Lys Gln Val Val Ser Ala Ala Thr Ala
610                 615                 620 tgt atc ccg ttc cta gaa aac gat gac tcc aac cgt gcc ctc atg gga   1920
Cys Ile Pro Phe Leu Glu Asn Asp Asp Ser Asn Arg Ala Leu Met Gly
625                 630                 635                 640 gca aac atg caa cgt cag gct gtg cct ttg atg cag ccg gaa gcg ccg   1968
Ala Asn Met Gln Arg Gln Ala Val Pro Leu Met Gln Pro Glu Ala Pro
                645                 650                 655 ttc gtt gga act ggt atg gaa tat gta tca ggt aaa gac tct ggt gcc   2016
Phe Val Gly Thr Gly Met Glu Tyr Val Ser Gly Lys Asp Ser Gly Ala
            660                 665                 670 gct gtt att tgt aaa cac cct ggt atc gtt gaa cgc gta gaa gcg aag   2064
Ala Val Ile Cys Lys His Pro Gly Ile Val Glu Arg Val Glu Ala Lys
        675                 680                 685 aac gtt tgg gtt cgc cgt tat gaa gaa gta gat ggt caa aaa gta aaa   2112
Asn Val Trp Val Arg Arg Tyr Glu Glu Val Asp Gly Gln Lys Val Lys
690                 695                 700 ggg aac ctg gat aaa tac agc atg ctg aaa ttt gtc cgc tcc aac caa   2160
Gly Asn Leu Asp Lys Tyr Ser Met Leu Lys Phe Val Arg Ser Asn Gln
705                 710                 715                 720 ggt act tgc tac aat caa cgt ccg atc gta agt gtc ggc gat gaa gtg   2208
Gly Thr Cys Tyr Asn Gln Arg Pro Ile Val Ser Val Gly Asp Glu Val
                725                 730                 735 gta aaa gga gaa atc ctt gct gac ggt cct tct atg gag ctt ggt gaa   2256
Val Lys Gly Glu Ile Leu Ala Asp Gly Pro Ser Met Glu Leu Gly Glu
            740                 745                 750 ctt gca ctt ggc cgt aac gta atg gtt ggc ttc atg act tgg gat ggc   2304
Leu Ala Leu Gly Arg Asn Val Met Val Gly Phe Met Thr Trp Asp Gly
        755                 760                 765 tac aac tat gag gat gcc atc atc atg agt gaa cgc ttg gtg aag gat   2352
Tyr Asn Tyr Glu Asp Ala Ile Ile Met Ser Glu Arg Leu Val Lys Asp
770                 775                 780 gat gtt tat aca tct atc cac att gaa gaa tat gaa tca gaa gca cgc   2400
Asp Val Tyr Thr Ser Ile His Ile Glu Glu Tyr Glu Ser Glu Ala Arg
785                 790                 795                 800 gat acg aaa ctt gga cct gaa gaa atc act cgc gat att cca aac gtc   2448
Asp Thr Lys Leu Gly Pro Glu Glu Ile Thr Arg Asp Ile Pro Asn Val
```

-continued

```
                    805                 810                 815
ggt gaa gat gcg ctt cgc aat ctt gat gac cgc gga atc atc cgt att      2496
Gly Glu Asp Ala Leu Arg Asn Leu Asp Asp Arg Gly Ile Ile Arg Ile
        820                 825                 830 ggg gca gaa gtg aaa gac gga gat ctt ctt gtt ggt aaa gta acg cct      2544
Gly Ala Glu Val Lys Asp Gly Asp Leu Leu Val Gly Lys Val Thr Pro
            835                 840                 845 aaa ggt gta act gaa ctg act gct gaa gaa cgc ctg ctt cac gcc atc      2592
Lys Gly Val Thr Glu Leu Thr Ala Glu Glu Arg Leu Leu His Ala Ile
850                 855                 860 ttt ggt gaa aag gcc cgc gag gtt cgt gat act tct ctt cgt gtg cct      2640
Phe Gly Glu Lys Ala Arg Glu Val Arg Asp Thr Ser Leu Arg Val Pro
865                 870                 875                 880 cac ggc ggc ggc gga att atc cac gac gtt aaa gtc ttc aat cgt gaa      2688
His Gly Gly Gly Gly Ile Ile His Asp Val Lys Val Phe Asn Arg Glu
                885                 890                 895 gac gga gat gaa ctt cct cca ggc gtt aac cag ttg gta cgt gtg tat      2736
Asp Gly Asp Glu Leu Pro Pro Gly Val Asn Gln Leu Val Arg Val Tyr
            900                 905                 910 atc gtt cag aaa cgt aag att tct gaa ggg gat aaa atg gcc ggt cgt      2784
Ile Val Gln Lys Arg Lys Ile Ser Glu Gly Asp Lys Met Ala Gly Arg
        915                 920                 925 cac ggt aac aaa ggt gtt atc tct aag att ctt cct gaa gag gat atg      2832
His Gly Asn Lys Gly Val Ile Ser Lys Ile Leu Pro Glu Glu Asp Met
    930                 935                 940 cct tac ctt cct gac ggc aca cca att gat atc atg ctt aac ccg ctg      2880
Pro Tyr Leu Pro Asp Gly Thr Pro Ile Asp Ile Met Leu Asn Pro Leu
945                 950                 955                 960 ggc gta cca tca cgt atg aac atc ggg cag gta ttg gag ctc cat atg      2928
Gly Val Pro Ser Arg Met Asn Ile Gly Gln Val Leu Glu Leu His Met
                965                 970                 975 ggt atg gcc gct cgt tat ctc ggc atc cac att gcg tca ccg gta ttt      2976
Gly Met Ala Ala Arg Tyr Leu Gly Ile His Ile Ala Ser Pro Val Phe
            980                 985                 990 gac gga gcg cgt gaa gag gat gtt tgg gaa aca ctt gaa gaa gcc gga      3024
Asp Gly Ala Arg Glu Glu Asp Val Trp Glu Thr Leu Glu Glu Ala Gly
        995                 1000                1005 atg tct cgt gac gcc aaa acg gtt ctt tac gac ggg cgt agc gga           3069
Met Ser Arg Asp Ala Lys Thr Val Leu Tyr Asp Gly Arg Ser Gly
    1010                1015                1020 gag ccg ttt gat aac cgt gta tct gtt ggt att atg tac atg att           3114
Glu Pro Phe Asp Asn Arg Val Ser Val Gly Ile Met Tyr Met Ile
    1025                1030                1035 aaa ctg gct cac atg gtt gac gat aaa ctt cat gcg cgc tct aca           3159
Lys Leu Ala His Met Val Asp Asp Lys Leu His Ala Arg Ser Thr
    1040                1045                1050 ggc cct tac tca ctt gtt acg cag cag cct ctt ggc ggt aaa gcg           3204
Gly Pro Tyr Ser Leu Val Thr Gln Gln Pro Leu Gly Gly Lys Ala
    1055                1060                1065 caa ttt ggc gga cag cgt ttt ggt gag atg gag gtt tgg gca ctt           3249
Gln Phe Gly Gly Gln Arg Phe Gly Glu Met Glu Val Trp Ala Leu
    1070                1075                1080 gaa gct tac ggt gcg gct tac act ctt caa gaa att ctg act gtt           3294
Glu Ala Tyr Gly Ala Ala Tyr Thr Leu Gln Glu Ile Leu Thr Val
    1085                1090                1095 aaa tct gat gac gtg gtt gga cgt gtg aaa aca tac gaa gcc atc           3339
Lys Ser Asp Asp Val Val Gly Arg Val Lys Thr Tyr Glu Ala Ile
    1100                1105                1110 gtt aaa ggc gac aac gtt cct gaa cca gg                                3368
```

-continued

```
Val Lys Gly Asp Asn Val Pro Glu Pro
    1115                1120
```

<210> SEQ ID NO 35
<211> LENGTH: 1122
<212> TYPE: PRT
<213> ORGANISM: Bacillus subtilis

<400> SEQUENCE: 35

```
Leu Thr Gly Gln Leu Val Gln Tyr Gly Arg His Arg Gln Arg Arg Ser
1               5                   10                  15

Tyr Ala Arg Ile Ser Glu Val Leu Glu Leu Pro Asn Leu Ile Glu Ile
            20                  25                  30

Gln Thr Ser Ser Tyr Gln Trp Phe Leu Asp Glu Gly Leu Arg Glu Met
        35                  40                  45

Phe Gln Asp Ile Ser Pro Ile Glu Asp Phe Thr Gly Asn Leu Ser Leu
    50                  55                  60

Glu Phe Ile Asp Tyr Ser Leu Gly Glu Pro Lys Tyr Pro Val Glu Glu
65                  70                  75                  80

Ser Lys Glu Arg Asp Val Thr Tyr Ser Ala Pro Leu Arg Val Lys Val
                85                  90                  95

Arg Leu Ile Asn Lys Glu Thr Gly Glu Val Lys Asp Gln Asp Val Phe
            100                 105                 110

Met Gly Asp Phe Pro Ile Met Thr Asp Thr Gly Thr Phe Ile Ile Asn
        115                 120                 125

Gly Ala Glu Arg Val Ile Val Ser Gln Leu Val Arg Ser Pro Ser Val
    130                 135                 140

Tyr Phe Ser Gly Lys Val Asp Lys Asn Gly Lys Lys Gly Phe Thr Ala
145                 150                 155                 160

Thr Val Ile Pro Asn Arg Gly Ala Trp Leu Glu Tyr Glu Thr Asp Ala
                165                 170                 175

Lys Asp Val Val Tyr Val Arg Ile Asp Arg Thr Arg Lys Leu Pro Val
            180                 185                 190

Thr Val Leu Leu Arg Ala Leu Gly Phe Gly Ser Asp Gln Glu Ile Leu
        195                 200                 205

Asp Leu Val Gly Glu Asn Glu Tyr Leu Arg Asn Thr Leu Asp Lys Asp
    210                 215                 220

Asn Thr Glu Asn Ser Asp Lys Ala Leu Leu Glu Ile Tyr Glu Arg Leu
225                 230                 235                 240

Arg Pro Gly Glu Pro Pro Thr Val Glu Asn Ala Lys Ser Leu Leu Asp
                245                 250                 255

Ser Arg Phe Phe Asp Pro Lys Arg Tyr Asp Leu Ala Asn Val Gly Arg
            260                 265                 270

Tyr Lys Ile Asn Lys Lys Leu His Ile Lys Asn Arg Leu Phe Asn Gln
        275                 280                 285

Arg Leu Ala Glu Thr Leu Val Asp Pro Glu Thr Gly Glu Ile Leu Ala
    290                 295                 300

Glu Lys Gly Gln Ile Leu Asp Arg Arg Thr Leu Asp Lys Val Leu Pro
305                 310                 315                 320

Tyr Leu Glu Ser Gly Ile Gly Phe Arg Lys Leu Tyr Pro Asn Gly Gly
                325                 330                 335

Val Val Glu Asp Glu Val Thr Leu Gln Ser Ile Lys Ile Tyr Ala Pro
            340                 345                 350

Thr Asp Gln Glu Gly Glu Gln Val Ile Asn Val Ile Gly Asn Ala Tyr
        355                 360                 365
```

```
Ile Glu Glu Ile Lys Asn Ile Thr Pro Ala Asp Ile Ser Ser
    370                 375                 380

Ile Ser Tyr Phe Phe Asn Leu Leu His Gly Val Gly Asp Thr Asp Asp
385                 390                 395                 400

Ile Asp His Leu Gly Asn Arg Arg Leu Arg Ser Val Gly Glu Leu Leu
                    405                 410                 415

Gln Asn Gln Phe Arg Ile Gly Leu Ser Arg Met Glu Arg Val Val Arg
                420                 425                 430

Glu Arg Met Ser Ile Gln Asp Thr Asn Thr Ile Thr Pro Gln Gln Leu
        435                 440                 445

Ile Asn Ile Arg Pro Val Ile Ala Ser Ile Lys Glu Phe Phe Gly Ser
    450                 455                 460

Ser Gln Leu Ser Gln Phe Met Asp Gln Thr Asn Pro Leu Ala Glu Leu
465                 470                 475                 480

Thr His Lys Arg Arg Leu Ser Ala Leu Gly Pro Gly Gly Leu Thr Arg
                485                 490                 495

Glu Arg Ala Gly Met Glu Val Arg Asp Val His Tyr Ser His Tyr Gly
                500                 505                 510

Arg Met Cys Pro Ile Glu Thr Pro Glu Gly Pro Asn Ile Gly Leu Ile
        515                 520                 525

Asn Ser Leu Ser Ser Tyr Ala Lys Val Asn Arg Phe Gly Phe Ile Glu
    530                 535                 540

Thr Pro Tyr Arg Arg Val Asp Pro Glu Thr Gly Lys Val Thr Gly Arg
545                 550                 555                 560

Ile Asp Tyr Leu Thr Ala Asp Glu Glu Asp Asn Tyr Val Val Ala Gln
                565                 570                 575

Ala Asn Ala Arg Leu Asp Asp Asp Gly Ser Phe Ile Asp Asp Ser Ile
                580                 585                 590

Ile Ala Arg Phe Arg Gly Glu Asn Thr Val Val Ser Arg Asn Arg Val
        595                 600                 605

Asp Tyr Met Asp Val Ser Pro Lys Gln Val Val Ser Ala Ala Thr Ala
        610                 615                 620

Cys Ile Pro Phe Leu Glu Asn Asp Asp Ser Asn Arg Ala Leu Met Gly
625                 630                 635                 640

Ala Asn Met Gln Arg Gln Ala Val Pro Leu Met Gln Pro Glu Ala Pro
                645                 650                 655

Phe Val Gly Thr Gly Met Glu Tyr Val Ser Gly Lys Asp Ser Gly Ala
                660                 665                 670

Ala Val Ile Cys Lys His Pro Gly Ile Val Glu Arg Val Glu Ala Lys
        675                 680                 685

Asn Val Trp Val Arg Arg Tyr Glu Glu Val Asp Gly Gln Lys Val Lys
        690                 695                 700

Gly Asn Leu Asp Lys Tyr Ser Met Leu Lys Phe Val Arg Ser Asn Gln
705                 710                 715                 720

Gly Thr Cys Tyr Asn Gln Arg Pro Ile Val Ser Val Gly Asp Glu Val
                725                 730                 735

Val Lys Gly Glu Ile Leu Ala Asp Gly Pro Ser Met Glu Leu Gly Glu
        740                 745                 750

Leu Ala Leu Gly Arg Asn Val Met Val Gly Phe Met Thr Trp Asp Gly
        755                 760                 765

Tyr Asn Tyr Glu Asp Ala Ile Ile Met Ser Glu Arg Leu Val Lys Asp
770                 775                 780
```

-continued

```
Asp Val Tyr Thr Ser Ile His Ile Glu Glu Tyr Glu Ser Glu Ala Arg
785                 790                 795                 800

Asp Thr Lys Leu Gly Pro Glu Glu Ile Thr Arg Asp Ile Pro Asn Val
                805                 810                 815

Gly Glu Asp Ala Leu Arg Asn Leu Asp Asp Arg Gly Ile Ile Arg Ile
            820                 825                 830

Gly Ala Glu Val Lys Asp Gly Asp Leu Leu Val Gly Lys Val Thr Pro
        835                 840                 845

Lys Gly Val Thr Glu Leu Thr Ala Glu Glu Arg Leu Leu His Ala Ile
    850                 855                 860

Phe Gly Glu Lys Ala Arg Glu Val Arg Asp Thr Ser Leu Arg Val Pro
865                 870                 875                 880

His Gly Gly Gly Ile Ile His Asp Val Lys Val Phe Asn Arg Glu
                885                 890                 895

Asp Gly Asp Glu Leu Pro Pro Gly Val Asn Gln Leu Val Arg Val Tyr
                900                 905                 910

Ile Val Gln Lys Arg Lys Ile Ser Glu Gly Asp Lys Met Ala Gly Arg
            915                 920                 925

His Gly Asn Lys Gly Val Ile Ser Lys Ile Leu Pro Glu Glu Asp Met
    930                 935                 940

Pro Tyr Leu Pro Asp Gly Thr Pro Ile Asp Ile Met Leu Asn Pro Leu
945                 950                 955                 960

Gly Val Pro Ser Arg Met Asn Ile Gly Gln Val Leu Glu Leu His Met
                965                 970                 975

Gly Met Ala Ala Arg Tyr Leu Gly Ile His Ile Ala Ser Pro Val Phe
            980                 985                 990

Asp Gly Ala Arg Glu Glu Asp Val  Trp Glu Thr Leu Glu  Glu Ala Gly
        995                 1000                1005

Met Ser  Arg Asp Ala Lys Thr  Val Leu Tyr Asp Gly  Arg Ser Gly
    1010                1015                1020

Glu Pro  Phe Asp Asn Arg Val  Ser Val Gly Ile Met  Tyr Met Ile
    1025                1030                1035

Lys Leu  Ala His Met Val Asp  Asp Lys Leu His Ala  Arg Ser Thr
    1040                1045                1050

Gly Pro  Tyr Ser Leu Val Thr  Gln Gln Pro Leu Gly  Gly Lys Ala
    1055                1060                1065

Gln Phe  Gly Gly Gln Arg Phe  Gly Glu Met Glu Val  Trp Ala Leu
    1070                1075                1080

Glu Ala  Tyr Gly Ala Ala Tyr  Thr Leu Gln Glu Ile  Leu Thr Val
    1085                1090                1095

Lys Ser  Asp Asp Val Val Gly  Arg Val Lys Thr Tyr  Glu Ala Ile
    1100                1105                1110

Val Lys  Gly Asp Asn Val Pro  Glu Pro
    1115                1120
```

BACILLUS SUBTILIS SUBSPECIES

CROSS-REFERENCE TO RELATED APPLICATIONS

This application is a 35 U.S.C. 371 national application of international application no. PCT/US2016/014505 filed Jan. 22, 2016 which claims priority or the benefit under 35 U.S.C. 119 of U.S. application Nos. 62/106,841, 62/153,038 and 62/260,800 filed Jan. 23, 2015, Apr. 27, 2015 and Nov. 30, 2015, respectively. The content of each application is fully incorporated herein by reference.

REFERENCE TO A DEPOSIT OF BIOLOGICAL MATERIAL

This application contains a reference to a deposit of biological material, which deposit is incorporated herein by reference.

REFERENCE TO SEQUENCE LISTING

This application contains a Sequence Listing in computer readable form. The computer readable form is incorporated herein by reference.
Index to Sequence Listing:
SEQ ID NO: 1 is the DNA sequence of the gyrB gene from DSM 29870 (obtained as described in Example 3).
SEQ ID NO: 2 is the partial amino acid sequence deduced from the gyrB gene of SEQ ID NO: 1 from DSM 29870.
SEQ ID NO: 3 is the DNA sequence of the rpoB gene from DSM 29870 (obtained as described in Example 4).
SEQ ID NO: 4 is the partial amino acid sequence deduced from the rpoB gene of SEQ ID NO: 3 from DSM 29870.
SEQ ID NO: 5 is the DNA sequence of the gyrA gene (published genome sequence of *Bacillus subtilis* subsp. *Spizizenii* CP002905).
SEQ ID NO: 6 is the partial amino acid sequence deduced from the gyrA gene of SEQ ID NO: 5.
SEQ ID NO: 7 is the DNA sequence of the gyrA gene from DSM 29870.
SEQ ID NO: 8 is the amino acid sequence of gyrA gene product of SEQ ID NO: 7 from DSM 29870.
SEQ ID NO: 9 is the 16S rDNA of DSM 29870.
SEQ ID NO: 10 to SEQ ID NO: 31 are PCR and sequencing primers.
SEQ ID NO: 32 is DNA sequence of GyrB gene from DSM 29870 (obtained from PCR product).
SEQ ID NO: 33 is the partial amino acid sequence deduced from the gyrB gene of SEQ ID NO: 32 from DSM 29870.
SEQ ID NO: 34 is DNA sequence of rpoB gene from DSM 29870 (obtained from PCR product).
SEQ ID NO: 35 is the partial amino acid sequence deduced from the rpoB gene of SEQ ID NO: 34 from DSM 29870.

BACKGROUND OF THE INVENTION

Field of the Invention

The present invention relates to novel subspecies of *Bacillus subtilis*. The novel subspecies can improve health and performance of production animals. In one embodiment the *Bacillus subtilis* subspecies has activity against *Clostridium perfringens* and/or *E. coli*. In a preferred embodiment the *Bacillus subtilis* subspecies has a high compatibility with monensin such as being compatible with at least 2.4 µg/ml monensin as determined in Example 12.

The invention further relates to compositions comprising one or more strains of the *Bacillus subtilis* subspecies and to use of the strain(s) of the *Bacillus subtilis* subspecies in an animal feed.

Background of the Invention

*Bacillus* is a genus of Gram-positive, rod-shaped bacteria and a member of the phylum Firmicutes. *Bacillus* species can be obligate aerobes (oxygen reliant), or facultative anaerobes (having the ability to be aerobic or anaerobic). Ubiquitous in nature, *Bacillus* includes both free-living (non-parasitic) and parasitic pathogenic species. Under stressful environmental conditions, the bacteria can produce oval endospores that are not true spores but which the bacteria can reduce themselves to and remain in a dormant state for very long periods.

*Clostridium perfringens* (*C. perfringens*) is a Gram-positive, rod-shaped, anaerobic, spore-forming bacterium of the genus *Clostridium*. Infections due to *C. perfringens* show evidence of tissue necrosis, bacteremia, emphysematous cholecystitis, and gas gangrene, which is also known as clostridial myonecrosis. *C. perfringens* can also result in polymicrobial anaerobic infections. The incidence of *Clostridium perfringens*-associated necrotic enteritis in poultry has increased in countries that stopped using antibiotic growth promoters. Necrotic enteritis is an enterotoxemic disease that results in significant economic losses in the poultry industry.

There is a need for development of tools and strategies for prevention and control of *C. perfringens* in mono-gastric animals such as poultry. Whilst the vaccination of animals has been suggested, there are challenges associated with vaccinating thousands of animals. Thus discovering a solution which could be administered as an additive in an animal feed would be advantageous.

It is an object of the invention to provide solutions which prevents and/or controls *C. perfringens* in poultry by use of an animal feed comprising one or more one or more bacteria with activity against *Clostridium perfringens*.

A challenge of delivering *Bacillus* spp. in feed is the common use of antibiotics as growth promoters in feed. Therefore it is necessary to determine the compatibility of strains with commonly-used feed antibiotics such as monensin in order to identify any potential conflicts with use as a direct fed microbial. The present invention relates in one embodiment to a *Bacillus subtilis* subspecies with high compatibility with monensin.

DESCRIPTION OF THE RELATED ART

WO 2010/033714 describes a method for enhancing the health of an animal comprising administering to the animal a composition comprising *Bacillus subtilis* QST713.
U.S. Pat. No. 4,919,936 describes a method for increasing the weight gain in animals comprising feeding an animal a probiotic comprising *Bacillus subtilis* C-3102.
Knap et al. describes that *Bacillus licheniformis* has an effect on necrotic enteritis in broiler chickens (Knap et al., 2010, "*Bacillus licheniformis* Prevents Necrotic Enteritis in Broiler Chickens", Avian Diseases 54(2):931-935).

SUMMARY OF THE INVENTION

The present invention relates to a novel subspecies of *Bacillus subtilis*. It has been surprisingly found that the addition of direct fed microbes (DFM) from these *Bacillus* subtilis subspecies to animal feed can be used to prevent and/or control *C. perfringens* infections and/or necrotic enteritis in mono-gastric animal such as pigs and/or poultry.

Thus the invention relates to a *Bacillus subtilis* subspecies or one or more *Bacillus* strain(s) comprising one or more of the features selected from the group consisting of:

i) a gyrB gene with at least 94.7% sequence identity to SEQ ID NO: 1 or a gyrB gene product with at least 99.4% sequence identity to SEQ ID NO: 2;

ii) a rpoB gene with at least 96.6% sequence identity to SEQ ID NO: 3 or an rpoB gene product with at least 99.7% sequence identity to SEQ ID NO: 4;

iii) a gyrA gene with at least 89.5% sequence identity to SEQ ID NO: 7 and/or a gyrA gene product with at least 97.4% sequence identity to SEQ ID NO: 8; and/iv) a genome with an Average Nucleotide Identity to the genome sequence of DSM 29870 of at least 95%. In a preferred embodiment the *Bacillus subtilis* subspecies has a high compatibility with monensin such as being compatible with at least 2.4 μg/ml monensin as determined in Example 12.

The present invention also relates to compositions, such as animal feed or animal feed additives, which comprise one or more *Bacillus* strains of the invention; methods of feeding an animal with the composition of the invention and methods of treating a *Clostridium perfringens* infection or for treating necrotic enteritis in an animal with the composition of the invention. Use of the composition according to the invention to improve the performance of an animal, such as improving the feed conversion rate, improving the body weight gain and/or improving the feed efficiency and/or improving the health is also part of this invention.

The invention further relates to a method for preventing and/or controlling *C. perfringens* infections and/or necrotic enteritis in a mono-gastric animal such as swine or poultry by use of an animal feed, wherein the animal feed comprises the strain having the deposit accession number DSM 29870, wherein the *Bacillus* strain has antimicrobial activity against *Clostridium perfringens* and/or *E. coli.*

In an embodiment, the invention relates to an animal feed that is fed to a mono-gastric animal such as poultry or swine; comprising the strain having the deposit accession number DSM 29870, wherein the *Bacillus* strain has antimicrobial activity against *Clostridium perfringens* and/or *E. coli.*

In a preferred embodiment the invention relates to an animal feed composition such as an animal feed additive comprising a *Bacillus* strain wherein:

i. the *Bacillus* strain has the deposit accession number DSM 29870; a strain having all of the identifying characteristics of *Bacillus* DSM 29870 or a mutant thereof, and ii. the *Bacillus* strain has antimicrobial activity against *Clostridium perfringens* and/or *E. coli.*

In a further aspect, the invention relates to a method for preventing and/or controlling *C. perfringens* infections and/or necrotic enteritis in an animal such as pigs or poultry, comprising the steps of:

(a) feeding an animal such as a pig feed or a poultry feed; and (b) administering to an animal such as pigs or poultry one or more *Bacillus* strains or spores of said strains wherein the strain has the deposit accession number DSM 29870; a strain having all of the identifying characteristics of *Bacillus* DSM 29870 or a mutant thereof, wherein the *Bacillus* strain has antimicrobial activity against *Clostridium perfringens* and/or *E. coli*, and wherein step (a) occurs before, after, or simultaneously with step (b).

In an embodiment, the method relates to an animal feed that is fed to a mono-gastric animal such as pigs and/or poultry. The poultry can, e.g., be chickens and/or broilers and/or layers.

In an embodiment, the animal feed composition comprises one of more additional bacteria; is fed to a mono-gastric animal such as pigs and/or poultry; and further comprises concentrate and/or one or more enzymes and/or one or more additional microbes and/or one or more vitamins and/or one or more minerals and/or one or more amino acids and/or one or more other feed ingredients.

FIGURE LEGENDS

FIG. 1: Core genome phylogram of *Bacillus* species. Note that *B. amyloliquefaciens* subspecies *amyloliquefaciens* and *plantarum* separate with a bootstrap support of 1 (100%).

FIG. 2: Rectangular phylogram with midpoint rooting of the members of the *Bacillus* species. All the draft and completed genomes of *Bacillus subtilis* that were available on NCBI on 29 Dec. 2014 were included in the analysis along with representatives from other species. Numbers indicate bootstrap support (1=100%). Scale bar on top left indicates an evolutionary distance of 0.1 amino acid substitutions per position. See the table for species descriptions.

FIG. 3: Rectangular phylogram of members of *Bacillus* genus. This is a zoomed in view of FIG. 2 to show the relationship of O52BCU (alias strain DSM 29870) to its nearest neighbors.

DEFINITIONS

In general, the terms and phrases used herein have their art-recognized meaning, which can be found by reference to standard texts, journal references, and context known to those skilled in the art. The following definitions are provided to clarify their specific use in context of the disclosure.

As used herein, the singular forms "a", "an" and "the" are intended to include the plural forms as well, unless the context clearly indicates otherwise.

ANI (Average nuclear identity): DNA-DNA hybridization (DDH) has been used traditionally for phylogenetic definition of a species. Based on DDH, strains with greater than 70% relatedness would be considered to belong to the same species [Wayne et al., 1987, Report of the Ad-Hoc-Committee on Reconciliation of Approaches to Bacterial Systematics. *Int J Syst Bacteriol* 37: 463-464]. With the availability of cheap and affordable whole genome sequencing technologies as well as the increased availability of public genomes, whole genome-based species estimation methods are becoming popular as they offer elegant in silico solutions as alternatives DDH methods. ANI is a distance based approach to delineate species based on pair-wise comparisons of genome sequences [Goris et al., 2007, "DNA-DNA hybridization values and their relationship to whole-genome sequence similarities", *Int. J. Syst. Evol. Microbiol.* 57: 81-91]. Goris et al. used 28 different strains to conclude that 95% ANI is similar to the aforementioned 70% DDH cutoff value and can be used for species delineation. ANI has been evaluated in multiple labs and has become the gold standard for species delineation [cf. Kim et al., 2014, "Towards a taxonomic coherence between average nucleotide identity and 16S rRNA gene sequence similarity for species demarcation of prokaryotes", *Int. J. Syst. Evol. Micr.* 64: 346-351; Richter et al., 2009, "Shifting the genomic gold standard for the prokaryotic species definition", *P Natl Acad Sci USA* 106: 19126-19131; and Chan et al., 2012, "Defining bacterial species in the genomic era: insights from the genus *Acinetobacter*", *Bmc. Microbiol.* 12)].

An evaluation of ANI for designation for a strain of *Bacillus amyloliquefaciens* is presented here as an example. ANI calculations were obtained for pair-wise comparisons of *B. amyloliquefaciens* strain FZB42 to members of *B. amyloliquefaciens* subspecies *plantarum*, *B. amyloliquefaciens* subspecies *amyloliquefaciens*, *Bacillus atrophaeus* and *Bacillus subtilis*. The ANI calculator on the Kostas lab website (enve-omics.ce.gatech.edu/ani/newjob) was used. Comparisons with *B. subtilis* strain 160 and *B. atrophaeus* strain C89 give ANI less than 90% indicating that ANI can be successfully used to distinguish between these species (Table A).

method for improved phylogenetic and taxonomic placement of microbes", *Nat. Commun.* 4: 2304] was used to generate a core genome phylogenetic tree. Dendroscope 3 [Huson et al., 2012, "Dendroscope 3: an interactive tool for rooted phylogenetic trees and networks", *Syst. Biol.* 61: 1061-1067] was used to visualize the tree as a rectangular phylogram with midpoint rooting along with bootstrap support (cf. FIG. 1). It is clear that all of the *B. amyloliquefaciens* strains cluster together in one distinct branch; and the *amyloliquefaciens* and *plantarum* subspecies separate into two subclades.

Based on the data presented here, the following species definition could be applied to *B. amyloliquefaciens*: "*Bacillus amyloliquefaciens*" shall mean a monophyletic group of

TABLE A

Pairwise ANI of *B. amyloliquefaciens* FZB42 compared to other bacterial genomes (in percentage).

| | B. subtilis | B. atrophaeus | Amyloliquefaciens subspecies members | | | | Plantarum subspecies members | | | |
|---|---|---|---|---|---|---|---|---|---|---|
| | 168 | C89 | DSM7 | LL3 | TA208 | XH7 | AS43_3 | CAU_B946 | EBL11 | YAU_B9601Y2 |
| FZB42 | 83.08 | 82.31 | 94.52 | 94.44 | 94.44 | 94.46 | 99.08 | 97.91 | 99.00 | 98.52 |

FZB42 shows >95% identify with all members of *B. amyloliquefaciens* subspecies *plantarum*, confirming its species designation. However, FZB42 comparisons to DSM7 and other *amyloliquefaciens* subspecies show an ANI of 94-94.5%, which is less than the acceptable species definition cutoff of 95%. Reciprocal comparison of DSM7 to other genomes also shows >95% ANI within the subspecies *amyloliquefaciens* isolates and 94-95% ANI with subspecies *plantarum* isolates (Table B).

strains that reside in either *amyloliquefaciens* or *plantarum* subspecies branches of a core genome phylogenetic tree and whose genomes exhibit at least 95% pairwise average-nucleotide identity (ANI) [Goris et al., 2007, "DNA-DNA hybridization values and their relationship to whole-genome sequence similarities", *Int J Syst Evol Microbiol* 57: 81-91] when compared to members of the same subspecies and greater than 94% ANI when compared to members of the other subspecies. Alternative definition: "*Bacillus amyloliq-*

TABLE B

Pairwise ANI of *B. amyloliquefaciens* DSM7 compared to other bacterial genomes (in percentage).

| | B. subtilis | B. atrophaeus | amyloliquefaciens subspecies members | | | plantarum subspecies members | | | | |
|---|---|---|---|---|---|---|---|---|---|---|
| | 168 | C89 | LL3 | TA208 | XH7 | AS43_3 | CAU_B946 | EBL11 | FZB42 | YAU_B9601Y2 |
| DSM7 | 82.85 | 82.25 | 99.59 | 99.48 | 99.52 | 94.47 | 94.44 | 94.47 | 94.52 | 94.53 |

Borriss et al. also observed that the DDH between FZB42 and DSM7 varied from 63.7-71.2% which are ranges below the DDH threshold of 70% and is one of the many reasons why they were classified into separate subspecies [Borriss et al., 2011, "Relationship of *Bacillus amyloliquefaciens* clades associated with strains DSM 7(T) and FZB42(T): a proposal for *Bacillus amyloliquefaciens* subsp *amyloliquefaciens* subsp nov and *Bacillus amyloliquefaciens* subsp *plantarum* subsp nov based on complete genome sequence comparisons", *Int. J. Syst. Evol. Micr.* 61: 1786-1801].

Chan et al. recommended complementing ANI with core genome phylogenetics [Chan et al., 2012, "Defining bacterial species in the genomic era: insights from the genus *Acinetobacter*", *Bmc. Microbiol.* 12: 302], where common elements (generally coding sequences or their translations) can be used to derive phylogenetic inferences. To test this, Hyatt et al. [Hyatt et al., 2010 "Prodigal: prokaryotic gene recognition and translation initiation site identification", *BMC Bioinformatics* 11: 119] was used for gene calling and PhyloPhlan [Segata et al., 2013, "PhyloPhlAn is a new

*uefaciens*" shall mean a monophyletic group of strains whose genomes exhibit at least 95% pairwise average-nucleotide identity (ANI) to type strain DSM7 if belonging to subspecies *amyloliquefaciens* or at least 95% pairwise ANI to type strain FZB42 if belonging to subspecies *plantarum*, as inferred by core genome phylogenetics.

Animal feed: The term "animal feed" refers to any compound, preparation, or mixture suitable for, or intended for intake by an animal. Animal feed for a mono-gastric animal comprises concentrates as well as vitamins, minerals, enzymes, amino acids and/or other feed ingredients (such as in a premix). The animal feed may further comprise forage.

Antimicrobial activity against *Clostridium perfringens*: The term "Antimicrobial activity against *Clostridium perfringens*" means that the growth of *Clostridium perfringens* is inhibited and/or that some or all of the *Clostridium perfringens* are killed. This can be determined by the assay described in Example 6.

Blend: the term "blend" means more than one of the bacterial strains described herein.

Body Weight Gain: The Body Weight Gain of an animal is the increase of body weight of the animal over a specified time period.

Composition: The term "composition" refers to a composition comprising a carrier and at least one bacterial strain as described herein. The compositions described herein may be mixed with an animal feed(s) and referred to as a "mash feed."

Concentrates: The term "concentrates" means feed with high protein and energy concentrations, such as fish meal, molasses, oligosaccharides, sorghum, seeds and grains (either whole or prepared by crushing, milling, etc. from, e.g., corn, oats, rye, barley, wheat), oilseed press cake (e.g., from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

Control *C. perfringens* infections and/or necrotic enteritis: The term "control *C. perfringens* infections and/or necrotic enteritis" means a method and/or composition that partly or completely inhibits *C. perfringens* infections and/or necrotic enteritis in an animal. Accordingly, the term "control *C. perfringens* infections and/or necrotic enteritis" means the *C. perfringens* infections and/or the necrotic enteritis is reduced or completely eliminated or prevented.

Direct Fed Microbial: The term "direct fed microbial" means live micro-organisms including spores which, when administered in adequate amounts, confer a benefit, such as improved digestion or health, on the host.

European Production Efficacy Factor (EPEF): The European Production Efficacy Factor is a way of comparing the live-bird performance of flocks. This single-figure facilitates comparison of performance within and among farms and can be used to assess environmental, climatic and managemental variables. The EPEF is calculated as [(liveability (%)× Liveweight (kg))/(Age at depletion (days)×FCR)]×100, wherein livability is the percentage of birds alive at slaughter, Liveweight is the average weight of the birds at slaughter, age of depletion is the age of the birds at slaughter and FCR is the feed conversion ratio at slaughter.

Effective amount/concentration/dosage: The terms "effective amount", "effective concentration", or "effective dosage" are defined as the amount, concentration, or dosage of the bacterial strain(s) sufficient to improve the digestion or yield of an animal or to control *C. perfringens* infections and/or necrotic enteritis. The actual effective dosage in absolute numbers depends on factors including: the state of health of the animal in question, other ingredients present. The "effective amount", "effective concentration", or "effective dosage" of the bacterial strains may be determined by routine assays known to those skilled in the art.

FCR (Feed Conversion Rate): FCR is a measure of an animal's efficiency in converting feed mass into increases of the desired output. Animals raised for meat—such as swine, poultry and fish—the output is the mass gained by the animal. Specifically FCR is the mass of the food eaten divided by the output, all over a specified period.

Feeding an animal: the terms "feeding an animal" or "fed to an animal" means that the composition of the present invention is administered orally to the animal one or more times in an effective amount. The oral administration is typically repeated, e.g., one or more times daily over a specified time period such as several days, one week, several weeks, one months or several months. Accordingly, the term "feeding" or "fed" means any type of oral administration such as administration via an animal feed or via drinking water.

Forage: The term "forage" as defined herein also includes roughage. Forage is fresh plant material such as hay and silage from forage plants, grass and other forage plants, seaweed, sprouted grains and legumes, or any combination thereof. Examples of forage plants are Alfalfa (lucerne), birdsfoot trefoil, *brassica* (e.g., kale, rapeseed (canola), rutabaga (swede), turnip), clover (e.g., alsike clover, red clover, subterranean clover, white clover), grass (e.g., Bermuda grass, brome, false oat grass, fescue, heath grass, meadow grasses, orchard grass, ryegrass, Timothy-grass), corn (maize), millet, barley, oats, rye, sorghum, soybeans and wheat and vegetables such as beets. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Isolated: The term "isolated" means that the one or more bacterial strains described herein are in a form or environment which does not occur in nature, that is, the one or more bacterial strains are at least partially removed from one or more or all of the naturally occurring constituents with which it is associated in nature.

Non-hemolytic: Hemolysis is the breakdown of red blood cells. The ability of bacterial colonies to induce hemolysis when grown on blood agar is used to classify bacterial strains into hemolytic and non-hemolytic strains. In this context hemolysis is defined as described in EFSA Journal 2011; 9(11): 2445, using *Bacillus subtilis* 168 (BGSC-1A1, *Bacillus* Genetic Stock Center) as a negative control. A *Bacillus* strain can be classified as non-hemolytic using the assay described in Example 8.

Pellet: The terms "pellet" and/or "pelleting" refer to solid rounded, spherical and/or cylindrical tablets or pellets and the processes for forming such solid shapes, particularly feed pellets and solid extruded animal feed. As used herein, the terms "extrusion" or "extruding" are terms well known in the art and refer to a process of forcing a composition, as described herein, through an orifice under pressure.

Poultry: The term "poultry" means domesticated birds kept by humans for the eggs they produce and/or their meat and/or their feathers. Poultry includes broilers and layers. Poultry include members of the superorder Galloanserae (fowl), especially the order Galliformes (which includes chickens, Guineafowls, quails and turkeys) and the family Anatidae, in order Anseriformes, commonly known as "waterfowl" and including domestic ducks and domestic geese. Poultry also includes other birds that are killed for their meat, such as the young of pigeons. Examples of poultry include chickens (including layers, broilers and chicks), ducks, geese, pigeons, turkeys and quail.

Prevent *C. perfringens* infections and/or necrotic enteritis: The term "prevent *C. perfringens* infections and/or necrotic enteritis" means a method and/or composition that prevents development of a *C. perfringens* infection and/or necrotic enteritis in an animal.

Roughage: The term "roughage" means dry plant material with high levels of fiber, such as fiber, bran, husks from seeds and grains and crop residues (such as stover, copra, straw, chaff, sugar beet waste).

Sensitive to antibiotics: The term "sensitive to antibiotics" means the phenotypic property of a bacterial strain, that growth of said bacterial strain is inhibited under conditions where the bacterial strain would otherwise grow. In this context sensitivity to antibiotics is tested after the CLSI guidelines (M07-A9 Methods for Dilution Antimicrobial Susceptibility Tests for Bacteria That Grow Aerobically; 2012). The *S. aureus* ATCC 29213 is used as reference strain, which means that it should be included in the test, and that the results are only valid if *S. aureus* ATCC 29213 show results in compliance with the breakpoints of the CLSI guideline (see example Table 5.5) (M100-S24 Performance Standards for Antimicrobial Susceptibility Testing; informational Supplement, 2014). A strain of *Bacillus* is considered sensitive if the growth is detected at or below the breakpoint concentration of the appropriate antibiotic specified in EFSA Journal 2012; 10(6): 2740.

Silage: The term "silage" means fermented, high-moisture stored fodder which can be fed to ruminants (cud-chewing animals such as cattle and sheep) or used as a biofuel feedstock for anaerobic digesters. It is fermented and stored in a process called ensilage, ensiling or silaging, and is usually made from grass or cereal crops (e.g., maize, sorghum, oats, rye, timothy etc forage grass plants),) or legume crops like clovers/trefoils, alfalfa, vetches, using the entire green plant (not just the grain). Silage can be made from many field crops, and special terms may be used depending on type (oatlage for oats, haylage for alfalfa). Silage is made either by placing cut green vegetation in a silo, by piling it in a large heap covered with plastic sheet, or by wrapping large bales in plastic film.

Spore: The terms "spore" and "endospore" are interchangeable and have their normal meaning which is well known and understood by those of skill in the art. As used herein, the term spore refers to a microorganism in its dormant, protected state.

Stable: The term "stable" is a term that is known in the art, and in a preferred aspect, stable is intended to mean the ability of the microorganism to remain in a spore form until it is administered to an animal to improve the health of the animal.

Swine: The term "swine" or "pigs" means domesticated pigs kept by humans for food, such as their meat. Swine includes members of the genus *Sus*, such as *Sus scrofa domesticus* or *Sus domesticus* and include piglets, growing pigs, and sows.

Vegetable protein: The term "vegetable protein" refers to any compound, preparation or mixture that includes at least one protein derived from or originating from a vegetable, including modified proteins and protein-derivatives.

DETAILED DESCRIPTION OF THE INVENTION

It has been surprisingly found that the addition of direct fed microbes (DFM) from *Bacillus* species to animal feed can be used to prevent and/or control *C. perfringens* infections and/or necrotic enteritis in mono-gastric animal such as pigs and/or poultry and at the same time improve the body weight gain and/or feed conversion rate (in challenged and unchallenged chickens).

*Bacillus* Strains of the Invention

The invention relates to the following aspect with respect to *Bacillus subtilis* subspecies and *Bacillus* strain(s):

Aspect 1: A *Bacillus subtilis* subspecies or one or more *Bacillus* strain(s) comprising one or more of the features selected from the group consisting of i) a gyrB gene with at least 94.7% sequence identity to SEQ ID NO: 1 or a gyrB gene product with at least 99.4% sequence identity to SEQ ID NO: 2;

ii) a rpoB gene with at least 96.6% sequence identity to SEQ ID NO: 3 or an rpoB gene product with at least 99.7% sequence identity to SEQ ID NO: 4;

iii) a gyrA gene with at least 89.5% sequence identity to SEQ ID NO: 7 or a gyrA gene product with at least 97.4% sequence identity to SEQ ID NO: 8; and iv) a genome with an Average Nucleotide Identity to the genome sequence of DSM 29870 of at least 95%.

In one embodiment of Aspect 1 the *Bacillus subtilis* subspecies or the one or more *Bacillus* strain(s) comprises a gyrB gene with at least 94.7% sequence identity to SEQ ID NO: 1 such as at least 94.8%, such as at least 95%, such as at least 96%, such as at least 97%, such as at least 98% and such as at least 99% sequence identity.

In one embodiment of Aspect 1 the *Bacillus subtilis* subspecies or the one or more *Bacillus* strain(s) comprises a gyrB gene product with at least 99.4% sequence identity to SEQ ID NO: 2 such as at least 99.5%, such as at least 99.6%, such as at least 99.7%, such as at least 99.8% and such as at least 99.9% sequence identity.

In one embodiment of Aspect 1 the *Bacillus subtilis* subspecies or the one or more *Bacillus* strain(s) comprises an rpoB gene with at least 96.6% sequence identity to SEQ ID NO: 3 such as at least 96.8%, such as at least 97%, such as at least 98% and such as at least 99% sequence identity.

In one embodiment of Aspect 1 the *Bacillus subtilis* subspecies or the one or more *Bacillus* strain(s) comprises an rpoB gene product with at least 99.7% sequence identity to SEQ ID NO: 4 such as at least 99.75%, such as at least 99.8% and such as 99.9% sequence identity.

In one embodiment of Aspect 1 the *Bacillus subtilis* subspecies or the one or more *Bacillus* strain(s) comprises a gyrA gene product with at least 97.4% sequence identity to SEQ ID NO: 8 such as at least 97.6%, such as at least 97.8%, such as at least 98%, such as at least 99% and such as at least 99.5% sequence identity.

In one embodiment of Aspect 1 the *Bacillus subtilis* subspecies or the one or more *Bacillus* strain(s) comprises a gyrA gene with at least 89.5% sequence identity to SEQ ID NO: 7 such as at least 90%, such as at least 91%, such as at least 92%, such as at least 93%, such as at least 94%, such as at least 95%, such as at least 96%, such as at least 97%, such as at least 98% and such as at least 99% sequence identity.

In one embodiment of Aspect 1 the *Bacillus subtilis* subspecies or the one or more *Bacillus* strain(s) comprises a genome with an Average Nucleotide Identity to the genome sequence of DSM 29870 of at least 95%, such as at least 96%, such as at least 97%, such as at least 98%, such as at least 99% sequence identity.

In one embodiment of Aspect 1 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) an rpoB gene with at least 96.6% sequence identity to SEQ ID NO: 3 or an rpoB gene product with at least 99.7% sequence identity to SEQ ID NO: 4.

In one embodiment of Aspect 1 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) a gyrA gene with at least 89.5% sequence identity to SEQ ID NO: 7 or a gyrA gene product with at least 97.4% sequence identity to SEQ ID NO: 8.

In one embodiment of Aspect 1 the *Bacillus subtilis* subspecies or the one or more *Bacillus* strain(s) comprises:
i) a gyrB gene with at least 94.7% sequence identity to SEQ ID NO: 1 or a gyrB gene product with at least 99.4% sequence identity to SEQ ID NO: 2 and
ii) a genome with an Average Nucleotide Identity to the genome sequence of DSM 29870 of at least 95%.

In one embodiment of Aspect 1 the *Bacillus subtilis* subspecies or the one or more *Bacillus* strain(s) comprises:
i) an rpoB gene with at least 96.6% sequence identity to SEQ ID NO: 3 or an rpoB gene product with at least 99.7% sequence identity to SEQ ID NO: 4 and
ii) a gyrA gene with at least 89.5% sequence identity to SEQ ID NO: 7 or a gyrA gene product with at least 97.4% sequence identity to SEQ ID NO: 8.

In one embodiment of Aspect 1 the *Bacillus subtilis* subspecies or the one or more *Bacillus* strain(s) comprises:
i) an rpoB gene with at least 96.6% sequence identity to SEQ ID NO: 3 or an rpoB gene product with at least 99.7% sequence identity to SEQ ID NO: 4 and
ii) a genome with an Average Nucleotide Identity to the genome sequence of DSM 29870 of at least 95%.

In one embodiment of Aspect 1 the *Bacillus subtilis* subspecies or the one or more *Bacillus* strain(s) comprises:
i) a gyrA gene with at least 89.5% sequence identity to SEQ ID NO: 7 or a gyrA gene product with at least 97.4% sequence identity to SEQ ID NO: 8 and
ii) a genome with an Average Nucleotide Identity to the genome sequence of DSM 29870 of at least 95%.

In one embodiment of Aspect 1 the *Bacillus subtilis* subspecies or the one or more *Bacillus* strain(s) comprises:
i) a gyrB gene with at least 94.7% sequence identity to SEQ ID NO: 1 or a gyrB gene product with at least 99.4% sequence identity to SEQ ID NO: 2 and
ii) an rpoB gene with at least 96.6% sequence identity to SEQ ID NO: 3 or an rpoB gene product with at least 99.7% sequence identity to SEQ ID NO: 4 and
iii) a gyrA gene with at least 89.5% sequence identity to SEQ ID NO: 7 or a gyrA gene product with at least 97.4% sequence identity to SEQ ID NO: 8.

In one embodiment of Aspect 1 the *Bacillus subtilis* subspecies or the one or more *Bacillus* strain(s) comprises:
i) a gyrB gene with at least 94.7% sequence identity to SEQ ID NO: 1 or a gyrB gene product with at least 99.4% sequence identity to SEQ ID NO: 2 and
ii) an rpoB gene with at least 96.6% sequence identity to SEQ ID NO: 3 or an rpoB gene product with at least 99.7% sequence identity to SEQ ID NO: 4 and
iii) a genome with an Average Nucleotide Identity to the genome sequence of DSM 29870 of at least 95%.

In one embodiment of Aspect 1 the *Bacillus subtilis* subspecies or the one or more *Bacillus* strain(s) comprises:
i) a gyrB gene with at least 94.7% sequence identity to SEQ ID NO: 1 or a gyrB gene product with at least 99.4% sequence identity to SEQ ID NO: 2 and
ii) a gyrA gene with at least 89.5% sequence identity to SEQ ID NO: 7 or a gyrA gene product with at least 97.4% sequence identity to SEQ ID NO: 8 and
iii) a genome with an Average Nucleotide Identity to the genome sequence of DSM 29870 of at least 95%.

In one embodiment of Aspect 1 the *Bacillus subtilis* subspecies or the one or more *Bacillus* strain(s) comprises:
i) an rpoB gene with at least 96.6% sequence identity to SEQ ID NO: 3 or an rpoB gene product with at least 99.7% sequence identity to SEQ ID NO: 4 and
ii) a gyrA gene with at least 89.5% sequence identity to SEQ ID NO: 7 or a gyrA gene product with at least 97.4% sequence identity to SEQ ID NO: 8 and
iii) a genome with an Average Nucleotide Identity to the genome sequence of DSM 29870 of at least 95%.

In one embodiment of Aspect 1 the *Bacillus subtilis* subspecies or the one or more *Bacillus* strain(s) comprises:
i) a gyrB gene with at least 94.7% sequence identity to SEQ ID NO: 1 or a gyrB gene product with at least 99.4% sequence identity to SEQ ID NO: 2 and
ii) an rpoB gene with at least 96.6% sequence identity to SEQ ID NO: 3 or an rpoB gene product with at least 99.7% sequence identity to SEQ ID NO: 4 and
iii) a gyrA gene with at least 89.5% sequence identity to SEQ ID NO: 7 or a gyrA gene product with at least 97.4% sequence identity to SEQ ID NO: 8 and
iv) a genome with an Average Nucleotide Identity to the genome sequence of DSM 29870 of at least 95%.

In one embodiment, the *Bacillus subtilis* subspecies or the one or more *Bacillus* strain(s) according to Aspect 1 or any of the above embodiments is non-hemolytic (e.g., determined as described in Example 8).

In a preferred embodiment the *Bacillus subtilis* subspecies or the one or more *Bacillus* strain(s) according to Aspect 1 or any of the above embodiments has a high compatibility with monensin such as being compatible with at least 2.3 µg/ml monensin as determined in Example 12. It is even more preferred that the *Bacillus subtilis* subspecies is compatible with at least 2.4 µg/ml monensin as determined in Example 12 (such as at least 2.5 µg/ml monensin as determined in Example 12, such as at least 2.6 µg/ml monensin as determined in Example 12 or such as at least 2.7 µg/ml monensin as determined in Example 12).

In one embodiment, the *Bacillus subtilis* subspecies or the one or more *Bacillus* strain(s) according to Aspect 1 or any of the above embodiments has antimicrobial activity against *Clostridium perfringens*. The effect against *Clostridium perfringens* can be determined as described in Example 6.

In one embodiment, the *Bacillus subtilis* subspecies or the one or more *Bacillus* strain(s) according to Aspect 1 or any of the above embodiments has antimicrobial activity against *E. coli*. The effect against *E. coli* can be determined as described in Example 7.

In one embodiment, the *Bacillus subtilis* subspecies or the one or more *Bacillus* strain(s) according to Aspect 1 or any of the above embodiments has antimicrobial activity against *Clostridium perfringens* and *E. coli*.

In one embodiment, the *Bacillus subtilis* subspecies or the one or more *Bacillus* strain(s) according to Aspect 1 or any of the above embodiments is sensitive to Vancomycin, Clindamycin, Chloramphenicol, Gentamicin, Kanamycin, Streptomycin, Erythromycin and Tetracycline (e.g., as determined as described in Example 9).

In one embodiment, the *Bacillus subtilis* subspecies or the one or more *Bacillus* strain(s) according to Aspect 1 or any of the above embodiments has a 16S rDNA with more than 98% (such as more than 98.5%, such as more than 99%, such as more than 99.5%) sequence identity to SEQ ID NO: 9.

In one embodiment, the *Bacillus subtilis* subspecies or the one or more *Bacillus* strain(s) according to Aspect 1 or any of the above embodiments is a *Bacillus subtilis* strain. The *Bacillus subtilis* subspecies or the one or more *Bacillus* strain(s) according to Aspect 1 or any of the above embodiments is in one embodiment the *Bacillus* strain having deposit accession number DSM 29870, or a strain having all of the identifying characteristics of *Bacillus* DSM 29870 or a mutant thereof that has antimicrobial activity against *Clostridium perfringens*. In a further embodiment, the *Bacillus subtilis* subspecies or the one or more *Bacillus* strain(s) according to Aspect 1 or any of the above embodiments is the *Bacillus* strain having deposit accession number DSM 29870.

The invention relates in one embodiment to a *Bacillus* having deposit accession number DSM 29870 or a strain having all of the identifying characteristics of *Bacillus* DSM 29870 or a mutant thereof. In an embodiment, the invention relates to a *Bacillus* having deposit accession number DSM 29870.

The invention also relates to a biologically pure culture of the *Bacillus* strain according to Aspect 1. In a further embodiment the invention relates to a biologically pure culture of the *Bacillus* strain having deposit accession number DSM 29870 or a strain having all of the identifying characteristics of *Bacillus* DSM 29870 or a mutant thereof. In a further embodiment, the invention relates to a biologically pure culture of the *Bacillus* strain having deposit accession number DSM 29870.

The invention also relates to an isolated *Bacillus* strain according to Aspect 1. In a further embodiment the invention also relates to an isolated *Bacillus* strain having deposit accession number DSM 29870 or an isolated strain having all of the identifying characteristics of *Bacillus* DSM 29870 or a mutant thereof.

The invention also relates to a spore of *Bacillus* strain according to Aspect 1. In a further embodiment the invention also relates to a spore of *Bacillus* strain having deposit accession number DSM 29870 or a spore having all of the identifying characteristics of *Bacillus* DSM 29870 or a mutant thereof. The spore is preferably a stable spore.

Compositions of the Invention

The invention relates to a composition comprising spores (such as stable spores) of the *Bacillus subtilis* subspecies or the one or more *Bacillus* strain(s) according to the invention.

More specifically the invention relates to the following aspects with respect to compositions comprising the *Bacillus subtilis* subspecies or the *Bacillus* strain(s):

Aspect 2: A composition comprising a *Bacillus subtilis* subspecies or one or more *Bacillus* strain(s) comprising one or more of the features selected from the group consisting of:

i) a gyrB gene with at least 94.7% sequence identity to SEQ ID NO: 1 or a gyrB gene product with at least 99.4% sequence identity to SEQ ID NO: 2;

ii) a rpoB gene with at least 96.6% sequence identity to SEQ ID NO: 3 or an rpoB gene product with at least 99.7% sequence identity to SEQ ID NO: 4;

iii) a gyrA gene with at least 89.5% sequence identity to SEQ ID NO: 7 or a gyrA gene product with at least 97.4% sequence identity to SEQ ID NO: 8; and iv) a genome with an Average Nucleotide Identity to the genome sequence of DSM 29870 of at least 95%.

In one embodiment of Aspect 2 the *Bacillus subtilis* subspecies or the one or more *Bacillus* strain(s) comprises a gyrB gene with at least 94.7% sequence identity to SEQ ID NO: 1 such as at least 94.8%, such as at least 95%, such as at least 96%, such as at least 97%, such as at least 98% and such as at least 99% sequence identity.

In one embodiment of Aspect 2 the *Bacillus subtilis* subspecies or the one or more *Bacillus* strain(s) comprises a gyrB gene product with at least 99.4% sequence identity to SEQ ID NO: 2 such as at least 99.5%, such as at least 99.6%, such as at least 99.7%, such as at least 99.8% and such as at least 99.9% sequence identity.

In one embodiment of Aspect 2 the *Bacillus subtilis* subspecies or the one or more *Bacillus* strain(s) comprises an rpoB gene with at least 96.6% sequence identity to SEQ ID NO: 3 such as at least 96.8%, such as at least 97%, such as at least 98% and such as at least 99% sequence identity.

In one embodiment of Aspect 2 the *Bacillus subtilis* subspecies or the one or more *Bacillus* strain(s) comprises an rpoB gene product with at least 99.7% sequence identity to SEQ ID NO: 4 such as at least 99.75%, such as at least 99.8% and such as 99.9% sequence identity.

In one embodiment of Aspect 2 the *Bacillus subtilis* subspecies or the one or more *Bacillus* strain(s) comprises a gyrA gene product with at least 97.4% sequence identity to SEQ ID NO: 8 such as at least 97.6%, such as at least 97.8%, such as at least 98%, such as at least 99% and such as at least 99.5% sequence identity.

In one embodiment of Aspect 2 the *Bacillus subtilis* subspecies or the one or more *Bacillus* strain(s) comprises a gyrA gene with at least 89.5% sequence identity to SEQ ID NO: 7 such as at least 90%, such as at least 91%, such as at least 92%, such as at least 93%, such as at least 94%, such as at least 95%, such as at least 96%, such as at least 97%, such as at least 98% and such as at least 99% sequence identity.

In one embodiment of Aspect 2 the *Bacillus subtilis* subspecies or the one or more *Bacillus* strain(s) comprises a genome with an Average Nucleotide Identity to the genome sequence of DSM 29870 of at least 95%, such as at least 96%, such as at least 97%, such as at least 98%, such as at least 99% sequence identity.

In one embodiment of Aspect 2 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) an rpoB gene with at least 96.6% sequence identity to SEQ ID NO: 3 or an rpoB gene product with at least 99.7% sequence identity to SEQ ID NO: 4.

In one embodiment of Aspect 2 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) a gyrA gene with at least 89.5% sequence identity to SEQ ID NO: 7 or a gyrA gene product with at least 97.4% sequence identity to SEQ ID NO: 8.

In one embodiment of Aspect 2 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) a genome with an Average Nucleotide Identity to the genome sequence of DSM 29870 of at least 95%.

In one embodiment of Aspect 2 the *Bacillus subtilis* subspecies or the one or more *Bacillus* strain(s) comprises:

i) an rpoB gene with at least 96.6% sequence identity to SEQ ID NO: 3 or an rpoB gene product with at least 99.7% sequence identity to SEQ ID NO: 4 and ii) a gyrA gene with at least 89.5% sequence identity to SEQ ID NO: 7 or a gyrA gene product with at least 97.4% sequence identity to SEQ ID NO: 8.

In one embodiment of Aspect 2 the *Bacillus subtilis* subspecies or the one or more *Bacillus* strain(s) comprises:

i) an rpoB gene with at least 96.6% sequence identity to SEQ ID NO: 3 or an rpoB gene product with at least 99.7% sequence identity to SEQ ID NO: 4 and ii) a genome with an Average Nucleotide Identity to the genome sequence of DSM 29870 of at least 95%.

In one embodiment of Aspect 2 the composition comprising a *Bacillus subtilis* subspecies or the one or more *Bacillus* strain(s) comprises:

i) a gyrA gene with at least 89.5% sequence identity to SEQ ID NO: 7 or a gyrA gene product with at least 97.4% sequence identity to SEQ ID NO: 8 and ii) a genome with an Average Nucleotide Identity to the genome sequence of DSM 29870 of at least 95%.

In one embodiment of Aspect 2 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) an rpoB gene with at least 96.6% sequence identity to SEQ ID NO: 3 or an rpoB gene product with at least 99.7% sequence identity to SEQ ID NO: 4 and iii) a gyrA gene with at least 89.5% sequence identity to SEQ ID NO: 7 or a gyrA gene product with at least 97.4% sequence identity to SEQ ID NO: 8.

In one embodiment of Aspect 2 the composition comprising a *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) an rpoB gene with at least 96.6% sequence identity to SEQ ID NO: 3 or an rpoB gene product with at least 99.7% sequence identity to SEQ ID NO: 4 and iii) a genome with an Average Nucleotide Identity to the genome sequence of DSM 29870 of at least 95%.

In one embodiment of Aspect 2 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) a gyrA gene with at least 89.5% sequence identity to SEQ ID NO: 7 or a gyrA gene product with at least 97.4% sequence identity to SEQ ID NO: 8 and iii) a genome with an Average Nucleotide Identity to the genome sequence of DSM 29870 of at least 95%.

In one embodiment of Aspect 2 the *Bacillus subtilis* subspecies or the one or more *Bacillus* strain(s) comprises:

i) an rpoB gene with at least 96.6% sequence identity to SEQ ID NO: 3 or an rpoB gene product with at least 99.7% sequence identity to SEQ ID NO: 4 and ii) a gyrA gene with at least 89.5% sequence identity to SEQ ID NO: 7 or a gyrA gene product with at least 97.4% sequence identity to SEQ ID NO: 8 and iii) a genome with an Average Nucleotide Identity to the genome sequence of DSM 29870 of at least 95%.

In one embodiment of Aspect 2 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 or ii) an rpoB gene with at least 96.6% sequence identity to SEQ ID NO: 3 or an rpoB gene product with at least 99.7% sequence identity to SEQ ID NO: 4 or iii) a gyrA gene with at least 89.5% sequence identity to SEQ ID NO: 7 or a gyrA gene product with at least 97.4% sequence identity to SEQ ID NO: 8 or iv) a genome with an Average Nucleotide Identity to the genome sequence of DSM 29870 of at least 95%.

In one embodiment of Aspect 2 the *Bacillus subtilis* subspecies or the one or more *Bacillus* strain(s) are non-hemolytic (e.g., determined as described in Example 8).

In a preferred embodiment of Aspect 2 the *Bacillus subtilis* subspecies or the one or more *Bacillus* strain(s) has a high compatibility with monensin such as being compatible with at least 2.3 µg/ml monensin as determined in Example 12. It is even more preferred that the *Bacillus subtilis* subspecies is compatible with at least 2.4 µg/ml monensin as determined in Example 12 (such as at least 2.5 µg/ml monensin as determined in Example 12, such as at least 2.6 µg/ml monensin as determined in Example 12 or such as at least 2.7 µg/ml monensin as determined in Example 12).

In one embodiment of Aspect 2 the *Bacillus subtilis* subspecies or the one or more *Bacillus* strain(s) have antimicrobial activity, e.g., against *Clostridium perfringens*. The effect against *Clostridium perfringens* can be determined as described in Example 6.

In one embodiment of Aspect 2 the *Bacillus subtilis* subspecies or the one or more *Bacillus* strain(s) have antimicrobial activity against *E. coli*. The effect against *E. coli* can be determined as described in Example 7.

In one embodiment of Aspect 2 the *Bacillus subtilis* subspecies or the one or more *Bacillus* strain(s) have antimicrobial activity against *Clostridium perfringens* and *E. coli*.

In one embodiment of Aspect 2 the *Bacillus subtilis* subspecies or the one or more *Bacillus* strain(s) is sensitive to Vancomycin, Clindamycin, Chloramphenicol, Gentamicin, Kanamycin, Streptomycin, Erythromycin and Tetracycline (e.g., as determined as described in Example 9).

In one embodiment, the *Bacillus subtilis* subspecies or the one or more *Bacillus* strain(s) according to Aspect 2 or any of the above embodiments has a 16S rDNA with more than 98% (such as more than 98.5%, such as more than 99%, such as more than 99.5%) sequence identity to SEQ ID NO: 9.

In one embodiment, the *Bacillus subtilis* subspecies or the one or more *Bacillus* strain(s) according to Aspect 2 or any of the above embodiments is a *Bacillus subtilis* strain.

In one embodiment, the *Bacillus subtilis* subspecies or the one or more *Bacillus* strain(s) according to Aspect 2 or any of the above embodiments can in one embodiment be the *Bacillus* strain having deposit accession number DSM 29870, or a strain having all of the identifying characteristics of *Bacillus* DSM 29870 or a mutant thereof that has antimicrobial activity against *Clostridium perfringens*.

The invention relates in one embodiment to a composition comprising a *Bacillus* having deposit accession number DSM 29870 or a strain having all of the identifying characteristics of *Bacillus* DSM 29870 or a mutant thereof.

The invention also relates to a composition comprising a biologically pure culture of the *Bacillus* strain according to Aspect 2. In a further embodiment the invention relates to a composition comprising a biologically pure culture of the *Bacillus* strain having deposit accession number DSM 29870 or a strain having all of the identifying characteristics of *Bacillus* DSM 29870 or a mutant thereof.

The invention also relates to a composition comprising an isolated *Bacillus* strain according to Aspect 2. In a further embodiment the invention also relates to a composition comprising an isolated *Bacillus* strain having deposit accession number DSM 29870 or an isolated strain having all of the identifying characteristics of *Bacillus* DSM 29870 or a mutant thereof.

In one embodiment of Aspect 2 the *Bacillus* spores of the composition are present as dried spores (such as, e.g., spray-dried spores). In one embodiment of Aspect 2 the *Bacillus* spores of the composition are present as stable spores. The composition according to Aspect 2 can also be a liquid composition and/or comprise culture supernatant comprising the *Bacillus* strain(s) of the invention.

In one embodiment of Aspect 2 the composition further comprises a carrier. The carrier can comprise one or more of the following compounds: water, glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch, cellulose farigel, cassava cores, sodium aluminium silicate, colloidal amorphous silica, Sipernat 50S, polyethylene glycol 200, polyethylene glycol 400, polyethylene glycol 600, polyethylene glycol 1000, polyethylene glycol 1500, polyethylene glycol 4000 and carbopol.

In a preferred embodiment of Aspect 2 the composition further comprises calcium carbonate and sodium aluminium silicate.

In a preferred embodiment of Aspect 2 the composition further comprises Calcium carbonate, sodium aluminium silicate and sucrose.

In another preferred embodiment of Aspect 2 the composition further comprises one or more carriers such as one or more carriers selected from the group consisting of Calcium carbonate, sodium sulphate, starch, farigel and cassava cores.

In another preferred embodiment of Aspect 2 the composition further comprises one or more flowability agents such as sodium aluminium silicate and/or colloidal amorphous silica (e.g., Sipernat 50S).

In another preferred embodiment of Aspect 2 the composition further comprises one or more binder such as one or more binders selected from the group consisting of sucrose, sorbitol, glycerol, polyethylene glycol 200, polyethylene glycol 400, polyethylene glycol 600, polyethylene glycol 1000, polyethylene glycol 1500, polyethylene glycol 4000, dextrin, maltodextrin and carbopol.

In a preferred embodiment the composition comprises *Bacillus* DSM 29870, calcium carbonate and sodium aluminium silicate.

In a preferred embodiment the composition comprises *Bacillus* DSM 29870, Calcium carbonate, sodium aluminium silicate and sucrose.

In a preferred embodiment the composition comprises *Bacillus* DSM 29870 and one or more carriers such as one or more carriers selected from the group consisting of Calcium carbonate, sodium sulphate, starch, farigel and cassava cores.

In a preferred embodiment the composition comprises *Bacillus* DSM 29870 and one or more flowability agents such as sodium aluminium silicate and/or colloidal amorphous silica (e.g., Sipernat 50S).

In a preferred embodiment the composition comprises *Bacillus* DSM 29870 and one or more binder such as one or more binders selected from the group consisting of sucrose, sorbitol, glycerol, polyethylene glycol 200, polyethylene glycol 400, polyethylene glycol 600, polyethylene glycol 1000, polyethylene glycol 1500, polyethylene glycol 4000, dextrin, maltodextrin and carbopol.

In one embodiment the composition comprises one or more coccidiostats wherein the composition, e.g., is a premix.

In a preferred embodiment the composition according to Aspect 2 the composition comprises from $10^5$ to $10^{12}$ CFU/g of isolated *Bacillus* spores such as from $10^5$ to $10^7$ CFU/g of isolated *Bacillus* spores, such as $10^7$ to $10^9$ CFU/g of isolated *Bacillus* spores, such as from $10^9$ to $10^{11}$ CFU/g of isolated *Bacillus* spores, such as $10^{11}$ to $10^{12}$ CFU/g of isolated *Bacillus* spores or any combination of these intervals.

In yet another preferred embodiment the composition according to Aspect 2 is an animal feed such as an animal feed additive. In one embodiment the animal feed is characterized in that at least 70% (such as at least 80% or at least 90%) of the *Bacillus* spores survive gastric stability in a mono-gastric animal such as chickens.

The composition according to Aspect 2 can be an animal feed which further comprises one or more components selected from the list consisting of: one or more enzymes; one or more additional microbes; one or more vitamins; one or more minerals; one or more amino acids; and one or more other feed ingredients.

The composition according to Aspect 2 can be an animal feed or an animal feed additive wherein the bacterial count of each *Bacillus* spore is $1\times10^3$ and $1\times10^{13}$ CFU/animal/day, preferably between $1\times10^5$ and $1\times10^{11}$ CFU/animal/day, more preferably between $1\times10^6$ and $1\times10^{10}$ CFU/animal/day and most preferably between $1\times10^7$ and $1\times10^9$ CFU/animal/day.

The composition according to Aspect 2 can be a mono-gastric animal feed. The mono-gastric animal can be selected from the group consisting of pigs, swine, piglets, sows, poultry, turkeys, ducks, chicken, broilers, layers, chicks, fish and crustaceans. In one embodiment the animal is not a human being. Mono-gastric animals include in one embodiment, but are not limited to, pigs or swine (including, but not limited to, piglets, growing pigs, and sows); poultry such as turkeys, ducks and chicken (including but not limited to broilers, chicks, layers); horses (including but not limited to hotbloods, coldbloods and warm bloods) and fish (including but not limited to salmon, trout, tilapia, catfish and carps; and crustaceans (including but not limited to shrimps and prawns). Pigs and/or poultry are preferred mono-gastric animals.

In a preferred embodiment, the composition according to Aspect 2 is an animal feed or animal feed additive wherein the *Bacillus* strain improves gut health of chickens with infection of *Clostridium perfringens* by having antimicrobial activity against *Clostridium perfringens*.

In a preferred embodiment, the composition according to Aspect 2 is an animal feed or animal feed additive for treatment of necrotic enteritis or treatment of a *Clostridium perfringens* infection (e.g., for treatment of mono-gastric animals including swine and poultry such as chickens).

In an embodiment to any of the aforementioned embodiments, the *Bacillus* spore kills/inhibits at least 40% (such as at least 45%, at least 50%, at least 60%, at least 70% or at least 80%) of *Clostridium perfringens* after 24 hours, e.g., determined as described in Example 6.

In another embodiment of the invention, the composition such as the animal feed further comprises concentrate. In another embodiment of the invention the composition such as the animal feed further comprises forage. In another embodiment of the invention the composition such as the animal feed further comprises one or more additional microbes. In another embodiment of the invention the composition such as the animal feed further comprises one or more enzymes. In another embodiment of the invention the composition such as the animal feed further comprises one or more vitamins. In another embodiment of the invention the composition such as the animal feed further comprises one or more minerals. In another embodiment of the invention the composition such as the animal feed further comprises one or more amino acids. In another embodiment of the invention the composition such as the animal feed further comprises one or more other feed ingredients.

In an embodiment to any of the aforementioned embodiments, the composition also improves the health of the mono-gastric animal when fed to said animal. In another embodiment to any of the aforementioned embodiments, the composition also increases the egg yield of poultry when fed to said poultry. In an embodiment to any of the aforementioned embodiments, the composition increases the meat yield of the mono-gastric animal when fed to said animal.

In a preferred embodiment, the composition such as the animal feed comprises one or more bacterial strains described herein, wherein the bacterial count of each of the bacterial strains is between $1\times10^4$ and $1\times10^{18}$ CFU/kg of composition, preferably between $1\times10^7$ and $1\times10^{16}$ CFU/kg of composition, more preferably between $1\times10^{10}$ and $1\times10^{15}$ CFU/kg of composition and most preferably between $1\times10^{11}$ and $1\times10^{14}$ CFU/kg of composition.

In a preferred embodiment, the bacterial count of each of the bacterial strains in the animal feed additive is between $1\times10^4$ and $1\times10^{18}$ CFU/kg of composition, preferably between $1\times10^7$ and $1\times10^{16}$ CFU/kg of composition, more preferably between $1\times10^{19}$ and $1\times10^{15}$ CFU/kg of composition and most preferably between $1\times10^{11}$ and $1\times10^{14}$ CFU/kg of dry matter.

In a preferred embodiment, the bacterial count of each of the bacterial strains in the animal feed is between $1\times10^4$ and $1\times10^{14}$ CFU/kg of dry matter, preferably between $1\times10^6$ and $1\times10^{12}$ CFU/kg of dry matter, and more preferably between $1\times10^7$ and $1\times10^{11}$ CFU/kg of dry matter. In a more preferred embodiment the bacterial count of each of the bacterial strains in the animal feed composition is between $1\times10^8$ and $1\times10^{19}$ CFU/kg of dry matter.

In a preferred embodiment, the composition such as the animal feed has a bacterial count of each *Bacillus* spore between $1\times10^3$ and $1\times10^{13}$ CFU/animal/day, preferably between $1\times10^5$ and $1\times10^{11}$ CFU/animal/day, more preferably between $1\times10^6$ and $1\times10^{10}$ CFU/animal/day and most preferably between $1\times10^7$ and $1\times10^9$ CFU/animal/day.

In still yet another embodiment of the invention, the one or more bacterial strains are present in the composition in form of a spore such as a stable spore. In still a further embodiment of the invention, the stable spore will germinate in the intestine and/or stomach of the mono-gastric animal.

In one embodiment, the one or more bacterial strains are stable when subjected to pressures applied/achieved during an extrusion process for pelleting. In a particular embodiment, the one or more bacterial strains are stable at pressures ranging from 1 bar to 40 bar, particularly 10 bar to 40 bar, more particularly 15 bar to 40 bar, even more particularly 20 bar to 40 bar, still even more particularly 35 bar to 37 bar, even still more particularly 36 bar.

In a particular embodiment, the one or more bacterial strains are stable at high temperatures. In particular, the bacterial strains are stable when they are subjected to temperatures achieved during an extrusion process for pelleting. In an even more particular embodiment, the one or more bacterial strains are stable at temperatures ranging from 80° C. to 120° C., particularly temperatures ranging from, 90° C. to 120° C., even more particularly temperatures ranging from 95° C. to 120° C.

In another aspect, the invention relates to a composition such as an animal feed composition comprising a carrier, such as forage and one or more of the bacteria cultures having characteristics substantially identical to that of the strain having the deposit accession number DSM 29870.

In an embodiment, the animal feed composition comprises a carrier and the strain having the deposit accession number DSM 29870, or a strain having all of the identifying characteristics of *Bacillus* DSM 29870 or a mutant thereof.

In another embodiment, the animal feed composition is for feeding to a mono-gastric animal. Mono-gastric animals include, but are not limited to, pigs or swine (including, but not limited to, piglets, growing pigs, and sows); poultry such as turkeys, ducks and chicken (including but not limited to broiler chicks, layers); horses (including but not limited to hotbloods, coldbloods and warm bloods) and fish (including but not limited to salmon, trout, tilapia, catfish and carps; and crustaceans (including but not limited to shrimps and prawns). Pigs and/or poultry are preferred mono-gastric animals.

In an embodiment, the animal feed composition further comprises one or more additional microbes. In a particular embodiment, the animal feed composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a particular embodiment, animal feed composition further comprises a bacterium from one or more of the following strains of *Bacillus amyloliquefaciens, Bacillus subtilis, Bacillus pumilus, Bacillus polymyxa, Bacillus licheniformis, Bacillus megaterium, Bacillus coagulans, Bacillus circulans*, or any combination thereof.

In a particular embodiment, the animal feed composition further comprises one or more types of yeast. The one or more types of yeast can be selected from the group consisting of Saccharomycetaceae, *Saccharomyces* (such as *S. cerevisiae* and/or *S. boulardii*), *Kluyveromyces* (such as *K. marxianus* and *K. lactis*), *Candida* (such as *C. utilis*, also called *Torula* yeast), *Pichia* (such as *P. pastoris*), *Torulaspora* (such as *T. delbrueckii*), *Phaffia* yeasts and *Basidiomycota*.

In an embodiment to any of the aforementioned embodiments the composition further comprises a carrier. The carrier can comprise one or more of the following compounds: water, glycerol, ethylene glycol, 1,2-propylene glycol or 1,3-propylene glycol, sodium aluminium silicate, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch, farigel, cassava cores, colloidal amorphous silica, Sipernat 50S, polyethylene glycol 200, polyethylene glycol 400, polyethylene glycol 600, polyethylene glycol 1000, polyethylene glycol 1500, polyethylene glycol 4000, carbopol. and cellulose.

Animal Feed

In one aspect, the animal feed comprising the *Bacillus subtilis* subspecies or the *Bacillus* strain(s) according to Aspect 1 or the *Bacillus* strain having deposit accession number DSM 29870, or a strain having all of the identifying characteristics of *Bacillus* DSM 29870 or a mutant of DSM 29870 and further comprises one or more of concentrate(s), vitamin(s), mineral(s), enzyme(s), amino acid(s) and/or other feed ingredient(s) (such as in a premix). In a specific embodiment the animal feed further comprises forage.

Forage as defined herein also includes roughage. Forage is fresh plant material such as hay and silage from forage plants, grass and other forage plants, grass and other forage plants, seaweed, sprouted grains and legumes, or any combination thereof. Examples of forage plants are Alfalfa (lucerne), birdsfoot trefoil, *brassica* (e.g., kale, rapeseed (canola), rutabaga (swede), turnip), clover (e.g., alsike clover, red clover, subterranean clover, white clover), grass (e.g., Bermuda grass, brome, false oat grass, fescue, heath grass, meadow grasses, orchard grass, ryegrass, Timothygrass), corn (maize), millet, barley, oats, rye, sorghum, soybeans and wheat and vegetables such as beets. Crops suitable for ensilage are the ordinary grasses, clovers, alfalfa, vetches, oats, rye and maize. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Roughage is generally dry plant material with high levels of fiber, such as fiber, bran, husks from seeds and grains and crop residues (such as stover, copra, straw, chaff, sugar beet waste).

Examples of concentrates are feed with high protein and energy concentrations, such as fish meal, molasses, oligosaccharides, sorghum, seeds and grains (either whole or prepared by crushing, milling, etc. from, e.g., corn, oats, rye, barley, wheat), oilseed press cake (e.g., from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

In one embodiment, the forage and one or more microbes are mixed with a concentrate. In another embodiment, the forage and one or more microbes are mixed with a premix. In a further embodiment, the forage and one or more microbes are mixed with vitamins and/or minerals. In a further embodiment, the forage and one or more microbes are mixed with one or more enzymes. In a further embodiment, the forage and one or more microbes are mixed with other feed ingredients, such as colouring agents, stabilisers, growth improving additives and aroma compounds/flavorings, polyunsaturated fatty acids (PUFAs); reactive oxygen generating species, anti-microbial peptides, anti-fungal polypeptides and amino acids.

In particular embodiments, the animal feed may comprise *Bacillus* stain DSM 29870 or a strain having all of the identifying characteristics of *Bacillus* DSM 29870 or a mutant of DSM 29870 and 0-80% maize; and/or 0-80% sorghum; and/or 0-70% wheat; and/or 0-70% barley; and/or 0-30% oats; and/or 0-40% soybean meal; and/or 0-10% fish meal; and/or 0-20% whey.

The animal feed may comprise *Bacillus* stain DSM 29870 or a strain having all of the identifying characteristics of *Bacillus* DSM 29870 or a mutant of DSM 29870 and vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Chenopodiaceae, e.g., beet, sugar beet, spinach or *quinoa*. Other examples of vegetable protein sources are rapeseed, and cabbage. In another particular embodiment, soybean is a preferred vegetable protein source. Other examples of vegetable protein sources are cereals such as barley, wheat, rye, oat, maize (corn), rice, and sorghum.

In a particular embodiment the animal feed consists of or comprises milk (e.g., from sow), e.g., for feeding of piglets. In another particular embodiment the animal feed consists of or comprises milk replacement, e.g., for feeding of piglets.
Premix In an embodiment, the animal feed may include a premix, comprising, e.g., vitamins, minerals, enzymes, preservatives, antibiotics, other feed ingredients or any combination thereof which are mixed into the animal feed.
Vitamins and Minerals In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, selenium and zinc.

Non-limiting examples of macro minerals include calcium, magnesium, potassium and sodium.
Enzymes In another embodiment, the animal feed compositions or animal feed additive described herein optionally include one or more enzymes. Enzymes can be classified on the basis of the handbook Enzyme Nomenclature from NC-IUBMB, 1992), see also the ENZYME site at the internet: expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch, 2000, The ENZYME database, Nucleic Acids Res. 28: 304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase and alpha-galactosidase, in families based on amino acid sequence similarities has been proposed a few years ago. They currently fall into 90 different families: See the CAZy(ModO) internet site (Coutinho and Henrissat, 1999, Carbohydrate-Active Enzymes server at URL: afmb.cnrs-mrs.fr/-cazy/CAZY/index.html (corresponding papers: Coutinho, P. M. & Henrissat, B. (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12; Coutinho, P. M. & Henrissat, B. (1999) The modular structure of cellulases and other carbohydrate-active enzymes: an integrated database approach. In "Genetics, Biochemistry and Ecology of Cellulose Degradation"., K. Ohmiya, K. Hayashi, K. Sakka, Y. Kobayashi, S. Karita and T. Kimura eds., Uni Publishers Co., Tokyo, pp. 15-23).

Thus the composition of the invention may also comprise at least one other enzyme selected from the group comprising of phytase (EC 3.1.3.8 or 3.1.3.26); xylanase (EC 3.2.1.8); galactanase (EC 3.2.1.89); alpha-galactosidase (EC 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); lysozyme (EC 3.2.1.17); and beta-glucanase (EC 3.2.1.4 or EC 3.2.1.6), or any mixture thereof.

In a particular embodiment, the composition of the invention comprises a phytase (EC 3.1.3.8 or 3.1.3.26). Examples of commercially available phytases include Bio-Feed™ Phytase (Novozymes), Ronozyme® P and HiPhos™ (DSM Nutritional Products), Natuphos™ (BASF), Finase® and Quantum® Blue (AB Enzymes), the Phyzyme® XP (Verenium/DuPont) and Axtra® PHY (DuPont). Other preferred phytases include those described in, e.g., WO 98/28408, WO 00/43503, and WO 03/066847.

In a particular embodiment, the composition of the invention comprises a xylanase (EC 3.2.1.8). Examples of commercially available xylanases include Ronozyme® WX and G2 (DSM Nutritional Products), Econase® XT and Barley (AB Vista), Xylathin® (Verenium) and Axtra® XB (Xylanase/beta-glucanase, DuPont)

In a particular embodiment, the composition of the invention comprises a protease (EC 3.4). Examples of commercially available proteases include Ronozyme® ProAct (DSM Nutritional Products).

Amino Acids

The composition of the invention may further comprise one or more amino acids. Examples of amino acids which are used in animal feed are lysine, alanine, beta-alanine, threonine, methionine and tryptophan.

Other Feed Ingredients

The composition of the invention may further comprise colouring agents, stabilisers, growth improving additives and aroma compounds/flavorings, polyunsaturated fatty acids (PUFAs); reactive oxygen generating species, antimicrobial peptides and anti-fungal polypeptides.

Examples of colouring agents are carotenoids such as beta-carotene, astaxanthin, and lutein.

Examples of aroma compounds/flavorings are creosol, anethol, deca-, undeca- and/or dodeca-lactones, ionones, irone, gingerol, piperidine, propylidene phatalide, butylidene phatalide, capsaicin and tannin.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a synthetase.

The composition of the invention may further comprise at least one amino acid. Examples of amino acids which are used in animal feed are lysine, alanine, beta-alanine, threonine, methionine and tryptophan.

Manufacturing

Animal diets can, e.g., be manufactured as mash feed (non-pelleted) or pelleted feed. Typically, the milled feedstuffs are mixed and sufficient amounts of essential vitamins and minerals are added according to the specifications for the species in question. The bacteria cultures and optionally enzymes can be added as solid or liquid formulations. For example, for mash feed a solid or liquid culture formulation may be added before or during the ingredient mixing step. For pelleted feed the (liquid or solid) culture preparation may also be added before or during the feed ingredient step. Typically a liquid culture preparation comprises the culture of the invention optionally with a polyol, such as glycerol, ethylene glycol or propylene glycol, and is added after the pelleting step, such as by spraying the liquid formulation onto the pellets. The enzyme may also be incorporated in a feed additive or premix.

The enzyme may be added to the feed mix as a granule, which is optionally pelleted or extruded. The granule typically comprises a core particle and one or more coatings, which typically are salt and/or wax coatings. The core particle can either be a homogeneous blend of an active compound optionally together with salts (e.g., organic or inorganic zinc or calcium salt) or an inert particle with an active compound applied onto it. The active compound is the culture of the invention optionally combined with one or more enzymes. The inert particle may be water soluble or water insoluble, e.g., starch, a sugar (such as sucrose or lactose), or a salt (such as NaCl, $Na_2SO_4$). The salt coating is typically at least 1 μm thick and can either be one particular salt or a mixture of salts, such as $Na_2SO_4$, $K_2SO_4$, $MgSO_4$ and/or sodium citrate. Other examples are those described in, e.g., WO 2008/017659, WO 2006/034710, WO 97/05245, WO 98/54980, WO 98/55599, WO 00/70034 or polymer coating such as described in WO 01/00042.

Alternatively, the protease can be prepared by freezing a mixture of liquid culture solution with a bulking agent such as ground soybean meal, and then lyophilizing the mixture.

Methods of Treatment of *C. perfringens* Infections and/or Necrotic Enteritis

In one embodiment, the invention relates to a method for treatment of *C. perfringens* infections and/or necrotic enteritis in an animal such as a mono-gastric animal including poultry using the composition according to Aspect 2. In one embodiment the animal is not a human being. In a further embodiment, animal feed comprising the *Bacillus* strains according to Aspect 1 is fed to a mono-gastric animal in an effective amount. Mono-gastric animals include, but are not limited to, pigs or swine (including, but not limited to, piglets, growing pigs, and sows); poultry such as turkeys, ducks and chicken (including but not limited to broiler chicks, layers); horses (including but not limited to hotbloods, coldbloods and warm bloods) and fish (including but not limited to salmon, trout, tilapia, catfish and carps; and crustaceans (including but not limited to shrimps and prawns). Pigs and/or poultry are preferred mono-gastric animals.

The animal feed can further comprise one or more components selected from the list consisting of concentrate; forage; one or more enzymes; one or more additional microbes; one or more vitamins; one or more minerals; one or more amino acids; and one or more other feed ingredients.

In one embodiment, the method comprises administering to the animal feed the *Bacillus* strains having the deposit accession number DSM 29870 or a strain having all the identifying characteristics of *Bacillus* DSM 29870 or a mutant thereof in an effective amount.

In another embodiment of the method, the animal feed further comprises concentrate. In another embodiment of the method, the animal feed further comprises forage. In another embodiment of the method, the animal feed further comprises one or more additional microbes. In another embodiment of the method, the animal feed further comprises one or more enzymes. In another embodiment of the method, the animal feed further comprises one or more vitamins. In another embodiment of the method, the animal feed further comprises one or more minerals. In another embodiment of the method, the animal feed further comprises one or more amino acids. In another embodiment of the method, the animal feed further comprises one or more other feed ingredients.

In an embodiment to any of the aforementioned embodiments, the method also improves the health of the mono-gastric animal feed. In another embodiment to any of the aforementioned embodiments, the method also increases the egg yield of poultry. In an embodiment to any of the aforementioned embodiments, the method also increases the meat yield of the mono-gastric animal.

In a preferred embodiment, the method comprises administering to a mono-gastric animal one or more bacterial strains described herein, wherein the bacterial count of each of the bacterial strains is between $1\times10^4$ and $1\times10^{14}$ CFU/kg of forage, preferably between $1\times10^6$ and $1\times10^{12}$ CFU/kg of forage, and more preferably between $1\times10^7$ and $1\times10^{11}$ CFU/kg of animal feed. In a more preferred embodiment the bacterial count of each of the bacterial strains described herein is between $1\times10^8$ and $1\times10^{10}$ CFU/kg of animal feed.

In a preferred embodiment, the method comprises administering to a mono-gastric animal one or more bacterial strains described herein, wherein the bacterial count of each of the bacterial strains is between $1\times10^3$ and $1\times10^{13}$ CFU/animal/day, preferably between $1\times10^5$ and $1\times10^{11}$ CFU/animal/day, more preferably between $1\times10^6$ and $1\times10^{10}$ CFU/animal/day and most preferably between $1\times10^7$ and $1\times10^9$ CFU/animal/day.

In another aspect, the invention covers the method for treatment of *C. perfringens* infections comprising:
(a) feeding a mono-gastric animal a feed; and
(b) administering to an animal the strain having the deposit accession number DSM 29870; or a strain having all the identifying characteristics of *Bacillus* DSM 29870 or a mutant thereof;

wherein the *Bacillus* strain antimicrobial activity against *Clostridium perfringens*, and wherein step (a) occurs before, after, or simultaneously with step (b).

In a preferred embodiment of the method, the animal feed is fed to a mono-gastric animal. In an embodiment of the method, the mono-gastric animal is, e.g., pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), or fish (including but not limited to salmon, trout, tilapia, catfish and carps; and crustaceans (including but not limited to shrimps and prawns). Pigs and/or poultry are preferred mono-gastric animals.

In another embodiment of the method, the animal feed further comprises one or more components selected from the list consisting of concentrate; forage; one or more enzymes; one or more additional microbes; one or more vitamins; one or more minerals; one or more amino acids; and one or more other feed ingredients.

In another embodiment of the method, the animal feed further comprises concentrate. In another embodiment of the method, the animal feed further comprises forage. In another embodiment of the method, the animal feed further comprises one or more additional microbes. In another embodiment of the method, the animal feed further comprises one or more enzymes. In another embodiment of the method, the animal feed further comprises one or more vitamins. In another embodiment of the method, the animal feed further comprises one or more minerals. In another embodiment of the method, the animal feed further comprises one or more amino acids. In another embodiment of the method, the animal feed further comprises one or more other feed ingredients.

In still yet another embodiment of the method, the one or more bacterial strains are present in the form of a stable spore. In still a further embodiment of the method, the stable spore will germinate in the rumen of the ruminant.

In a preferred embodiment, the method comprises administering to a mono-gastric animal one or more bacterial strains described herein, wherein the bacterial count of each of the bacterial strains is between $1\times10^4$ and $1\times10^{14}$ CFU/kg of forage, preferably between $1\times10^6$ and $1\times10^{12}$ CFU/kg of forage, and more preferably between $1\times10^7$ and $1\times10^{11}$ CFU/kg of forage. In a more preferred embodiment the bacterial count of each of the bacterial strains described herein is between $1\times10^8$ and $1\times10^{10}$ CFU/kg of forage.

In a preferred embodiment, the method comprises administering to a mono-gastric animal one or more bacterial strains described herein, wherein the bacterial count of each of the bacterial strains is between $1\times10^5$ and $1\times10^{15}$ CFU/animal/day, preferably between $1\times10^7$ and $1\times10^{13}$ CFU/animal/day, and more preferably between $1\times10^8$ and $1\times10^{12}$ CFU/animal/day. In a more preferred embodiment the bacterial count of each of the bacterial strains described herein is between $1\times10^9$ and $1\times10^{11}$ CFU/animal/day.

In a preferred embodiment, the method comprises administering to a mono-gastric animal one or more bacterial strains described herein, wherein the bacterial count of each *Bacillus* spore is between $1\times10^5$ and $1\times10^{15}$ CFU/animal/day, preferably between $1\times10^7$ and $1\times10^{13}$ CFU/animal/day, and more preferably between $1\times10^8$ and $1\times10^{12}$ CFU/animal/day.

The invention relates in a further embodiment to use of the animal feed composition to improve one or more performance parameters in an animal, wherein the performance parameters are selected from the list consisting of improving the feed conversion ratio, improving the body weight gain, improving the feed efficiency, improving the European Production Efficacy Factor and improving the health.

Preferred Embodiments

Preferred embodiments of the invention are described in the set of items herein below (ITEM SET I and ITEM SET II).

Item Set I:

1. A *Bacillus* strain comprising one or more of the features selected from the group consisting of:
   i) a gyrB gene with at least 94.7% sequence identity to SEQ ID NO: 1 or a gyrB gene product with at least 99.4% sequence identity to SEQ ID NO: 2 and/or
   ii) an rpoB gene with at least 96.6% sequence identity to SEQ ID NO: 3 or an rpoB gene product with at least 99.7% sequence identity to SEQ ID NO: 4 and/or
   iii) a gyrA gene with at least 89.5% sequence identity to SEQ ID NO: 7 or a gyrA gene product with at least 97.4% sequence identity to SEQ ID NO: 8 and/or
   iv) a genome with an Average Nucleotide Identity to the genome sequence of DSM 29870 of at least 95%.

2. A *Bacillus* strain comprising:
   i) a gyrB gene with at least 94.7% sequence identity to SEQ ID NO: 1 or a gyrB gene product with at least 99.4% sequence identity to SEQ ID NO: 2 and
   ii) an rpoB gene with at least 96.6% sequence identity to SEQ ID NO: 3 or an rpoB gene product with at least 99.7% sequence identity to SEQ ID NO: 4.

3. A *Bacillus* strain comprising:
   i) a gyrB gene with at least 94.7% sequence identity to SEQ ID NO: 1 or a gyrB gene product with at least 99.4% sequence identity to SEQ ID NO: 2 and
   ii) a gyrA gene with at least 89.5% sequence identity to SEQ ID NO: 7 or a gyrA gene product with at least 97.4% sequence identity to SEQ ID NO: 8.

4. A *Bacillus* strain comprising:
   i) a gyrB gene with at least 94.7% sequence identity to SEQ ID NO: 1 or a gyrB gene product with at least 99.4% sequence identity to SEQ ID NO: 2 and
   ii) a genome with an Average Nucleotide Identity to the genome sequence of DSM 29870 of at least 95%.

5. A *Bacillus* strain comprising:
   i) an rpoB gene with at least 96.6% sequence identity to SEQ ID NO: 3 or an rpoB gene product with at least 99.7% sequence identity to SEQ ID NO: 4 and
   ii) a gyrA gene with at least 89.5% sequence identity to SEQ ID NO: 7 or a gyrA gene product with at least 97.4% sequence identity to SEQ ID NO: 8.

6. A *Bacillus* strain comprising:
   i) an rpoB gene with at least 96.6% sequence identity to SEQ ID NO: 3 or an rpoB gene product with at least 99.7% sequence identity to SEQ ID NO: 4 and
   ii) a genome with an Average Nucleotide Identity to the genome sequence of DSM 29870 of at least 95%.

7. A *Bacillus* strain comprising:
   i) a gyrA gene with at least 89.5% sequence identity to SEQ ID NO: 7 or a gyrA gene product with at least 97.4% sequence identity to SEQ ID NO: 8 and
   ii) a genome with an Average Nucleotide Identity to the genome sequence of DSM 29870 of at least 95%.

8. A *Bacillus* strain comprising:
   i) a gyrB gene with at least 94.7% sequence identity to SEQ ID NO: 1 or a gyrB gene product with at least 99.4% sequence identity to SEQ ID NO: 2 and
   ii) an rpoB gene with at least 96.6% sequence identity to SEQ ID NO: 3 or an rpoB gene product with at least 99.7% sequence identity to SEQ ID NO: 4 and
   iii) a gyrA gene with at least 89.5% sequence identity to SEQ ID NO: 7 or a gyrA gene product with at least 97.4% sequence identity to SEQ ID NO: 8.

9. A *Bacillus* strain comprising:
   i) a gyrB gene with at least 94.7% sequence identity to SEQ ID NO: 1 or a gyrB gene product with at least 99.4% sequence identity to SEQ ID NO: 2 and
   ii) an rpoB gene with at least 96.6% sequence identity to SEQ ID NO: 3 or an rpoB gene product with at least 99.7% sequence identity to SEQ ID NO: 4 and
   iii) a genome with an Average Nucleotide Identity to the genome sequence of DSM 29870 of at least 95%.

10. A *Bacillus* strain comprising:
    i) a gyrB gene with at least 94.7% sequence identity to SEQ ID NO: 1 or a gyrB gene product with at least 99.4% sequence identity to SEQ ID NO: 2 and
    ii) a gyrA gene with at least 89.5% sequence identity to SEQ ID NO: 7 or a gyrA gene product with at least 97.4% sequence identity to SEQ ID NO: 8 and
    iii) a genome with an Average Nucleotide Identity to the genome sequence of DSM 29870 of at least 95%.

11. A *Bacillus* strain comprising:
    i) an rpoB gene with at least 96.6% sequence identity to SEQ ID NO: 3 or an rpoB gene product with at least 99.7% sequence identity to SEQ ID NO: 4 and
    ii) a gyrA gene with at least 89.5% sequence identity to SEQ ID NO: 7 or a gyrA gene product with at least 97.4% sequence identity to SEQ ID NO: 8 and
    iii) a genome with an Average Nucleotide Identity to the genome sequence of DSM 29870 of at least 95%.

12. The *Bacillus* strain according to item 1, wherein the *Bacillus* strain comprises:
    i) a gyrB gene with at least 94.7% sequence identity to SEQ ID NO: 1 or a gyrB gene product with at least 99.4% sequence identity to SEQ ID NO: 2 and
    ii) an rpoB gene with at least 96.6% sequence identity to SEQ ID NO: 3 or an rpoB gene product with at least 99.7% sequence identity to SEQ ID NO: 4 and
    iii) a gyrA gene with at least 89.5% sequence identity to SEQ ID NO: 7 or a gyrA gene product with at least 97.4% sequence identity to SEQ ID NO: 8 and
    iv) a genome with an Average Nucleotide Identity to the genome sequence of DSM 29870 of at least 95%.

13. The *Bacillus* strain according to any of the previous items, wherein the *Bacillus* strain is non-hemolytic, e.g., as determined in Example 8.

14. The *Bacillus* strain according to any of the previous items, wherein the *Bacillus* strain has antimicrobial activity.

15. The *Bacillus* strain according to any of the previous items, wherein the *Bacillus* strain has antimicrobial activity against *Clostridium perfringens*, e.g., as determined in Example 6.

16. The *Bacillus* strain according to any of the previous items, wherein the *Bacillus* strain has antimicrobial activity against *E. coli*, e.g., as determined in Example 7.

17. The *Bacillus* strain according to any of the previous items, wherein the *Bacillus* strain is sensitive to Vancomycin, Clindamycin, Chloramphenicol, Gentamicin, Kanamycin, Streptomycin, Erythromycin and Tetracyclin, e.g., as determined in Example 9.

18. The *Bacillus* strain according to any of the previous items, wherein the *Bacillus* strain has a high compatibility with monensin such as being compatible with at least 2.3 µg/ml monensin as determined in Example 12 (such as at least 2.4 µg/ml monensin, such as at least 2.5 µg/ml monensin, such as at least 2.6 µg/ml monensin or such as at least 2.7 µg/ml monensin as determined in Example 12).

19. The *Bacillus* strain according to any of the previous items, wherein the *Bacillus* strain has a 16S rDNA with more than 98% sequence identity to SEQ ID NO: 9.

20. The *Bacillus* strain according to any of the previous items, wherein the *Bacillus* strain is a *Bacillus subtilis* strain.

21. The *Bacillus* strain according to any of the previous items, wherein the *Bacillus* strain is the *Bacillus* strain having deposit accession number DSM 29870 or a mutant thereof that has antimicrobial activity against *Clostridium perfringens*.

22. A *Bacillus* having deposit accession number DSM 29870 or a strain having all of the identifying characteristics of *Bacillus* DSM 29870 or a mutant thereof.

23. A composition comprising spores of a *Bacillus* strain according to any of items 1 to 22.

24. The composition according to item 23, wherein the *Bacillus* spores of the composition are present as dried spores.

25. The composition according to any of items 23 to 24 which further comprises a carrier.

26. The composition according to item 25, wherein the carrier comprises one or more of the following compounds: water, glycerol, ethylene glycol, 1,2-propylene glycol or 1,3-propylene glycol, sodium aluminium silicate, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch, farigel, cassava cores, colloidal amorphous silica, Sipernat 50S, polyethylene glycol 200, polyethylene glycol 400, polyethylene glycol 600, polyethylene glycol 1000, polyethylene glycol 1500, polyethylene glycol 4000, carbopol and cellulose.

27. The composition according to any of items 23 to 26, wherein the composition comprises from $10^5$ to $10^{12}$ CFU/g of isolated *Bacillus* spores.

28. An animal feed or an animal feed additive comprising the composition of any of items 23 to 27.

29. The animal feed or animal feed additive of item 28, wherein at least 70% (such as at least 80% or at least 90%) of the *Bacillus* spores survive gastric stability in a mono-gastric animal such as chickens.

30. The animal feed or animal feed additive of any of items 28 to 29 which further comprises one or more components selected from the list consisting of:
one or more enzymes;
one or more additional microbes;
one or more vitamins;
one or more minerals;
one or more amino acids; and
one or more other feed ingredients.

31. The animal feed or animal feed additive of any of items 28 to 30, wherein the bacterial count of each *Bacillus* spore is $1 \times 10^4$ and $1 \times 10^{18}$ CFU/kg of composition, preferably between $1 \times 10^6$ and $1 \times 10^{16}$ CFU/kg of composition, and more preferably between $1 \times 10^8$ and $1 \times 10^{14}$ CFU/kg of composition.

32. The animal feed or animal feed additive of any of items 28 to 31, wherein the animal feed composition is a mono-gastric animal feed.

33. The animal feed or animal feed additive of any of items 28 to 32, wherein the animal feed or animal feed additive improves gut health of chickens with infection of *Clostridium perfringens* by having antimicrobial activity against *Clostridium perfringens*.

34. The mono-gastric animal feed according to item 32, wherein the mono-gastric animal is selected from the group consisting of pigs, swine, piglets, sows, poultry, turkeys, ducks, chicken, broilers, layers, chicks, fish and crustaceans.

35. The composition according to any of items 23 to 34 for treatment of necrotic enteritis or treatment of a *Clostridium perfringens* infection.

36. The composition according to item 35 for treatment of mono-gastric animals.

37. A method of treating a *Clostridium perfringens* infection or for treating necrotic enteritis in one or more animals comprising administrating to the one or more animals the composition of any of items 23 to 36 to the animal.

38. Use of the composition according to any of items 23 to 27 or the animal feed or animal feed additive of any of claims 28 to 33 to improve one or more performance parameters in an animal, wherein the performance parameters are selected from the list consisting of improving the feed conversion ratio, improving the body weight gain, improving the feed efficiency, improving the European Production Efficacy Factor and improving the health.

39. A biologically pure culture of the *Bacillus* strain according to any of items 1 to 22.

40. An isolated *Bacillus* strain according to any of items 1 to 22.

41. An isolated *Bacillus* strain selected from the group consisting of *Bacillus* strain DSM 29870, a strain having all of the identifying characteristics of *Bacillus* DSM 29870 and a mutant thereof.

42. The isolated *Bacillus* strain according to item 41, wherein the identifying characteristics can one or more (such as all) of the characteristics selected from the group consisting of
i) non-hemolytic, e.g., as determined in Example 8,
ii) antimicrobial activity against *Clostridium perfringens*, e.g., as determined in Example 6,
iii) antimicrobial activity against *E. coli*, e.g., as determined in Example 7,
iv) sensitive to Vancomycin, Clindamycin, Chloramphenicol, Gentamicin, Kanamycin, Streptomycin, Erythromycin and Tetracyclin, e.g., as determined in Example 9, and
v) high compatibility with monensin such as being compatible with at least 2.3 µg/ml monensin as determined in Example 12 (such as at least 2.4 µg/ml monensin, such as at least 2.5 µg/ml monensin, such as at least 2.6 µg/ml monensin or such as at least 2.7 µg/ml monensin as determined in Example 12).

43. The *Bacillus* strain according to any of items 1 to 22, the composition according to any of items 23 to 27 or the animal feed or animal feed additive of any of claims 28 to 33 for treatment of a *Clostridium perfringens* infection and/or for treatment of necrotic enteritis in one or more animals.

Item Set II:

1. A *Bacillus* strain comprising one or more of the features selected from the group consisting of:
   i) a gyrB gene with at least 94.7% sequence identity to SEQ ID NO: 1 or a gyrB gene product with at least 99.4% sequence identity to SEQ ID NO: 2;
   ii) an rpoB gene with at least 96.6% sequence identity to SEQ ID NO: 3 or an rpoB gene product with at least 99.7% sequence identity to SEQ ID NO: 4; and
   iii) a genome with an Average Nucleotide Identity to the genome sequence of DSM 29870 of at least 95%.

2. The *Bacillus* strain according to item 1, wherein the *Bacillus* strain is non-hemolytic and/or is compatible with monensin (such as with at least 2.4 µg/ml monensin as determined in Example 12).

3. The *Bacillus* strain according to any of the previous items, wherein the *Bacillus* strain has antimicrobial activity against *Clostridium perfringens* or *E. coli*.
4. The *Bacillus* strain according to any of the previous items, wherein the *Bacillus* strain is sensitive to Vancomycin, Clindamycin, Chloramphenicol, Gentamicin, Kanamycin, Streptomycin, Erythromycin and Tetracyclin.
5. The *Bacillus* strain according to any of the previous items, wherein the *Bacillus* strain has a 16S rDNA with more than 98% sequence identity to SEQ ID NO: 9.
6. The *Bacillus* strain according to any of the previous items, wherein the *Bacillus* strain is a *Bacillus subtilis* strain.
7. A *Bacillus* having deposit accession number DSM 29870 or a strain having all of the identifying characteristics of *Bacillus* DSM 29870 or a mutant thereof.
8. A composition comprising spores of a *Bacillus* strain according to any of items 1 to 7.
9. The composition according to item 8 which further comprises a carrier.
10. The composition according to item 9, wherein the carrier comprises one or more of the following compounds: glycerol, ethylene glycol, 1,2-propylene glycol, 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose.
11. The composition according to any of items 8 to 10, wherein the composition comprises from $10^5$ to $10^{12}$ CFU/g of isolated *Bacillus* spores.
12. The composition according to any of items 8 to 11, wherein the composition is an animal feed or animal feed additive.
13. The composition according to any of items 8 to 11 for treatment of necrotic enteritis or treatment of a *Clostridium perfringens* infection.
14. A method of treating a *Clostridium perfringens* infection or for treating necrotic enteritis in one or more animals comprising administrating the composition according to any of items 8 to 13 to the animals.
15. Use of the composition according to any of items 8 to 13 to improve one or more performance parameters in an animal, wherein the performance parameters are selected from the list consisting of improving the feed conversion ratio, improving the body weight gain, improving the feed efficiency, improving the European Production Efficacy Factor and improving the health.

EXAMPLES

Example 1: Identification, Characterization and Deposit of the Biological Material The following biological material was deposited under the terms of the Budapest Treaty at Leibniz-Institut DSMZ-Deutsche Sammlung von Mikro-organismen and Zellkulturen GmbH, Inhoffenstraße 7 B, 38124 Braunschweig Germany, and given the following accession number:

TABLE 1.1

| Deposit of Biological Material | | |
|---|---|---|
| Identification | Accession Number | Date of Deposit |
| *Bacillus subtilis* | DSM 29870 | Jan. 12, 2015 |

*Bacillus subtilis* DSM 29870 was isolated by Novozymes (Novo Nordisk) from an environmental sample collected at Jamaica in 1990. The strain was identified as *Bacillus subtilis* based on 16S rDNA sequencing.

The strain has been deposited under conditions that assure that access to the culture will be available during the pendency of this patent application to one determined by foreign patent laws to be entitled thereto. The deposits represent a substantially pure culture of the deposited strain. The deposits are available as required by foreign patent laws in countries wherein counterparts of the subject application or its progeny are filed. However, it should be understood that the availability of a deposit does not constitute a license to practice the subject invention in derogation of patent rights granted by governmental action.

Sequencing of 16S rDNA Gene

DNA was extracted from a culture of DSM 29870 using QiaAmp DNA Blood Mini Kit (Qiagen art 51106). The kit was used as recommended for extraction of DNA from gram positive bacteria.

16S rDNA was amplified in a total volume of 50 µl by mixing: 10 pmol of each of Primer 16S-F and 16S-R (Table 1.2), 0.2 mM of each nucleotide, 2.5 units Ampli taq, 1× Ampli taq buffer and 5 µl DNA template.

The following PCR program: 94° C. min 2 min (94° C. 30 s, 52° C. 30 s, 72° C. 1 min)×35, 72° C. 10 min was applied on a Perkin Elmer PCR machine. PCR product was sequenced using primer 794-R, 357-F, 1390-R and 1000-F (Table 1.2) on an ABI Prism sequencer.

TABLE 1.2

| Primers: | | |
|---|---|---|
| Primer | Sequence[1] | SEQ ID NO: |
| 16S-F | 5'-GAGTTTGATCCTGGCTCAG-3' | SEQ ID NO: 10 |
| 16S-R | 5'-AGAAAGGAGGTGATCCAGCC-3' | SEQ ID NO: 11 |
| 794-R | 5'-ATCTAATCCTGTTTGCTCCCC-3' | SEQ ID NO: 12 |
| 357-F | 5'-TACGGGAGGCAGCAG-3' | SEQ ID NO: 13 |
| 1390-R | 5'-CGGTGTGTRCAAGGCCC-3' | SEQ ID NO: 14 |
| 1000-F | 5'-CAACGAGCGCAACCCT-3' | SEQ ID NO: 15 |

[1]Degeneration of primer: R is A or G.

The 16 S rDNA sequence is shown in SEQ ID NO: 9, the sequence was analysed by BLAST against EMBL database and showed identity to 16 S rDNA sequences of *Bacillus subtilis*.

Example 2: Whole Genome Sequencing and Taxonomic Placement of *Bacillus* Strain DSM 29870

Summary

Average nuclear identity (ANI) and phylogenetics, reveal that the *Bacillus* strain DSM 29870 is a novel subspecies of *Bacillus subtilis*.

Materials and Methods:

Genome Sequencing of DSM 29870

DNA was extracted from a culture of DSM 29870 using QiaAmp DNA Blood Mini Kit (Qiagen art 51106). The kit was used as recommended for extraction of DNA from gram positive bacteria. Genomic DNA was fragmented using a Covaris M220™ ultrasonicator (Covaris, Inc., Woburn, Mass.) and was used to generate TruSeq™ library ((Illumina, Inc., San Diego, Calif.) using the Apollo 324™ library prep system (Wafergen Biosystems, Inc., Fremont, Calif.). The prepared libraries were sequenced using a MiSeq desktop sequencer (Illumina, Inc., San Diego, Calif.) with MiSeq Reagent Kit v3 (600 cycles) to generate ~360 bp forward and 240 bp reverse paired end reads. Sequences were trimmed and denovo assembled in CLC Genomics Workbench 7.0.4 (CLC Bio, Aarhus, Denmark) using the respective modules.

The following main trimming parameters were used: Ambiguous trim=Yes, Ambiguous limit=2, Quality trim=Yes, Quality Limit=0.01, Minimum number of nucleotides=50, Save broken pairs=Yes. The following main denovo assembly parameters were used: Mapping mode=Map reads back to contigs, Update contigs=Yes, Automatic bibble size=Yes, Minimum contig length=200, Perform scaffolding=yes, Mismatch cost=2, Insertion cost=3, Deletion cost=3, Length fraction=0.8, Similarity graction=0.95.

Benchmark Genome Sequences:

Complete and draft genomes of the public *Bacillus* strains were downloaded from NCBI genomes on Dec. 29, 2014.

Core Genome Phylogenetics:

Prodigal version 2.6 [Hyatt et al., 2010, Prodigal: prokaryotic gene recognition and translation initiation site identification; *BMC Bioinformatics* 11: 119] was used to determine protein sequences.

PhyloPhlan [Segata et al., 2013, PhyloPhlAn is a new method for improved phylogenetic and taxonomic placement of microbes, Nat. Commun. 4: 2304] was used to generate a core genome phylogenetic tree based on phylogenetic signals from 400 most conserved protein sequences.

Figure 3:
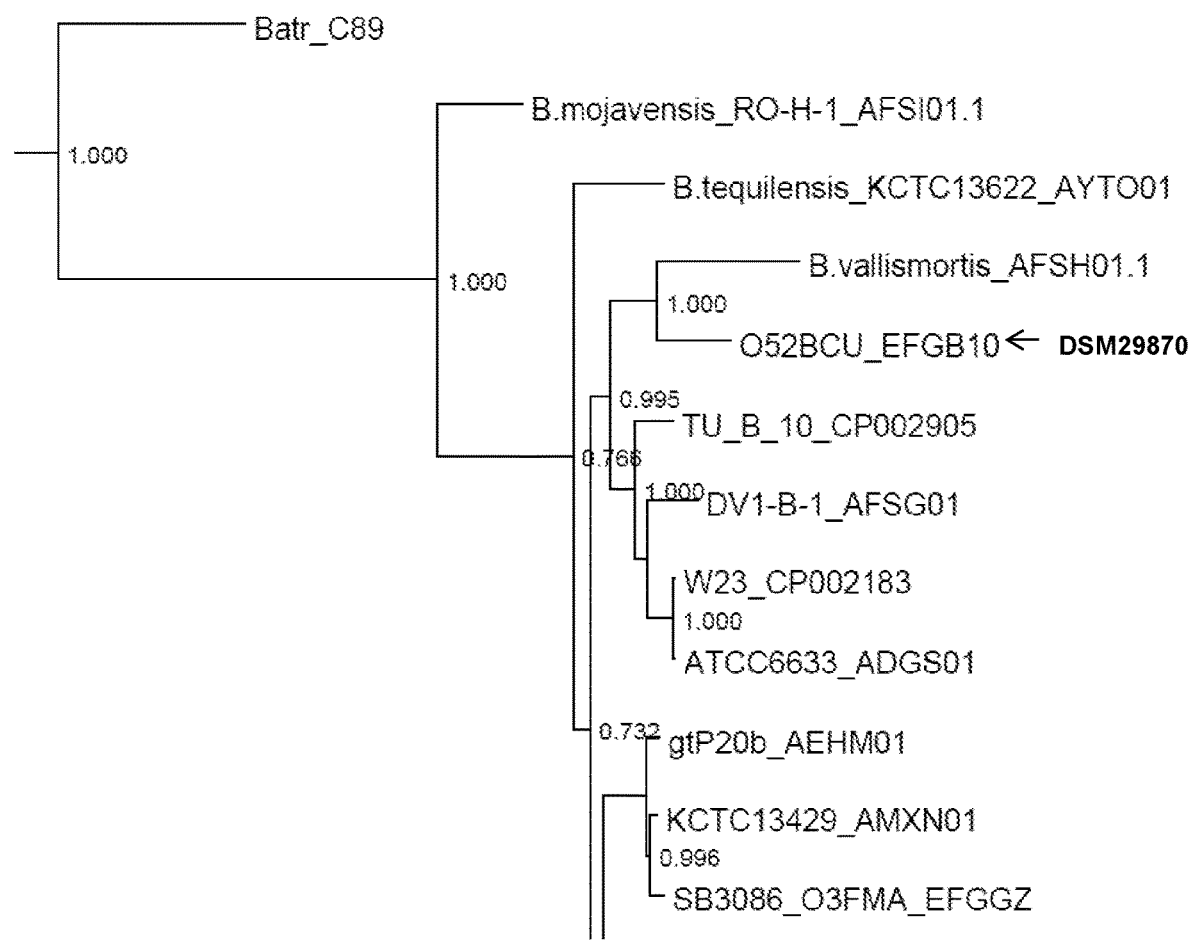

Dendroscope 3 [Huson et al., 2-12. Dendroscope 3: an interactive tool for rooted phylogenetic trees and networks, Syst. Biol. 61: 1061-1067] was used to visualize the tree as a rectangular phylogram with midpoint rooting along with bootstrap support (FIG. 3).

Example of PhyloPhlan Script Execution

./phylophlan.py -nproc 14 -u Protein_files

The newick file generated in output folder was then used as an input for Dendroscope 3 for midpoint rooting and the image was exported in the desired format after the font sizes were adjusted and the desired tree rendering method was selected.

Ani Estimations:

Fasta files of the genomes of each strain were compared pairwise using ani.rb.

Example of ani Script Execution:

ruby./ani.rb -1 O52BCU_EFGB10.fasta -2 RO_NN-1_CP002906.fasta

The results were output on screen and copied into word document and then summarized as a table.

Results and Discussion:

Ani Estimations:

Average nuclear identity (ANI) is a distance based approach to delineate species based on pair-wise comparisons of genome sequences [Goris et al., 2007, "DNA-DNA hybridization values and their relationship to whole-genome sequence similarities", *Int. J. Syst. Evol. Microbiol.* 57: 81-91]. See the definition of ANI for further details.

Table 2.1 shows pair-wise ANI estimations of Strain DSM 29870 compared to other *Bacillus* species. Data shows that Strain DSM 29870 is most identical (>93%) to *Bacillus subtilis spizezenii* TU-B-10 and *Bacillus vallismortis*. The identity is lower in all other comparisons with species within the *Bacillus* genus. The ANI value is less than 95% in all comparisons and therefore it is difficult to make a definitive statement of taxonomic placement using ANI alone. ANI values less than 95% but higher than 93% are also observed between *Bacillus amyloliquefaciens plantarum* and *amyloliquefaciens* subspecies. Therefore it is quite possible that Strain DSM 29870 is a subspecies of *Bacillus subtilis*.

TABLE 2.1

Two-way pairwise ANI of *Bacillus* strain O52BCU compared to other bacterial genomes (in percentage).

| | Bacillus subtilis spizezenii TU-B-10 | Bacillus vallismortis | Bacillus subtilis 168 | Bacillus tequilensis | Bacillus amyloliquefaciens YAU_B9601 Y2 | Bacillus cereus BMG1.7 | Bacillus anthracisames |
|---|---|---|---|---|---|---|---|
| DSM29870 | 93.68 | 93.84 | 92.12 | 92.07 | 82.76 | 79.95 | 80.59 |

Ani Estimations:

An open source Ruby script (ani.rb) for ANI estimation was obtained from the Kostas lab (enveomics.blogspot.com/2013/10/anirb.html) and used for pair-wise ANI estimations.

Detailed Methods:

All the scripts and programs executed in command line were either run on Ubuntu version 10.04 or version 12.04 (Canonical Ltd.).

Core Genome Phylogenetics:

All the fasta files of the genomes were moved to the same folder and then prodigal version 2.6 was used to determine protein sequences as given in the following example:

Example of Prodigal Script Execution prodigal -i RO_NN-1_CP002906.fasta -a./Protein_files/RO_NN-1_CP002906.faa -c -m All the protein sequences were then moved to a folder in the input folder of the Phylophlan working directory (For example under Protein_files) and then phylophlan was executed as in the following example:

Phylogenetics:

Phylogenetic analysis placed Strain DSM 29870 close to *Bacillus subtilis* subspecies *spizezenii* and *Bacillus vallismortis* (FIG. 3). FIG. 3 is zoomed in to show Strain DSM 29870 relationship to its nearest neighbors. See FIG. 2 for the complete phylogram.

Conclusion:

The Average Nuclear Identity (ANI) value is less than 95% in all comparisons and therefore it is difficult to make a definitive statement of taxonomic placement using ANI alone. However, in combination with phylogenetics, we conclude that the bacterial strain DSM 29870 is distinct to known hitherto known *Bacillus* strains to a level that it at least represents a novel subspecies of *Bacillus subtilis*.

Example 3: GyrB Analysis

Background

Comparative analysis of the gyrB gene encoding the subunit B of the DNA gyrase protein was previously shown to be an efficient tool for taxonomic characterization of members of the *Bacillus subtilis* group. [*International Journal of Systematic and Evolutionary Microbiology* (2007), 57: 1846-1850].

The gyrB gene sequence of *Bacillus subtilis* strain 168 deposited as CP010052_13 in the EMBL database was used to find the gyrB gene in the genome sequence of DSM 29870.

With a Pearl Script the EMBL:CP010052_13 was used for a BlastN analysis that gave the location—contig number, position and orientation—of the gyrB gene in the genome sequence of DSM 29870. The gyrB gene sequence of DSM 29870 was subsequently manually extracted from the genome sequence.

For the comparative analysis we selected to use only a partial gyrB gene. The partial sequence of the gyrB gene of *Bacillus subtilis* DSM 29870 is shown in SEQ ID NO: 1. The sequence was translated into amino acid sequence (SEQ ID NO: 2). The amino acid sequence of the partial gyrB gene product cover amino acids 49-614 of the gyrB gene product in *Bacillus subtilis* type strain UNIPROT:P05652 [Moriya et al., 1985, "Structure and function of the region of the replication origin of the *Bacillus subtilis* chromosome. III. Nucleotide sequence of some 10,000 base pairs in the origin region." Nucleic Acids Res. 13: 2251-2265].

The Amino acid and DNA sequences were analyzed by BLAST [Altschul et al., 1990, "Basic local alignment search tool", *J. Mol. Biol.* 215: 403-410]. The amino acid sequence showed 99.3% identity to the closest related strain of *Bacillus subtilis*, the DNA sequence showed 94.6% identity to the closest relative, *Bacillus subtilis* subsp. *Spizizenii*. This indicates that *Bacillus subtilis* DSM 29870 is a novel subspecies of *Bacillus subtilis*.

Example 4: rpoB Analysis

Background

The rpoB gene encoding the RNA polymers beta subunit was previously used as a phylogenetic marker. The extensive use of rpoB was reviewed [Adékambi et al., 2009, "The rpoB gene as a tool for clinical microbiologists", *Trends in Microbiology* 17(1): 37-45]. It was used to discriminate sub-groups/closely related *Bacillus* species [Qi et al., 2001, "Utilization of the rpoB Gene as a Specific Chromosomal Marker for Real-Time PCR Detection of *Bacillus anthracis*", *Appl. Environ. Microbiol.* 67(8): 3720-3727].

The rpoB gene sequence of *Bacillus subtilis* wild type Marburg strain deposited in the EMBL database under L24376 [Boor et al., 1995, "Genetic and transcriptional organization of the region encoding the beta subunit of *Bacillus subtilis* RNA polymerase", *J. Biol. Chem.* 270(35): 20329-20336] was used to find the rpoB gene in the genome sequence of DSM 29870.

With a Pearl Script the EMBL:L24376 was used for a BlastN analysis that gave the location—contig number, position and orientation—of the rpoB gene of DSM 29870. The rpoB gene sequence of DSM 29870 was manually extracted from the genome sequence. For the comparative analysis we selected to use only a partial rpoB gene. The partial sequence of the rpoB gene of *Bacillus subtilis* DSM 29870 is shown in SEQ ID NO: 3.

The sequence was translated into the amino acid sequence. The amino acid sequence of the partial rpoB gene product is shown in SEQ ID NO: 4. It covers the amino acids equivalent to 1 to 1193 of the rpoB gene product in *Bacillus subtilis* of EMBL: L24376 [Boor et al., 1995, "Genetic and transcriptional organization of the region encoding the beta subunit of *Bacillus subtilis* RNA polymerase", *J. Biol. Chem.* 270(35): 20329-20336].

The amino acid and DNA sequences were analyzed by BLAST [Altschul et al., 1990, "Basic local alignment search tool." *J. Mol. Biol.* 215: 403-410]. The amino acid sequence showed 99.4% identity to the closest related strain of *Bacillus subtilis*, the DNA sequence showed 96.5% identity to the closest relative, *Bacillus subtilis* subsp. *Spizizenii*. This indicates that *Bacillus subtilis* DSM 29870 is a novel subspecies of *Bacillus subtilis*.

Example 5: Comparative Analysis of GyrA Extracted from the Genome Sequence

Background

Partial sequence of the gyrA gene encoding the alpha subunit of the DNA gyrase protein has previously been used as a phylogenetic marker to discriminate members of the *Bacillus subtilis* group. Twelve strains of *Bacillus amyloliquefaciens*, *Bacillus atrophaeus*, *Bacillus licheniformis*, *Bacillus mojavensis*, *Bacillus subtilis* subsp. *subtilis*, *Bacillus subtilis* subsp. *spizizenii* and *Bacillus vallismortis* were sequenced, and it was shown that *Bacillus subtilis* subsp. *subtilis* could be discriminated from *Bacillus subtilis* subsp. *spizizenii* based on this gene sequence [Chun & Bae, 2000, "Phylogenetic analysis of *Bacillus subtilis* and related taxa based on partial gyrA gene sequences", *Antonie van Leeuwenhoek* 78: 123-127,]. The partial gyrA gene sequence of *Bacillus amyloliquefaciens* KCTC $1660^T$ deposited in EMBL as AF272015 was used to identify and extract the gyrA gene from the genome of DSM 29870.

Data Analysis

With a Pearl Script the EMBL:AF272015 was used for a BlastN analysis that gave the location—contig number, position and orientation—of the partial gyrA gene of DSM 29870. The partial gyrA gene sequence of DSM 29870 was manually extracted from the genome sequence.

The partial sequence of the gyrA gene of *Bacillus subtilis* DSM 29870 is shown in SEQ ID NO: 7. The sequence was translated into amino acid sequence. The amino acid sequence of the partial gyrA gene product covers the amino-acids shown in SEQ ID NO: 8. The Amino acid and DNA sequences were analyzed by BLAST [Altschul et al., 1990, "Basic local alignment search tool", *J. Mol. Biol.* 215: 403-410]. The amino acid sequence show 97.3% identity to the closest related strain of *Bacillus subtilis* subsp *spizizenii* TU-B10, the DNA sequence showed 89.4% identity to the closest relative, *Bacillus subtilis* subsp. *spizizenii* ATCC6633, this indicates that *Bacillus subtilis* DSM 29870 is a novel subspecies of *Bacillus subtilis*.

Example 6: Determination of Inhibition of Growth of *Clostridium perfringens*

*Clostridium perfringens* strains, 23 and 48 (both are netB positive) [Gholamiandekhordi et al., 2006, "Molecular and phenotypical characterization of *Clostridium perfringens* isolates from poultry flocks with different diseasestatus", *Vet. Microbiol.* 113: 143-152] were grown overnight in tryptic soy broth (BD part 211822) supplemented with 0.6% yeast extract (BD part 212750) at 35° C. under static anaerobic conditions. 250 μL of the overnight culture of *Clostridium perfringens* was added to 250 mL of tryptic soy agar supplemented with 0.6% yeast extract at 40° C. and poured into rectangular petri plates (Nunc part 267060). The inoculated agar was then allowed to cool at room temperature after which an 8 mm diameter well was made in the agar. Plates were stored in absence of oxygen until use.

*Bacillus* DSM 29870 was grown overnight in tryptic soy broth at 35° C. under aerobic conditions. 1000 μL of the *Bacillus* culture was collected and fractionated into cell-free supernatant and cells by centrifugation. 20 μL of cell-free supernatant or 100× diluted cells in phosphate buffered saline were added directly to the wells in the *Clostridium perfringens* inoculated agar plates. A control well contained 20 μL of phosphate buffer saline. The plates were incubated for 18 hours at 35° C. under anaerobic conditions.

Inhibition of the *Clostridium perfringens* strain was noted by a circular clearing zone around the well of interest. The phosphate buffer saline well was considered a negative control based on lack of clearing zone around the well.

Cell-free supernatant and 100× diluted cells of *Bacillus* strain DSM 29870 was able to consistently inhibit growth of *C. perfringens* strains 23 and 48 in vitro. Inhibition was also seen by competitor strain "CloSTAT", for both supernatant and cells, but was not seen with competitor strain Gallipro-Tect. "CloSTAT" is a strain of *Bacillus amyloliquefaciens* that was isolated from the commercial DFM product CloSTAT, Kemin. "GalliproTect" is a strain of *Bacillus licheniformis* that was isolated from the commercial product Gallipro Tect, Chr. Hansen.

Example 7: Determination of Inhibition of Growth of *Escherichia coli*

*Escherichia coli* strains, ATCC10536 or ATCC25922, were grown overnight in tryptic soy broth (BD part 211822) supplemented with 0.6% yeast extract (BD part 212750) at 35° C. under static anaerobic conditions. 100 μL of the overnight culture of *Escherichia coli* was added to 250 mL of tryptic soy agar supplemented with 0.6% yeast extract at 40° C. and poured into rectangular petri plates (Nunc part 267060). The inoculated agar was then allowed to cool at room temperature after which an 8 mm diameter well was made in the agar.

*Bacillus* DSM 29870 was grown overnight in tryptic soy broth at 35° C. under aerobic conditions. 1000 μL of the *Bacillus* culture was collected and fractionated into cell-free supernatant and cells by centrifugation. 20 μL of cell-free supernatant or 100× diluted cells in phosphate buffer saline were added directly to the wells in the *Escherichia coli* inoculated agar plates. A control well contained 20 μL of phosphate buffer saline. The plates were incubated for 18 hours at 30° C. under aerobic conditions.

Inhibition of the *Escherichia coli* strain was noted by a circular clearing zone around the well of interest. The phosphate buffer saline well was considered a negative control based on lack of clearing zone around the well.

Cell-free supernatant and 100× diluted cells of *Bacillus* strains DSM 29870 was able to consistently inhibit growth of *E. coli* strains ATCC10535 and ATCC25922 in vitro. Inhibition was also seen by competitor strain CloSTAT, for both supernatant and cells.

Example 8: Non-Hemolytic

Hemolysis was tested according to the Technical Guidance on the assessment of the toxigenic potential of *Bacillus* species used in animal nutrition, EFSA Journal 2011; 9(11): 2445.

Sheep blood agar plates were purchased as ready to use (Becton Dickenson art 254053 or 254087). Alternatively, the agar plates can be prepared by adding 5% defibrinated sheep blood (obtained from Statens Serum Institute, Denmark) to TS-agar (Oxoid CM 131). Agar should be autoclaved at 121° C. for 20 minutes and cooled down to about 40° C. before adding the blood immediately before pouring the plates.

The *Bacillus* strains were taken from the preservation at −80° C. and streaked on TSA agar plates, which were incubated at 30° C. overnight or until growth appeared. From a single colony as little as possible of the material was used to streak a line on ¼ of an agar plate. The plate was incubated at 30° C. for 72 hours. Hemolysis/clearing zones of the *Bacillus* strains to be tested were compared with the positive and negative control. As positive control *Bacillus subtilis* ATCC 21332 was used. As negative control *Bacillus subtilis* 168 was used.

In a screening of 599 independent isolates of *Bacillus* 223 strains (37%) were hemolysis negative. In another screening 21 of 65 independent isolates of *Bacillus* (32%) were hemolysis negative. Both screenings exclusively comprised strains that based on identification by 16S rDNA sequencing belong to *Bacillus subtilis, Bacillus licheniformis, Bacillus pumilus* and *Bacillus amyloliquefaciens* (or *Bacillus* species that are difficult to discriminate from these species based on 16 S rDNA sequencing).

The non-Hemolytic *Bacillus* strains therefore seem to be common and fairly abundant in nature, but only comprising a minority of the natural strains. The non-hemolytic strains seem to be more abundant in *Bacillus licheniformis*, while most *Bacillus amyloliquefaciens* strains appear hemolytic. The following strain from this screening was hemolysis negative and selected for further studies: *Bacillus* DSM 29870.

Example 9: Sensitivity to Antibiotics

The minimal inhibitory concentrations (MIC) of eight antibiotics against *Bacillus* strains DSM 29870 were determined using broth micro dilution essentially as described in the CLSI guidelines (M07-A9 Methods for Dilution Antimicrobial Susceptibility Tests for Bacteria That Grow Aerobically; 2012). Only modification was that volumes were changed; 90 μl MHB with bacteria was added to 10 μl antibiotics dilutions, cfu's of bacteria and concentration of antibiotics were changed so final concentrations and final cfu's matched the guideline. The plates were incubated for 20-24 h instead of 16-20 h. The control strain recommended in the CLSI standard *Staphylococcus aureus* ATCC 29213 was used as control strain.

Materials

Strains:

*Bacillus subtilis* DSM 29870

*S. aureus* ATCC 29213

Antibiotics:

Chloramphenicol (Sigma C1919, 10 mg/ml, solubilized in 96% ethanol)

Clindamycin (Sigma PHR1159, 10 mg/ml, solubilized in water)

Erythromycin (ABBOTICIN from Amdipharm 40501, 50 mg/ml, solubilized in 96% ethanol)

Gentamycin (Biomedicals inc., 190057, 10 mg/ml, solubilized in water)

Kanamycin (Sigma, CAS no. 25389-94-0, 50 mg/ml, solubilized in water)

Streptomycin (Sigma, S1277, 10 mg/ml, solubilized in water)

Tetracycline (Sigma, T3383, 10 mg/ml, solubilized in water)
Vancomycin (Sigma, V-8138, 10 mg/ml, solubilized in water)
Mueller Hinton Broth 2 (Sigma/Fluka 90922)
0.9% NaCl (Sigma/RdH 31434/Merck 106404)
Tryptone soya agar plates (Oxoid CM 131)
Microtiter plates: Costar plate, polypropylene, round bottom, Corning 3879
Method
Preparation of Bacteria:

A few colonies of *Bacillus* spp. (<1 day old) were inoculated into Mueller Hinton Broth 2 (MHB) and incubated for around 4 hours at 37° C. $OD_{600}$ (BioPhotometer plus, Eppendorf) was measured and adjusted to 0.25 (equivalent to McFarland 0.5) in MHB. For the control strain direct colony suspension was used. A few colonies of *S. aureus* ATCC 29213 (<1 day old) were suspended in MHB and $OD_{600}$ (BioPhotometer plus, Eppendorf) was measured and adjusted to 0.10-0.12 (equivalent to McFarland 0.5) in MHB. The bacterial suspensions were diluted 200× in MHB.

Preparation of Assay Plates:

Antibiotics were diluted to the concentration of 640 µg/ml in MHB. A two fold dilution series was prepared in MHB down to the concentration 0.625 µg/ml. 10 µl of each dilution and of each antibiotic was pipetted into a microtiter plates. Later, when the antibiotics were mixed with the suspension of bacteria, the samples were diluted 10× (10 µL sample in a total volume of 100 µl). This resulted in the final test range of 0.06-64 µg/ml.

If the plates were not used right away the plates are stored in the freezer at −20° C. until usage.

90 µl of the bacterial suspensions were added to the assay plates. The assay plates were incubated in a plastic bag with at wet cloth at 37° C. for 20-24 h. The MIC was determined as the lowest concentration of antibiotic that completely inhibited growth of bacteria as detected by the unaided eye.

Cfu Estimation:

A 10-fold dilution series in 0.9% NaCl was made to the $10^{-3}$ of the cultures inoculated into the microtiter plates. 2×100 ul from the $10^{-3}$ dilution were plated onto two TSA plates. The plates were incubated overnight at 37° C. Number of CFU/ml was counted.

Three biological replicates of the assay were performed for *Bacillus* DSM 29870.

Results:

The MIC values obtained for *B. subtilis* DSM 29870 showed that the breakpoint values were equal to or below the breakpoint values given in the EFSA guideline (EFSA Journal 2012; 10(6):2740).

As a control *S. aureus* ATCC 29213 was tested in parallel and had MIC values within the ranges given by the CLSI standard (M100-S24 Performance Standards for Antimicrobial Susceptibility Testing; informational Supplement, 2014).

The amount of bacteria inoculated into the assay plates was measured (CFU/ml). In general the CFU/ml was very close to the target value of 1.5*$10^5$ CFU/ml. However, the CFU/ml for the *Bacillus* strains was most possibly higher than the actual value, since the bacteria tend to aggregate and one aggregated will only result in one colony forming unit (Tables 9.1 and 9.2).

TABLE 9.1

MIC results for *B. subtilis* DSM 29870

| Antibiotic | MIC 1 µg/ml | MIC 2 µg/ml | MIC 3 µg/ml | EFSA* breakpoints µg/ml |
|---|---|---|---|---|
| Chloramphenicol | 4 | 8 | 4 | 8 |
| Clindamycin | 0.25 | 0.25 | 0.25 | 4 |
| Erythromycin | 0.125 | 0.125 | 0.125 | 4 |
| Gentamycin | 0.25 | 0.125 | 0.25 | 4 |
| Kanamycin | 2 | 1 | 2 | 8 |
| Streptomycin | 4 | 4 | 8 | 8 |
| Tetracycline | 0.25 | 0.25 | 0.25 | 8 |
| Vancomycin | 0.25 | 0.25 | 0.25 | 4 |
| CFU/ml | 4.2 * $10^5$ | 2.1 * $10^5$ | 1.4 * $10^5$ | |

*EFSA Journal 2012; 10(6): 2740

TABLE 9.2

MIC results for *S. aureus* ATCC 29213

| Antibiotic | MIC 1 µg/ml | MIC 2 µg/ml | MIC 3 µg/ml | CLSI* breakpoints µg/ml |
|---|---|---|---|---|
| Chloramphenicol | 8-16 | 16 | 8 | 2-16 |
| Clindamycin | 0.125 | 0.25 | 0.125 | 0.06-0.25 |
| Erythromycin | 0.5 | 0.5 | 0.5 | 0.25-1 |
| Gentamycin | 0.5 | 0.5 | 0.5 | 0.12-1 |
| Kanamycin | 4 | 4 | 4 | 1-4 |
| Streptomycin | 8 | 8 | 8 | No information |
| Tetracycline | 0.5 | 1 | 1 | 0.12-1 |
| Vancomycin | 0.5 | 1 | 1 | 0.5-2 |
| CFU/ml | 5.2 * $10^5$ | 7.0 * $10^5$ | 7.0 * $10^5$ | |

*M100-S24 Performance Standards for Antimicrobial Susceptibility Testing; informational Supplement, 2014

Example 10 gyrB Analysis

PCR Amplification of gyrB

For the PCR amplification 1 µL of genomic DNA (see Example 2) was mixed with 12.5 µL Reddymix Extensor PCR solution (Thermo Fisher Scientific, Surrey, UK), 1 µL of each of 10 µM solutions of primers 3AF and 4R2 (Table 10.1) and 9.5 µl distilled water. For negative control PCR reactions 1 µL MQ water was added instead of DNA.

TABLE 10.1

Primers:

| Primer | Sequence[1] | SEQ ID NO: |
|---|---|---|
| 3AF | 5'-GTMTGGGAAATTGTSGACAA-3' | SEQ ID NO: 16 |
| 4R2 | 5'-GCGGTTCYACTTTRTCRCCC-3' | SEQ ID NO: 17 |

[1]Degeneration of primers: M is A or C, S is G or C, Y is C or T and R is A or G.

The PCR thermal cycler (DNA Engine DYAD BIORAD) was programmed to run; 92° C. for 2 min, 40*[94° C. for 30 s, 52° C. for 30 s, 72° C. for 60 s], 72° C. for 10 min. The PCR product was evaluated by agarose gel electrophoresis on FlashGel cassette (Lonza, Rockland, Me. USA), using FlashGel DNA marker 100 bp-4000 bp, to estimate size of the amplicon. The PCR amplification of gyrB gene was successful when a band of about 1700 nt was seen on the gel.

Purification of PCR Products

The PCR purification was done with Multiscreen PCR 96 well filterplate (Millipore, Ireland); The entire volume of the PCR reaction was taken to one well in a 96 well plate, MilliQ water up to 100 µL was added. The plate was subjected to vacuum until it was dry (20-25 s) 100 µL milli water was added, the vacuum step was repeated. The PCR product was eluted by addition of 50 µL elution buffer (elution buffer was water) and pipetting the PCR product away from the top of the filter. The purified PCR product was stored at −22° C.

Sequencing of the Genes

The DNA concentration of the purified PCR product was quantified on NanoDrop 1000 Spectrophotometer (Thermo Fisher, Waltham, Mass., USA). Four sequence reactions were set up each using 10 ng PCR product, 1 uL primer of 10 mM of one of the primers C-F, D-R, BS-F or BS-R (Table 10.2) and distilled water to 12 µL. The solutions were mixed and used for Sanger sequencing on an ABI Prism sequencer [Sanger,»DNA sequencing with chain-terminating inhibitors, «*Proceedings of the National Academy of Sciences of the United States of America*, p. 5463-5467, December 1977].

TABLE 10.2

Primers:

| Primer | Sequence[1] | SEQ ID NO: |
|---|---|---|
| C-F | 5'-GGYATYCCIGTCGGCATYCA-3' | SEQ ID NO: 18 |
| D-R | 5'-TCCATSGTYGTYTCCCAMAG-3' | SEQ ID NO: 19 |
| BS-F | 5'-GAAGGCGGNACNCAYGAAG-3' | SEQ ID NO: 30 |
| BS-R | 5' CTTCRTGNGTNCCGCCTTC-3' | SEQ ID NO: 31 |

[1]Degenerations of primers: Y is C or T, I is inosine, S is G or C and M is A or C, N is A, C, G or T.

The sequence traces were assembled to a partial gyrB gene using the SeqMan program of the Lasergene (DNA STAR 7, Lasergene). The sequence of the entire PCR product minus the primer region of *Bacillus subtilis* DSM 29870 is shown in SEQ ID NO 32. The sequence was translated into amino acid sequence (SEQ ID NO: 33). The amino acid sequence of the partial gyrB gene product cover amino acids 49-614 of the gyrB gene product in *Bacillus subtilis* type strain UNIPROT:P05652 [Moriya et al., 1985, "Structure and function of the region of the replication origin of the *Bacillus subtilis* chromosome. III. Nucleotide sequence of some 10,000 base pairs in the origin region", Nucleic Acids Res. 13: 2251-2265]. The Amino acid and DNA sequences were analyzed by BLAST [Altschul et al., 1990, "Basic local alignment search tool", J. Mol. Biol. 215: 403-410]. The amino acid sequence showed 99.2% identity to the two closest related sequences which were from *Bacillus subtilis* subsp. *spizizenii* strains ATCC663 and W23, respectively. The DNA sequence showed 94.7% identity to the closest related sequence which was from *Bacillus subtilis* subsp. *spizizenii* TU-8-10, this indicates that *Bacillus subtilis* DSM 29870 is a novel subspecies of *Bacillus subtilis*.

Example 11 rpoB Analysis

Background

The rpoB gene encoding the RNA polymers beta subunit was previously used as a phylogenetic marker to discriminate sub-groups/closely related species in *Bacillus* [Qi et al., 2001, "Utilization of the rpoB Gene as a Specific Chromosomal Marker for Real-Time PCR Detection of *Bacillus anthracis*", Appl. Environ. Microbiol. 67(8): 3720-3727].

By comparison of rpoB genes from *Bacillus amyloliquefaciens* and *Bacillus subtilis* primers were designed and a similar sequenced based evaluation was used to show that DSM 29870 is a novel subspecies of *Bacillus subtilis*.

PCR Amplification of rpoB

For the PCR amplification 1 µL of genomic DNA (see Example 2) was mixed with 12.5 µl Reddymix Extensor PCR solution (Thermo Fisher Scientific, Surrey, UK), 1 µL of each of 10 µM solutions of primers rpoB-PCR-F and rpoB-PCR-R (Table 11.1) and 9.5 µl distilled water. For negative control PCR reactions 1 µL MQ water was added instead of DNA.

TABLE 11.1

Primers:

| Primer | Sequence | SEQ ID NO: |
|---|---|---|
| rpoB-PCR-F | 5'-TACGCATGATTTGAGGGGTG-3' | SEQ ID NO: 20 |
| rpoB-PCR-R | 5'-AACCGATGTCACTTGCCTTTA-3' | SEQ ID NO: 21 |

The PCR thermal cycler (DNA Engine DYAD BIORAD) was programmed to run; 92° C. for 2 min, 40*[94° C. for 30 s, 52° C. for 30 s, 72° C. for 60 s], 72° C. for 10 min. The PCR product was evaluated by agarose gel electrophoresis on FlashGel cassette (Lonza, Rockland, Me. USA), using FlashGel DNA marker 100-4000 bp, to estimate size of the amplicon. The PCR amplification of rpoB gene was successful when a band of about 3600 nt was seen on the gel (theoretical size is 3639 nt based on embl:L24376).

Purification of PCR Products

The PCR purification was done with Multiscreen PCR 96 well filterplate (Millipore, Ireland); The entire volume of the PCR reaction was taken to one well in a 96 well plate, MilliQ water up to 100 µL was added. The plate was subjected to vacuum until it was dry (20-25 s) 100 µL milli water was added, the vacuum step was repeated. The PCR product was eluted by addition of 50 µL elution buffer (elution buffer was water) and pipetting the PCR product away from the top of the filter. The purified PCR product was stored at −22° C.

Sequencing of the Genes

The DNA concentration of the purified PCR product was quantified on NanoDrop 1000 Spectrophotometer (Thermo Fisher, Waltham, Mass., USA). Eight sequence reactions were set up each using 10 ng PCR product, 1 uL primer of 10 mM of one of the primers rpoB-seq-F1, rpoB-seq-F2, rpoB-seq-F3, rpoB-seq-F4, rpoB-seq-R1, rpoB-seq-R2, rpoB-seq-R3, and rpoB-seq-R4 and distilled water to 12 µL. The solutions were mixed and used for Sanger sequencing on an ABI Prism sequencer.

TABLE 11.2

Primers:

| Primer | Sequence | SEQ ID NO: |
|---|---|---|
| rpoB-seq-F1 | 5'-TTAATTAACAAAGAAACTGG-3' | SEQ ID NO: 22 |
| rpoB-seq-F2 | 5'-ATGTAATCGGCAATGCTTAC-3' | SEQ ID NO: 23 |
| rpoB-seq-F3 | 5'-AGGCTGTGCCTTTGATGCAG-3' | SEQ ID NO: 24 |

TABLE 11.2-continued

Primers:

| Primer | Sequence | SEQ ID NO: |
|---|---|---|
| rpoB-seq-F4 | 5'-GAAACGTAAGATTTCTGAAG-3' | SEQ ID NO: 25 |
| rpoB-seq-R1 | 5'-GAGAGCACGCAAAAGAACCG-3' | SEQ ID NO: 26 |
| rpoB-seq-R2 | 5'-GTTTCAATCGGACACATACG-3' | SEQ ID NO: 27 |
| rpoB-seq-R3 | 5'-CCGTCAGCAAGGATTTCTCC-3' | SEQ ID NO: 28 |
| rpoB-seq-R4 | 5'-TCCATACCTAAGCTTTGAAG-3' | SEQ ID NO: 29 |

The sequence traces were assembled to a partial rpoB gene using the SeqMan program of the Laser Gene (DNA STAR 7, lasergene) the sequence of the entire PCR product minus the primer region of *Bacillus subtilis* DSM 29870 is shown in SEQ ID NO: 34. The sequence was translated into amino acid sequence (SEQ ID NO:35). The amino acid sequence of the partial gyrB gene product cover amino acids 49-614 of the rpoB gene product in *Bacillus subtilis* type strain UNIPROT:P05652 [Moriya et al., 1985, "Structure and function of the region of the replication origin of the *Bacillus subtilis* chromosome. III. Nucleotide sequence of some 10,000 base pairs in the origin region", Nucleic Acids Res. 13: 2251-2265]. The amino acid and DNA sequences were analyzed by BLAST [Altschul et al., 1990, "Basic local alignment search tool", J. Mol. Biol. 215: 403-410. The amino acid sequence showed 99.3% identity to the 3 closest related sequences of *Bacillus subtilis* subsp. *spizizenii* (strain ATCC 23059, NRRL B-14472, W23) and ATCC6633 and a third that was poorly annotated in UniProt database. The DNA sequence showed 96.5 identity to the closest related sequence which was from *Bacillus subtilis* subsp. *spizizenii* TU-B-10. This indicates that *Bacillus subtilis* DSM29870 is a novel subspecies of *Bacillus subtilis*.

Example 12: Determination of Monensin Compatibility

Monensin compatibility of DSM 29870 was determined using a modified broth micro dilution similar to the method described in the Example 9. Briefly, a single colony of *Bacillus* spp. (from overnight tryptic soy agar plates) was inoculated into Mueller Hinton Broth (MHB) and cultured overnight. Sterile media was then inoculated with the overnight culture and allowed to grow for 4 hours to test bacteria in log growth phase. Cultures were then diluted once more 1:200 into fresh MHB and 90 µL of this inoculated broth was added to the diluted monensin at the indicated concentrations. Prior art strains were also tested for comparison: NN019785, NN062266 (NRRL B-50013), NN062267 (NRRL B-50104), NN062278 (PTA-6507), NN062319 (FERM BP-1096), NN062440, NN062441 (DSM 17236), NN062439.
Strains:
*Bacillus subtilis* DSM 29870.
*Bacillus licheniformis* NN019785.
*Bacillus amyloliquefaciens* NN062266 (NRRL B-50013).
*Bacillus subtilis* NN062267 (NRRL B-50104).
*Bacillus subtilis* NN062278 (PTA-6507).
*Bacillus amyloliquefaciens* NN062319 (FERM BP-1096).
*Bacillus subtilis* NN062440.
*Bacillus licheniformis* NN062441 (DSM 17236).
*Bacillus amyloliquefaciens* NN062439.

Materials:

Monensin sodium salt (Sigma, CAS no. 22373-78-0, solubilized in 96% ethanol).

Mueller Hinton Broth (Becton, Dickinson and Company, 275730).

Tryptic soy agar (Becton, Dickinson and Company, 236920).

Micro titer plates: Costar plate, polypropylene, flat bottom, Corning, 3628.

Borosilicate glass tubes: Kimbale, 16×125 mm, 73500-16125.

Adhesive gas permeable seals: Thermo Scientific, AB-0718.

Preparation of Bacteria:

*Bacillus* spp. were grown overnight on tryptic soy agar plates (40 g/L) at 37° C. Mueller Hinton broth (21 g/L) was dissolved in water and autoclaved in glass tubes containing 5 mL of broth each. A single colony of *Bacillus* spp. (from overnight plates) was inoculated into Mueller Hinton Broth (MHB) and incubated overnight at 37° C. shaking at 200 rpm. A 5 mL glass tube of fresh, sterile media was then inoculated with 25 mL of overnight culture and allowed to grow for 4 hours at 37° C. Cultures were then diluted once more 1:200 into fresh MHB. 90 µL of this inoculated broth was then added to the diluted antibiotic at the indicated concentrations.

Preparation of Assay Plates:

Monensin was diluted into 96% ethanol to a concentration of 800 µg/mL. This solution was then diluted 10-fold into sterile phosphate buffer to a concentration of 80 µg/mL. A two fold dilution series was prepared in MHB down to the concentration 2.5 µg/mL. 10 µl of each dilution and of each antibiotic was pipetted into a microtiter plate. Later, when the antibiotics were mixed with the suspension of bacteria, the samples were diluted 10× (10 µL sample in a total volume of 100 µl). This resulted in the final test range of 0.25-8 µg/ml.

90 µl of the bacterial suspensions were added to the assay plates. The assay plates were then covered with an adhesive glass permeable seal and incubated overnight at 37° C. shaking at 200 rpm. The maximum compatible concentration was determined similar to a MIC analysis as the concentration above that which inhibited 80% of bacteria as detected by the unaided eye.

Results:

A potential challenge of delivering *Bacillus* spp. in feed is the common use of antibiotics as growth promoters in feed. Therefore it is necessary to determine the compatibility of strains with commonly-used feed antibiotics in order to identify any potential conflicts with use as a direct fed microbial. Therefore, the monensin compatibility DSM 29870 was determined along with prior art strains. DSM 29870 has a higher level of compatibility with monensin than the prior art strains included herein: NN019785, NN062266 (NRRL B-50013), NN062267 (NRRL B-50104), NN062278 (PTA-6507), NN062319 (FERM BP-1096), NN062440, NN062441 (DSM 17236), NN062439.

TABLE 12.1

| | Deposit number | Species | Product Name | Monensin (µg/mL) |
|---|---|---|---|---|
| NN062677 | DSM29870 | *Bacillus subtilis* | | 2.7 |
| NN019785 | | *Bacillus licheniformis* | BioPlus 2B (Chr. Hansen) | 0.8 |
| NN062266 | NRRL B-50013 | *Bacillus amyloliquefaciens* | Eviva Pro (Dupont) | 1.1 |
| NN062267 | NRRL B-50104 | *Bacillus subtilis* | Eviva Pro (Dupont) | 1.1 |
| NN062278 | PTA-6507 | *Bacillus subtilis* | Eviva Pro (Dupont) | 1.4 |
| NN062319 | FERM BP-1096 | *Bacillus amyloliquefaciens* | Calsporin (Calpis) | 2.2 |
| NN062440 | | *Bacillus subtilis* | GalliPro Max (Chr. Hansen) | 0.4 |
| NN062441 | DSM 17236 | *Bacillus licheniformis* | GalliPro Tect (Chr. Hansen) | 0.9 |
| NN062439 | | *Bacillus amyloliquefaciens* | Clostat (Kemin) | 2.1 |

What is claimed is:

1. A method comprising administering *Bacillus subtilis* DSM 29870 to an animal.

2. The method of claim 1, wherein said *Bacillus subtilis* DSM 29870 is administered to said animal via feeding.

3. The method of claim 1, wherein said *Bacillus subtilis* DSM 29870 is administered to said animal as part of an animal feed composition or an animal feed additive composition.

4. The method of claim 1, wherein said *Bacillus subtilis* DSM 29870 is administered to said animal as part of a composition comprising from $10^5$ to $10^{12}$ colony-forming units of *Bacillus subtilis* DSM 29870 per gram of said composition.

5. The method of claim 1, wherein said *Bacillus subtilis* DSM 29870 is administered to said animal as part of a composition comprising *Bacillus subtilis* DSM 29870 spores.

6. The method of claim 1, wherein said *Bacillus subtilis* DSM 29870 is administered to said animal as part of a composition comprising one or more of the following: glycerol, ethylene glycol, 1,2-propylene glycol, 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose.

7. The method of claim 1, wherein said *Bacillus subtilis* DSM 29870 is administered to said animal as part of an animal feed composition or animal feed additive composition comprising from $10^5$ to $10^{12}$ colony-forming units of *Bacillus subtilis* DSM 29870 per gram of said composition.

\* \* \* \* \*